(12) United States Patent
Wolf

(10) Patent No.: US 12,364,427 B2
(45) Date of Patent: Jul. 22, 2025

(54) IMPLANTABLE INTRACARDIAC ATRIAL RESTRAINING DEVICE AND SYSTEM FOR SENSING AND IDENTIFYING LOCATIONS OF CHANGES TO CARDIAC TISSUE THAT IMPACT ELECTRICAL SIGNALS THEREIN

(71) Applicant: Wolf Cardio, LLC, Houston, TX (US)

(72) Inventor: Randall K. Wolf, Houston, TX (US)

(73) Assignee: Wolf Cardio, LLC, Houston, TX (US)

( * ) Notice: Subject to any disclaimer, the term of this patent is extended or adjusted under 35 U.S.C. 154(b) by 0 days.

(21) Appl. No.: 18/583,797

(22) Filed: Feb. 21, 2024

(65) Prior Publication Data

US 2024/0277278 A1 Aug. 22, 2024

Related U.S. Application Data

(60) Provisional application No. 63/486,438, filed on Feb. 22, 2023.

(51) Int. Cl.
| | | |
|---|---|---|
| *A61B 5/36* | (2021.01) | |
| *A61B 5/00* | (2006.01) | |
| *A61B 5/287* | (2021.01) | |
| *A61B 5/29* | (2021.01) | |
| *A61B 5/339* | (2021.01) | |
| *A61B 5/361* | (2021.01) | |

(52) U.S. Cl.
CPC .............. *A61B 5/361* (2021.01); *A61B 5/287* (2021.01); *A61B 5/29* (2021.01); *A61B 5/339* (2021.01); *A61B 5/686* (2013.01)

(58) Field of Classification Search
None
See application file for complete search history.

(56) References Cited

U.S. PATENT DOCUMENTS

| | | |
|---|---|---|
| 5,755,761 A | 5/1998 | Obino |
| 5,855,592 A | 1/1999 | McGee et al. |
| 6,516,231 B1 | 2/2003 | Flammang |

(Continued)

FOREIGN PATENT DOCUMENTS

| | | |
|---|---|---|
| WO | WO-95/10226 A1 | 4/1995 |
| WO | WO-2018/085545 A1 | 5/2018 |

(Continued)

OTHER PUBLICATIONS

International Search Report and Written Opinion on PCT/US2023/063074 dated Oct. 10, 2023, 13 pgs.

(Continued)

*Primary Examiner* — Ankit D Tejani
(74) *Attorney, Agent, or Firm* — Foley & Lardner LLP

(57) ABSTRACT

An implantable intracardiac atrial retraining device and system may be configured to sense and identify locations of changes to cardiac tissue that impact electrical signals therein. The implantable intracardiac atrial retraining device may include a septum electrode that crosses through the septum and multiple extension electrodes may extend therefrom along endocardium of one or both of the atria. The extension electrodes may be used to sense electrical electrodes produced by the sinoatrial node and one or more electrical characteristics of the heart tissue. If any changes to the electrical signals and/or electrical characteristics of the heart tissue change, a notification may be generated to notify a physician and/or patient.

18 Claims, 41 Drawing Sheets

(56) References Cited

U.S. PATENT DOCUMENTS

| | | | |
|---|---|---|---|
| 7,448,999 B1 | 11/2008 | Karicherla et al. | |
| 7,515,971 B1 | 4/2009 | Doan | |
| 8,021,359 B2 | 9/2011 | Auth et al. | |
| 8,543,193 B2 | 9/2013 | Satin et al. | |
| 8,849,384 B2 | 9/2014 | Greenspan | |
| 9,492,657 B2 | 11/2016 | Gerber | |
| 2005/0119647 A1* | 6/2005 | He | A61B 18/1492 606/41 |
| 2006/0041300 A1 | 2/2006 | Zhang et al. | |
| 2007/0073179 A1 | 3/2007 | Afonso et al. | |
| 2009/0198297 A1 | 8/2009 | Zhang et al. | |
| 2010/0317981 A1 | 12/2010 | Grunwald | |
| 2012/0172944 A1* | 7/2012 | Dori | A61N 1/3627 607/18 |
| 2013/0331920 A1 | 12/2013 | Osypka | |
| 2014/0207202 A1* | 7/2014 | Imran | A61N 1/0573 607/18 |
| 2016/0325079 A1 | 11/2016 | Osypka | |
| 2016/0354600 A1 | 12/2016 | Kolberg et al. | |
| 2017/0281031 A1 | 10/2017 | Houben et al. | |
| 2018/0296842 A1 | 10/2018 | Imran | |
| 2020/0054882 A1 | 2/2020 | Dale et al. | |
| 2020/0138319 A1* | 5/2020 | Spector | A61B 5/287 |
| 2021/0369394 A1 | 12/2021 | Braido et al. | |
| 2023/0264017 A1 | 8/2023 | Wolf et al. | |

FOREIGN PATENT DOCUMENTS

| | | |
|---|---|---|
| WO | WO-2021/113843 A1 | 6/2021 |
| WO | WO-2022/076801 A1 | 4/2022 |

OTHER PUBLICATIONS

International Search Report on PCT/US2020/63664 dated Mar. 10, 2021, 3 pgs.

International Search Report and Written Opinion for PCT/US2024/016776 dated Aug. 8, 2024, 13 pages.

* cited by examiner

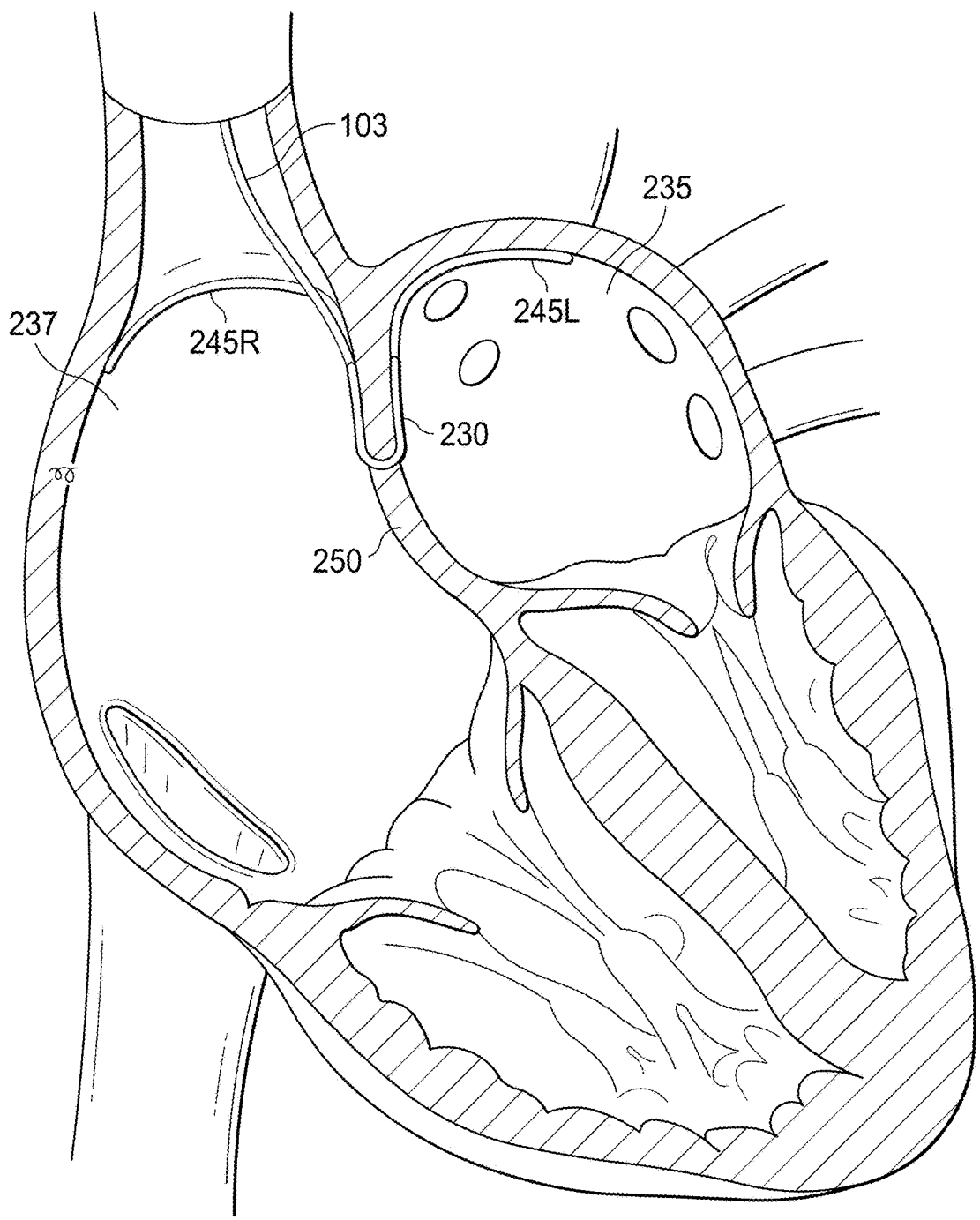
FIG. 2I
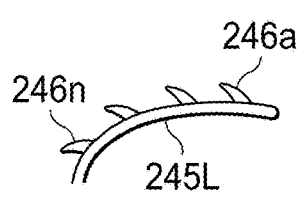
FIG. 2I-A
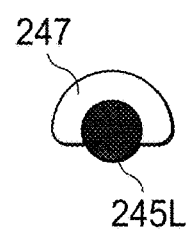
FIG. 2I-B

Alternative embodiment where the nitinol anchor is gold plated

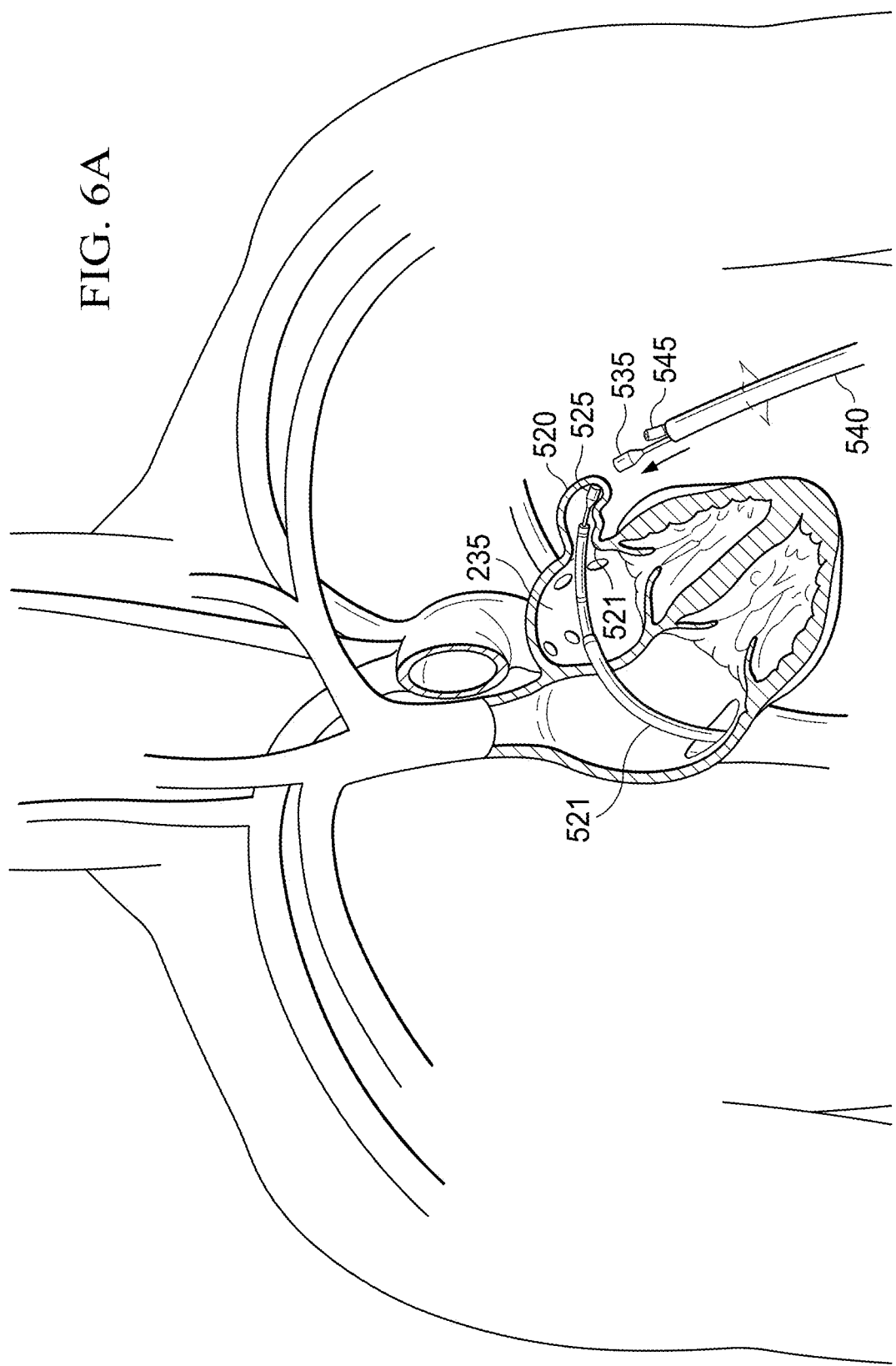

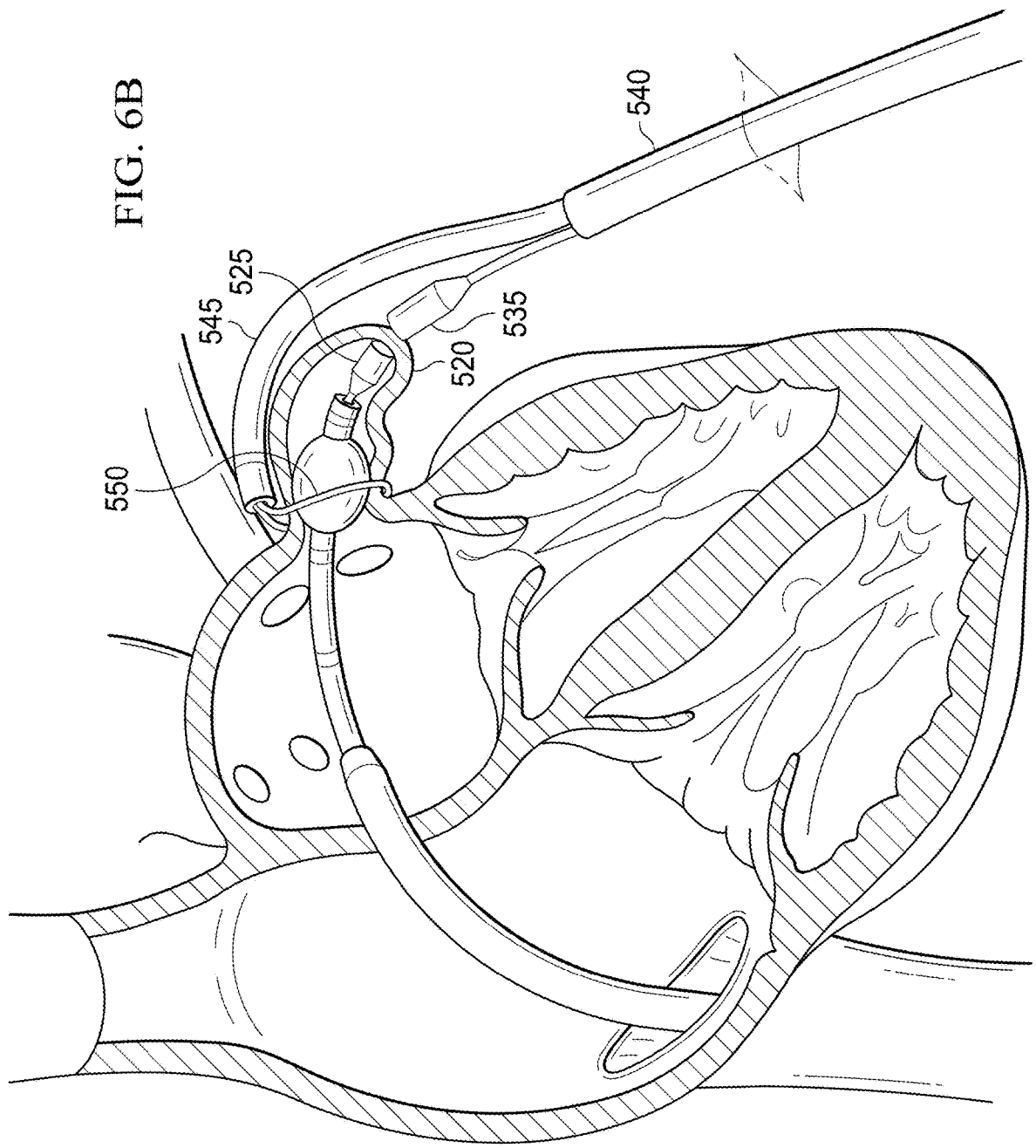

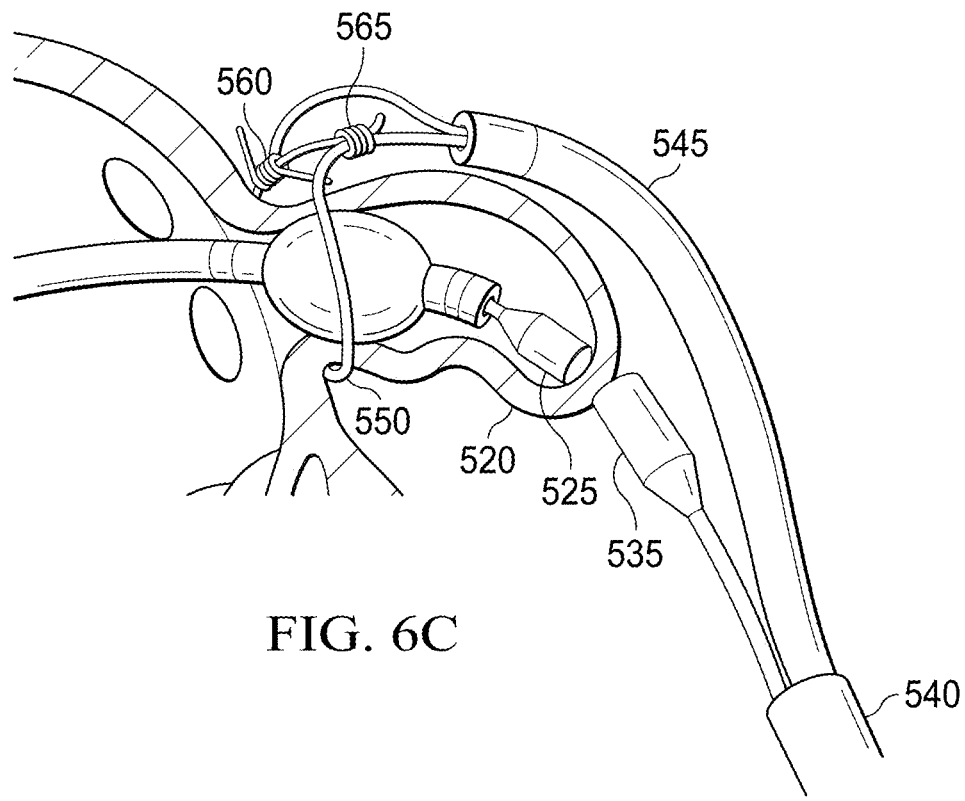
FIG. 6C
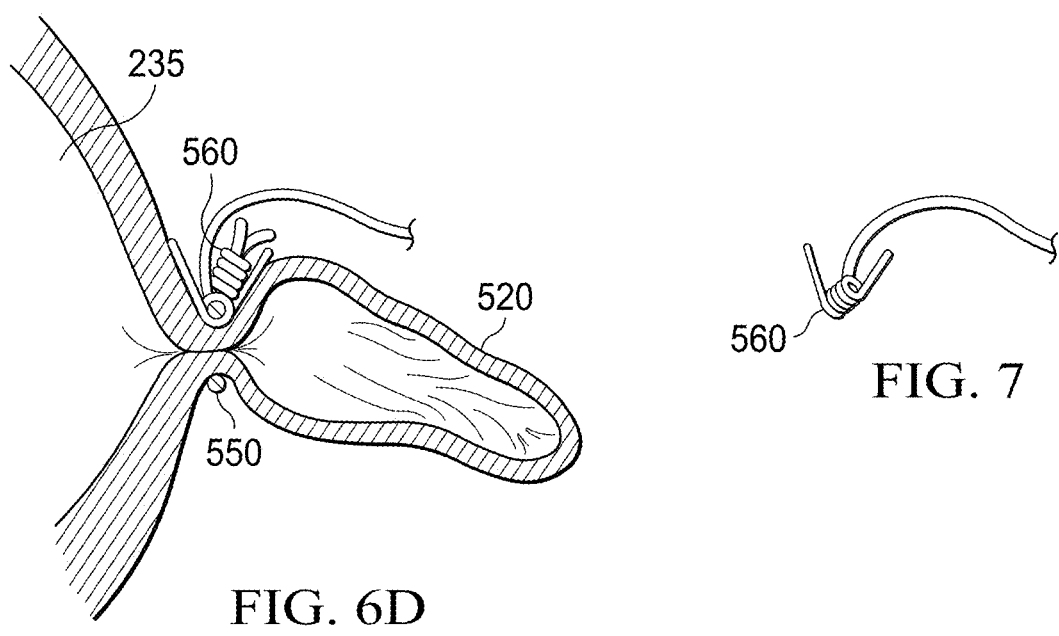
FIG. 6D
FIG. 7

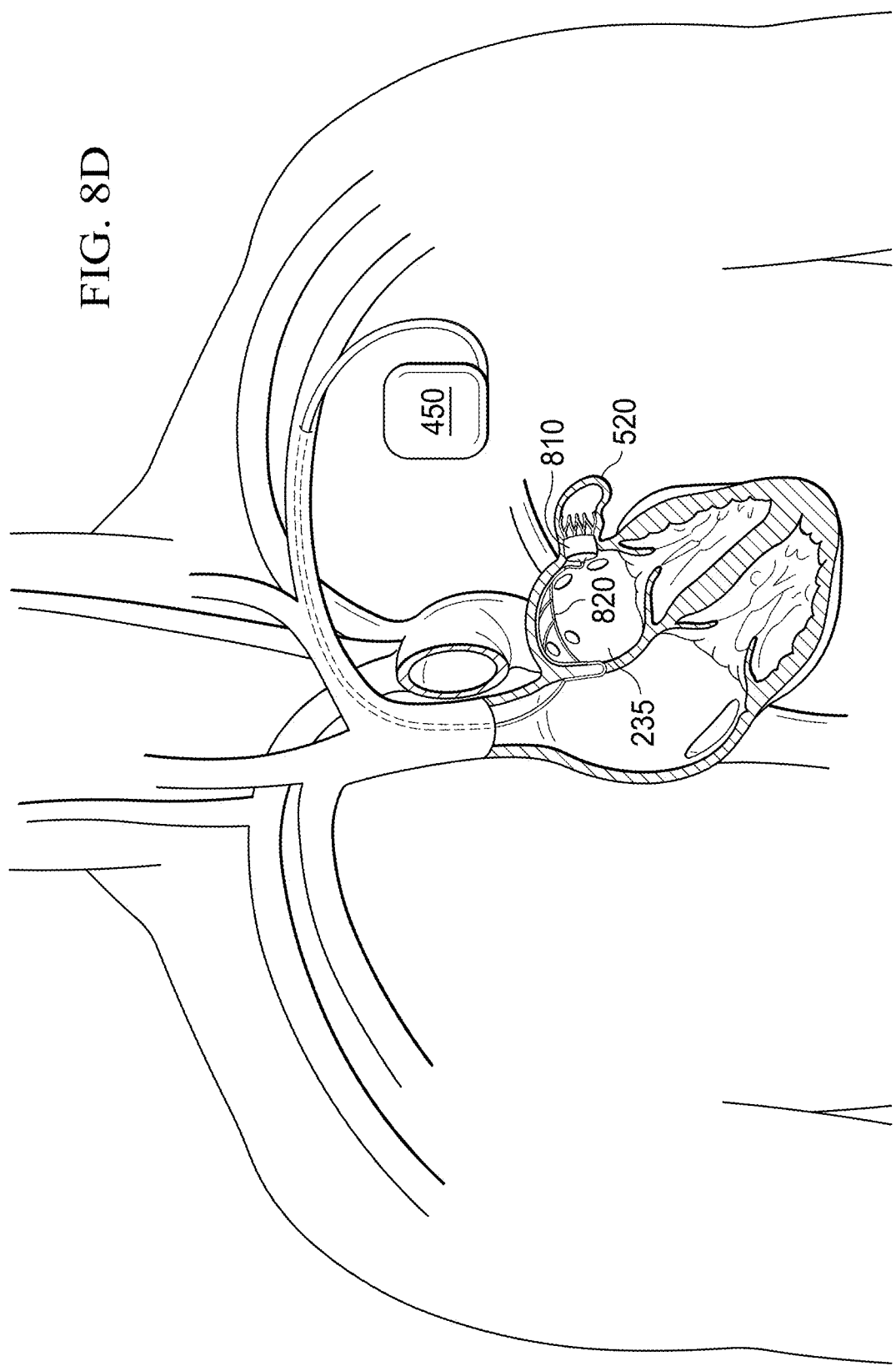

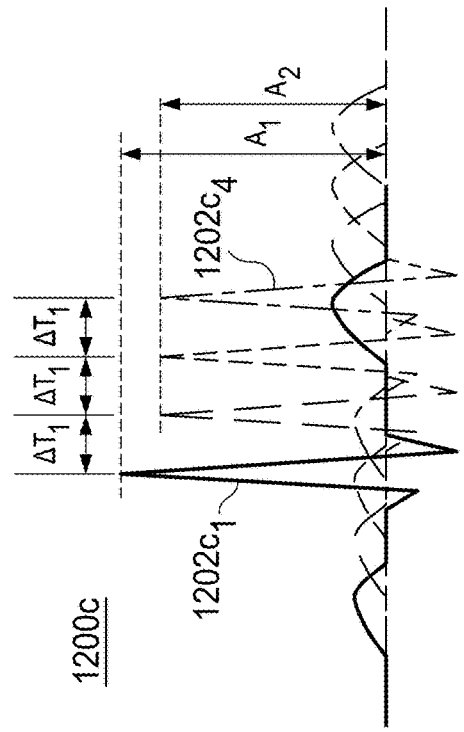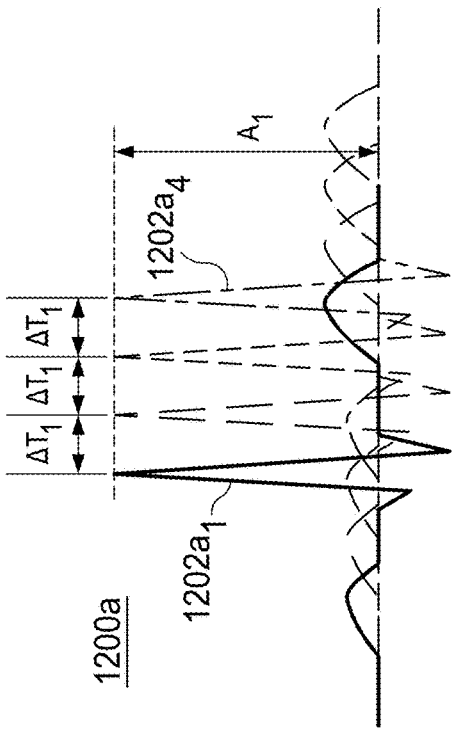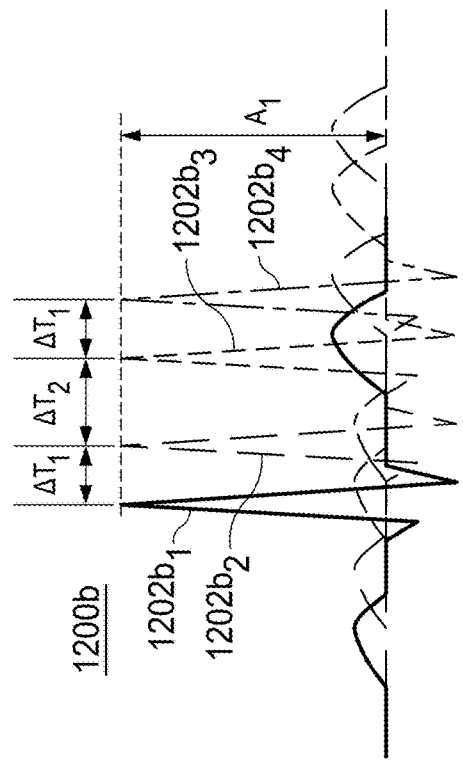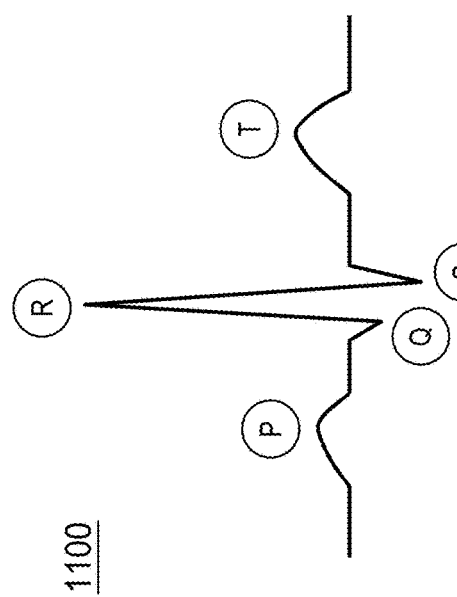

IMPLANTABLE INTRACARDIAC ATRIAL RESTRAINING DEVICE AND SYSTEM FOR SENSING AND IDENTIFYING LOCATIONS OF CHANGES TO CARDIAC TISSUE THAT IMPACT ELECTRICAL SIGNALS THEREIN

RELATED APPLICATIONS

This application claims priority to U.S. Provisional patent application having Ser. No. 63/486,438 filed on Feb. 22, 2023; the contents of which are hereby incorporated by reference in their entirety.

BACKGROUND OF THE INVENTION

Wires placed in the heart connected to pacemakers have been used in the right side of the human heart since 1957 (Earl Bakken-founder of Medtronic). Since then millions of wires for sensing, pacing and defibrillating the heart have extended and saved lives around the world. Despite this body of work, wires are not used on the left side of the heart. Mitral valve devices, left atrial occlusion devices, and septal occlusion devices have been placed on the left side of the heart for decades.

However, wires traditionally have not been placed on the left side of the heart because of the risk that a thrombus collecting on a wire floating free in the heart can detach. If the wire is on the right side of the heart, and a thrombus develops and detaches, the thrombus can only travel to the lungs, and intrinsic enzymes can be used to break down the thrombus or clot. However, if a wire is on the left side of the heart and a thrombus develops and detaches, the clot will travel into the aorta and to the brain. The brain has no intrinsic mechanism to dissolve the clot, and a stroke can occur, which can be devastating.

Defibrillating the human heart has saved many lives. Initially performed only externally (through the skin), defibrillators are now placed internally (endovascular and intracardiac and extracardiac) to emergently defibrillate the heart to terminate dangerous arrhythmias. Current defibrillators need relatively high energy (as measured in joules) to defibrillate the heart. These shocks are painful to the patient and cause incredible anxiety. The energy utilized wears down the batteries quickly, which then require replacing. Replacing the generators and batteries are expensive (the batteries are incorporated into the generators) and there is the risk of infection with generator and battery replacement. Infections are sometimes fatal and are very expensive to the medical system.

Atrial fibrillation (AFIB or AF), the most common human cardiac arrhythmia, causes great morbidity, mortality, and cost. AF often causes the heart to beat irregularly, such as too quickly. One of the biggest concerns with AF is the risk of stroke. In fact, people with AF have approximately five times greater risk of stroke than those who do not have AF. It is estimated that by 2030, approximately 12 million people in the U.S. will have AFIB. Around 46.3 million individuals are estimated to be suffering from AFIB and about one-third of the total AFIB population is asymptomatic (aka silent AF), according to the Global Burden of Disease project.

By way of background, during a normal heartbeat, the upper chambers (atria) and lower chambers (ventricles) of the heart work together to pump blood to the rest of the body. AFIB occurs when the upper chambers of the heart beat irregularly, and do not pump all of the blood to the lower chambers, thereby causing some blood to pool and potentially form clots in the left atrium or elsewhere. If a clot breaks loose, the clot can travel through the bloodstream to the brain and lead to a stroke. Strokes related to AFIB are often more severe compared to strokes with other underlying causes.

Although AF is present only in the atrial chambers of the heart today the entire heart is defibrillated for AF because leads to the heart for defibrillation generally do not include leads placed in the left atrium (LA). Accordingly, it is difficult to sense the left atrium for the occurrence of arrhythmias and difficult to selectively defibrillate the left atrium. As such, defibrillating the heart in response to left atrium generally requires defibrillating the entire heart.

To help with an early diagnosis of AFIB, a number of devices have been used to sense AFIB. Most of the time intermittent monitoring devices, such as electrocardiogram (ECG), are used to measure the heart. Traditional ambulatory Holter Monitors (HM), which are connected by electrodes to the chest, are still regularly used, but can only be used for varying lengths of time because of their inconvenience. Wearable devices, such as wrist-worn wearables, have more recently been used. Wrist-worn wearables are typically in the form of smartwatches (e.g., Apple Watch® and Fitbit®) that analyze heart rhythm and detect AFIB using photoplethysmography (PPG). Blood pressure monitors are also available. Patch ECG monitors are also available. Implantable electronic devices, such as pacemakers, cardiac implantable electronic devices, subcutaneous cardiac monitors are also available. However, each of these types of devices (intermittent monitoring devices, Holter Monitors, wearable devices, blood pressure monitors, and implantable electronic devices) are generally limited to determining that an AFIB is occurring or exists, but do not provide much other information.

The primary surgical procedure for treating lone AF is ablation performed by an electrophysiologist. There are a few types of ablation that are currently available. Ablation uses radiofrequency (heat) or cold energy (cryoablation) to scar a small section of heart tissue that a doctor has identified as the likely cause of the heart's electrical problems. The heart relies on a steady, consistent flow of electrical impulses to coordinate the beating of the atria (upper chambers) and the ventricles (lower chambers). When the electrical flow to the heart's upper chambers does not work correctly, improper electrical flow in the heart's upper chambers can cause a fast and irregular rhythm. Eliminating the cause of this problem often allows the heart to return to a normal, healthy rhythm. Ablation can be done surgically, usually when undergoing heart surgery for another reason, such as getting a heart valve fixed. Ablation can also be done with a less invasive procedure called pulmonary vein isolation, which is typically performed in a hospital's electrophysiology or cardiac catheterization lab.

To identify heart tissue that may be causing the AF problem, patients typically are admitted into an AF lab. A patient is often sedated or under general anesthesia when the testing to identify the heart tissue that is causing the AF problem is performed and then patient's hearts are usually put into an AF condition, thereby allowing the doctor to perform the identification. Various tools may be used to identify the heart tissue causing the AF problem. One such tool is a catheter that can map the heart onto a computer screen to allow the doctor to help identify the problematic tissue. Patients often have unpleasant experiences with such procedures because of pain and discomfort after such a procedure is performed. As understood, heart tissue that causes AF tends to reoccur over time in different locations. When new AF occurs, the same process of identifying the heart tissue that is causing the AF has to be performed again. And, the cost of such AF lab analysis can be significant and, of course, cause additional discomfort and pain to the patient. Hence, there is a need for being able to identify heart tissue that is causing AF using a new technique outside of the EP lab and in real-time.

SUMMARY OF THE INVENTION

The embodiments described herein pertain to various configurations of low profile electrodes and accompanying structures that hold the electrodes and wires against the endocardium (eliminating free floating wires) and configured to be attached at or near the left atrium of the heart to allow for low energy recording, sensing, pacing, simulation, and/or defibrillation of both atria in response to atrial fibrillation or other atrial arrhythmias. The electrodes are attached to the septum of the atria in a position that is favorable for easy and secure deployment, maintaining a low profile placement. This attachment also allows for repeated crossing of the intra atrial septum at later dates, for additional ablation procedures or placement of additional closure or valve devices. The device can be fitted with a radio-opaque marker to facilitate later crossing of the intra atrial septum.

In addition to defibrillating the upper chambers of the heart, these electrodes and accompanying structures can be utilized to sense and map normal and abnormal electrical impulses, and deliver energy to terminate the initiating abnormal focus or foci. The devices can also be used in conjunction with leads implanted in the right atrium, the right ventricle, the coronary sinus, leads attached to other devices in the atria, and leads on the outside of the heart. In one embodiment, the electrode is configured to attach to the atrial septum, with the wire attachment that holds the wires against the heart tissue. In another embodiment, the electrode configuration is attached to a modified atrial septal closure device, which could also be an atrial septal opening device, again with the special attachment keeping the wires held fast against the heart wall. In another embodiment, the electrode is configured to be part of an atrial appendage closure device, also with the special attachment that keeps the wire from free floating, on either the inside (endocardial surface) or outside (epicardial surface) of the heart. In yet another embodiment the electrode is configured to be part of a mitral valve device, or may be incorporated into any valve repair or replacement device, whether placed by conventional open heart surgery or by an endovascular technique.

A useful feature is that these embodiments allow the electrodes and wires to be held fast against the heart tissue, which like mitral devices commercially available, avoid thrombus formation on the electrodes and wires. The described devices then allow sensing, pacing and/or defibrillation of the left side of the heart that has not been clinically addressed before. For instance, these devices could be used to directly pace the left atrium. Traditionally, only the right atrium can be accessed for pacing. In many patients, because of intrinsic conduction issues or distension of the atria, the right atrial pacing is not always in synch with the left atrium. With the new device in the intratribal septum, the left atrium or about the left atrium—in clinical practice both atria can be paced. This could allow for synchronous bi-atrial pacing, which improves the efficacy of atrial pacing and would improve cardiac output and ejection fraction in some patients.

Because heart tissue that causes AF tends to occur in different locations over time (i.e., different areas of heart tissue disrupts or blocks electrical signals over time), a system with an implantable heart sensing structure that is used to sense problematic areas of the heart tissue by an electronic device (e.g., pacemaker, defibrillator, mobile device, etc.) may be used. The implantable heart sensing structure may include multiple extension electrodes that are implanted and extend along a wall of one or more heart chambers that may sense electrical signals or electrical characteristics of the heart tissue. The abnormal focus or foci could be identified in real-time, outside of the EP lab and then focused treatment could be delivered real time as well. In an embodiment, the implantable heart sensing structure forms a matrix. In the event of an AF event, electrical signals that are indicative of problematic heart issue may be sensed and used to detect location of the problematic heart tissue. The system may be configured to sense changes in electrical characteristics of the heart wall over time, thereby enabling a doctor to perform an ablation of the problematic tissue prior to an AF event occurring. In some circles, the ability to monitor a patient's heart after an AF event to identify and locate potential future AF events is considered the holy grail of minimizing or preventing future AF event prevention.

One embodiment of a method for sensing heart tissue that causes atrial fibrillation (AFIB) may include measuring, via a plurality of electrical conductors disposed on endocardium of a heart wall within respective at least one chamber of a heart, an electrical signal characteristic. A determination may be made that the electrical signal characteristic is indicative of an AFIB event. Responsive to determining that the electrical signal characteristic is indicative of an AFIB event, a location of the heart wall within the heart chamber(s) relative to positions of the electrical conductors that caused the AFIB event may be identified.

One embodiment of an electronic device, such as a pacemaker, may include a non-transitory memory, an input channel configured to receive a plurality of electrical signals received from multiple extension electrodes that extend along a heart wall within at least one chamber of a heart, and a processor in electrical communication with the non-transitory memory and input channel. The processor may be configured to measure each of the electrical signals. Respective measured electrical signals may be stored in the non-transitory memory. A determination as to whether any of the measured electrical signals are indicative of heart tissue that causes heart-generated electrical signals to be delayed, accelerated, or attenuated in ways that are different from healthy heart tissue. Responsive to determining that the electrical signals are indicative of a heart tissue that causes heart-generated electrical signals to be delayed, accelerated, or attenuated in ways that are different from healthy heart tissue, a notification signal indicative of the location may be generated. Furthermore, the identification of the location may be used to deliver specific energy in several ways to the location to treat or prevent degeneration into AF.

BRIEF DESCRIPTION OF THE FIGURES

For a detailed description of various examples, reference will now be made to the accompanying drawings in which:

FIGS. 2I-2M are illustrations of illustrative alternative embodiments of electrical electrodes and sub-processes for implantation thereof that may be used in conjunction with a septal electrode.

FIGS. 6A-6D illustrate a medical procedure for implanting the closure device and associated electrode of FIG. 5.

FIG. 7 shows a close-up view of one example of the electrode configured to be coupled to the atrial appendage closure device of FIG. 5.

FIGS. 8A-8D illustrate another embodiment in which an electrode is part of an atrial appendage closure device in which the closure device is internal to the atrial appendage.

FIG. 11 is an electrocardiogram (ECG) graph showing electrical signal of a typical, healthy heartbeat captured by an electrocardiogram measurement of a heart.

FIGS. 12A-12C are ECG graphs of a sequence of illustrative electrical signals.

DETAILED DESCRIPTION OF THE INVENTION

Figure 1:
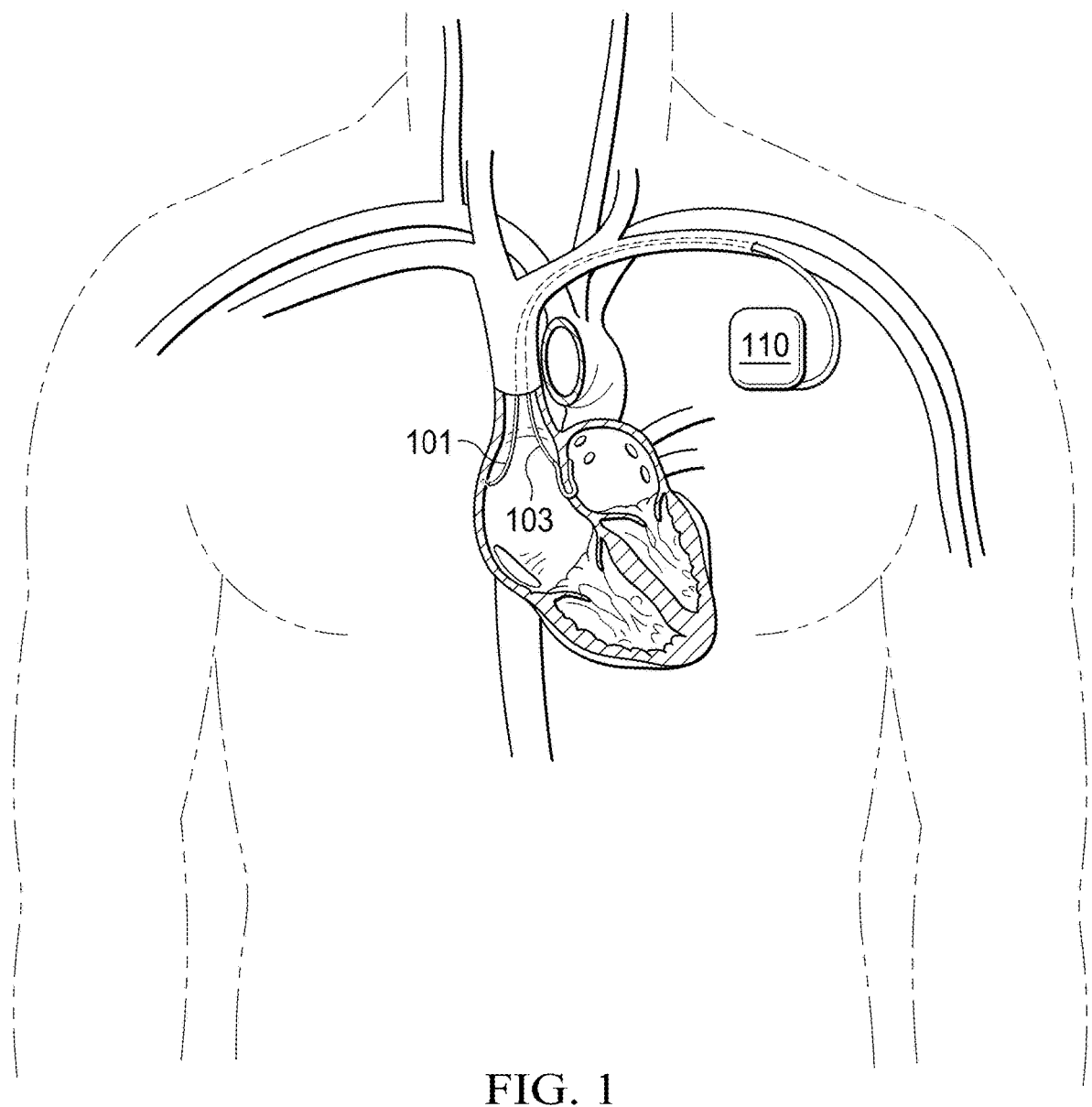
FIG. 1 illustrates a septal electrode attached to the atrial septum, and its extensions which keep the wires against the heart tissue.

Low profile restraining devices are described herein which eliminate the problem of current intracardiac leads which generally are permitted to free float within the interior volume of the corresponding cardiac chamber. The described embodiments include a mechanism that keep a portion of the lead fixed against the endocardium of the left atrium, where the electrode and lead will become embedded against the wall of the heart. Thus, thrombus is avoided with the described low-profile devices on the left side of the heart. Placement of the leads, with these devices, on the left side of the heart facilitates new therapies for the treatment of cardiac disease. The restraint mechanisms described herein can be extended to other chambers of the heart. The device allows for repeat crossing of the septum. Indeed, with a radio-opaque marker on the septal portion of the device, repeated crossing of the septum may be made more quickly and safely.

Beneficially, the described examples are directed to leads connected to the left atrium. For atrial arrhythmias (arrhythmias in the upper chambers of the heart), left atrial leads are a better way to sense AF and selectively defibrillate the upper chambers. A much lower energy can be used (1-10 joules) compared to defibrillating the entire heart. Accordingly, the patient experiences much less discomfort and battery life is increased. Leads in the LA can also provide a record of where the AF is initiating, which could guide further treatment to eliminate the focus. A left atrial lead requires careful design to avoid thrombus and embolism. The embodiments described herein pertain to a device placed entirely by a percutaneous route. The device is low profile and sits flat against the endocardial wall and becomes strongly embedded in tissue. The low-profile nature of the device avoids or reduces the risk of thrombus formation. The described device provides a solution for sensing and treating AF and other supraventricular arrhythmias, with lower power, and with shocks that are less painful or pain-free to the patient.

The embodiments described herein pertain to an implantable device that is connected to wires that contain nitinol or other types of shape memory metal or plastic or other metal or metal alloy or combination that creates some grasp against the septum and torsion that keeps the wires against the walls of the heart and prevents free floating wires. These devices can be placed in or around the left atrium of the heart, as well as on the right side of the heart. The restraining device applies passive force to the tissue by a curved wire bent to a looped state to provide a suitable amount of torsion. The devices can have protrusions to hold the device in place and prevent slippage until tissue healing occurs. The electrode portion of the device can be coated with materials such as gold to increase its conductivity. Incorporated into the curved wire is an extension of conducting wire, also coated with a material to improve conduction (such as gold plating), to increase the surface area of the device. Beneficially, the extension will lie against the heart tissue, because of wire torsion. The device is also incorporated with insulated wire(s) that will hug the heart wall. The insulated portion of the device will have an outer nitinol or other shape metal or plastic or other metal or composite that keeps the wires out of the blood stream. As in other devices in the heart that abut the endocardial surface, this device and its extensions and will become incorporated into the atrial tissue and will remain out of the flow of blood through the heart.

The devices then exit the heart, as with commercially available devices, to connect to a pacemaker, defibrillator or transducer or some combination of the these. This allows the device to receive and transmit an electrical charge from a remote site, such as a transducer or pacemaker. The transducer and pacemaker devices are available from several manufacturers, such as Medtronic and St. Jude Medical. The device sits flat against the atrial septal wall and becomes strongly embedded in tissue. This low profile discourages thrombus formation, and therefore allows the devices to be placed on the left side of the heart. In clinical practice, the devices with the extensions can be used on the right side of the heart also. The device has excellent electrical contact. The restraining device is held passively against the atrial septum. The unique property of the restraining device easily attaching to the atrial septum with a low profile provides a safe route for deployment. Since the extensions and the wires are constructed with a shaped memory metal or other material that holds the extensions and wires against the endocardium, the device can be deployed on the left side of the heart.

Currently transseptal punctures are commonplace during electrophysiologic (EP) studies. The wires for deployment of the device, such as a transseptal sheath and guidewire and obturator are already ideally situated during the transseptal puncture, which is utilized to enter the left atrium. Usually these EP studies are for the treatment of AF, including mapping and ablation and closure of the left atrial appendage, so it is straight-forward to place the restraining device during an EP procedure. Prior ways to achieve good electrical contact inside the heart include screws, barbs, hooks, pins and electrode plates. All these can be incorporated into the distal restraining device and to the extensions and special wires to help hold the devices against the heart wall. This also ensures good electrical contact. The device can incorporate coatings such as steroids to prevent fibrosis, low contact or high energy. The device can include a bioabsorbable component, such that after the electrode becomes embedded in tissue, the remaining restraining portion of the device reabsorbs. The device may also contain an antithrombotic coating, which helps prevent thrombus formation until the device is surrounded by tissue ingrowth. The device is carefully designed to be low profile, but with enough strength in the deployed position to provide complete stability in the intra-atrial septum. The restraining device on the septum may also contain material to cause certain portions of the device to be radio-opaque so as to guide later access to transeptal punctures, which may render future transeptal punctures faster, easier, and safer.

The restraining device can be integrated into any other device placed in or around the left or right atrium. The restraining device can be modified to work with any device that is to be placed in or around the right or left atrium, including, but not limited to atrial septal closure devices, left atrial closure devices (both intra and extracardiac) and valve repair or replacement devices. In the case of a septal occlusion device, the restraining device is modified to be incorporated into the rings of the septal closure device. Several possible iterations include three electrode conducting rings around the areas of the septal device that abut the endocardium of the septum. The exact configuration of the wire array can be changed depending on the device configuration, the surface area in contact, and the resistance generated. In the case of a mitral valve replacement, the retraining device can be modified to fit in a groove where the valve device abuts atrial tissue. The wire electrodes of the device may be circular or may be cross-hatched, or other configuration to provide the therapeutically sufficient electrical output at the lowest energy with a suitable resistance profile.

The retraining device could be delivered together with the valve or separately. The distal end of the lead can be affixed to, for example, the atrial septum, in or around the left atrial appendage, or in a mitral valve device. This allows for low energy defibrillation of the atria in response to atrial fibrillation or other atrial arrhythmias. The device can also be used to sense electrical activity on the endocardial surface. This information may be recorded and stored for determining the earliest site and other sites of atrial arrhythmias. This information may then direct treatment either with the device, for termination of the arrhythmia by pacing or other electrical stimulation through the device, and/or for later treatment with ablation during an EP procedure.

It can be used in conjunction with other leads and wires in both atria of the heart, or left atria and either right ventricle, left ventricle or coronary sinus that can be used to defibrillate the atria. It can be used in conjunction with electrodes on the outside of the heart as well, such as epicardial leads and electrodes. A lead placed inside the atria can facilitate defibrillation using a relatively low energy (1-10 Joules, J) waveform, delivered in many different ways, to reliably defibrillate or pace the atria.

The lead and accompanying extensions and wires can be placed into the patient via blood vessels in the groin, neck, or other areas. The distal region of the lead has electrodes and is placed in or around the left atrium (e.g., atrial septum, in or around the left atrial appendage, or in a mitral valve device). The wire configuration keeps the wires against the heart walls. The proximal end of the wire can be connected to a small defibrillator unit or a transducer that is placed subcutaneously in the patient. Such pacemakers and defibrillators can sense, pace and defibrillate. Because of the novel placement of the device, the upper chambers of the heart, the atria, can be selectively defibrillated, allowing for a very low energy defibrillation. The device also allows for sensing directly in the left atrium, which could be used to detect the origin of arrhythmias and could be used to selectively pace the left atrium in many configurations. If a transducer is used, power can be transferred to the transducer transcutaneously from an external device.

In one embodiment and as noted above, a restraining device is used to hold the left atrial wire in place against the atrial septum. A restraining device is a passive mechanical device that allows atrial defibrillation of both atria. Two devices are illustrated in FIGS. 1-4B. One is a device that has a spring effect to provide adequate restraining force to hold the wire in place against the septum, but without damaging the septum. This device can have protrusions to help hold the device in place and prevent slippage until healing occurs. This device can have extensions to provide for additional surface area for optimal sensing, pacing, and defibrillation. The extensions contain memory shaped metal or other similar substance to provide torsion, which keeps the extensions against the walls of the heart and out of the flow of blood through the heart. The second device is an array that attaches to or replaces an atrial septal defect closure device. Both can be placed in the patient at the end of a medical procedure, such as a catheter ablation procedure, to treat atrial fibrillation, or as a stand-alone procedure. Through a combined groin and subclavian approach (the left subclavian approach is illustrated), the wires placed from the groin can be brought to the subcutaneous position in the subclavian area, and then the defibrillator device can be placed.

FIG. 1 depicts an arrangement of the leads with one cardiac atrial lead 101 placed in the right atrium (similar to the atrial lead of a dual chamber pacing configuration). Part of this embodiment is the placement of a second cardiac atrial lead 103 (the device) in the left atrium, which allows for specific atrial sensing, pacing, and/or defibrillation, with a very small amount of energy (approximately 1-10 joules). The distal end of the left atrial lead 103 includes a shape memory structure or other solid or composite material that is configured to hold a portion of the lead 103 against a person's endocardium. The shape memory structure in this example is configured to be restrained to opposites sides of the atrial septum.

FIG. 1 also shows an electronics enclosure 110 which comprises a sealed enclosure containing a battery and a circuit. In one example, the circuit can generate the stimulation energy to electrodes at the distal region of the lead(s) 101, 103 for pacing and/or for defibrillation. The circuit additionally or alternatively can sense and record the electrical activity from the electrode(s). The electronics enclosure device 110 may be a pacemaker, a defibrillator, a device that both paces and defibrillates, and/or a sensing or recording device.

Figure 2A:
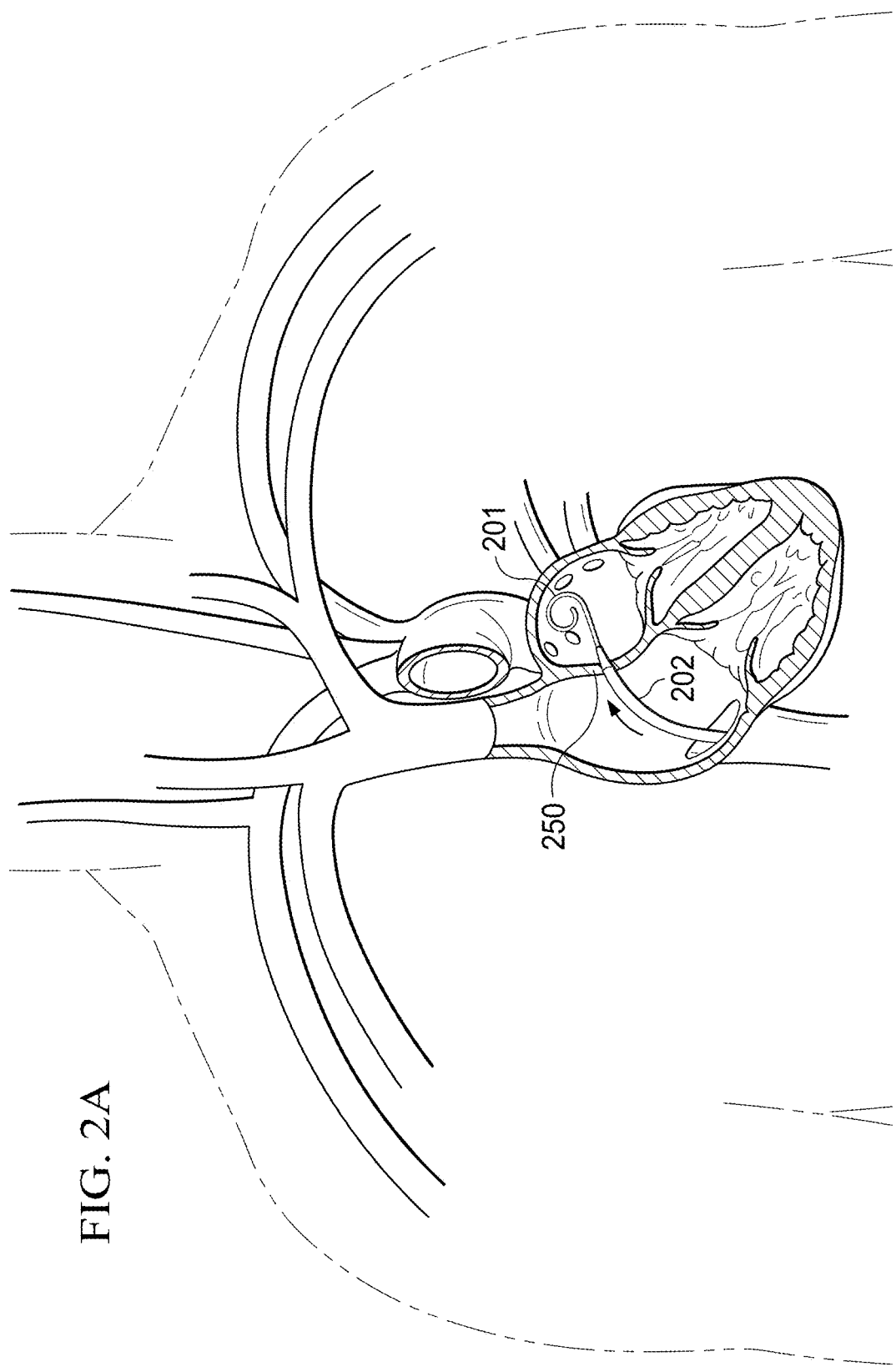
FIGS. 2A-2H illustrate a sequence of steps to attach the septal electrode during a surgical procedure.
Figure 2B:
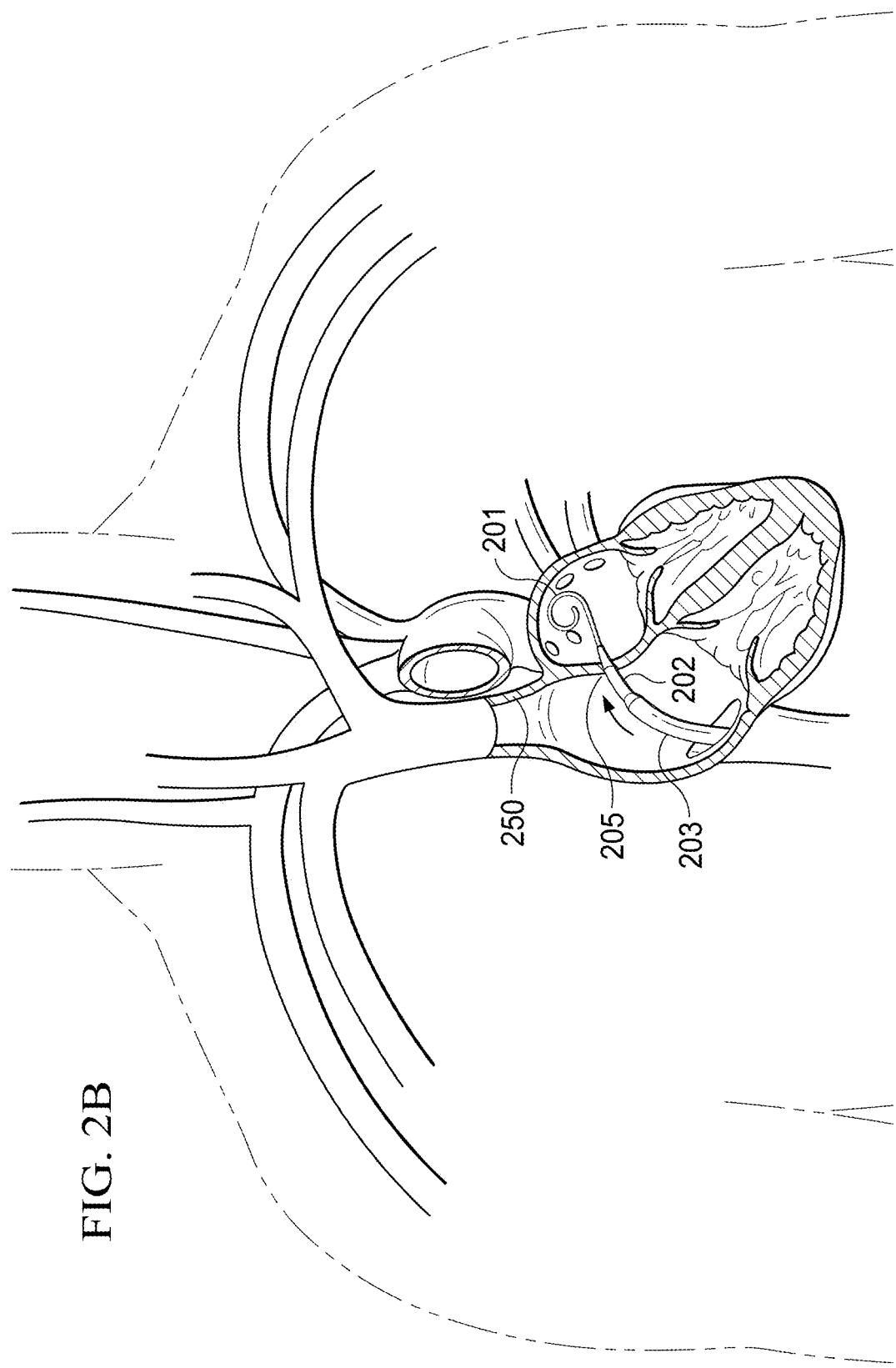
Figure 2C:
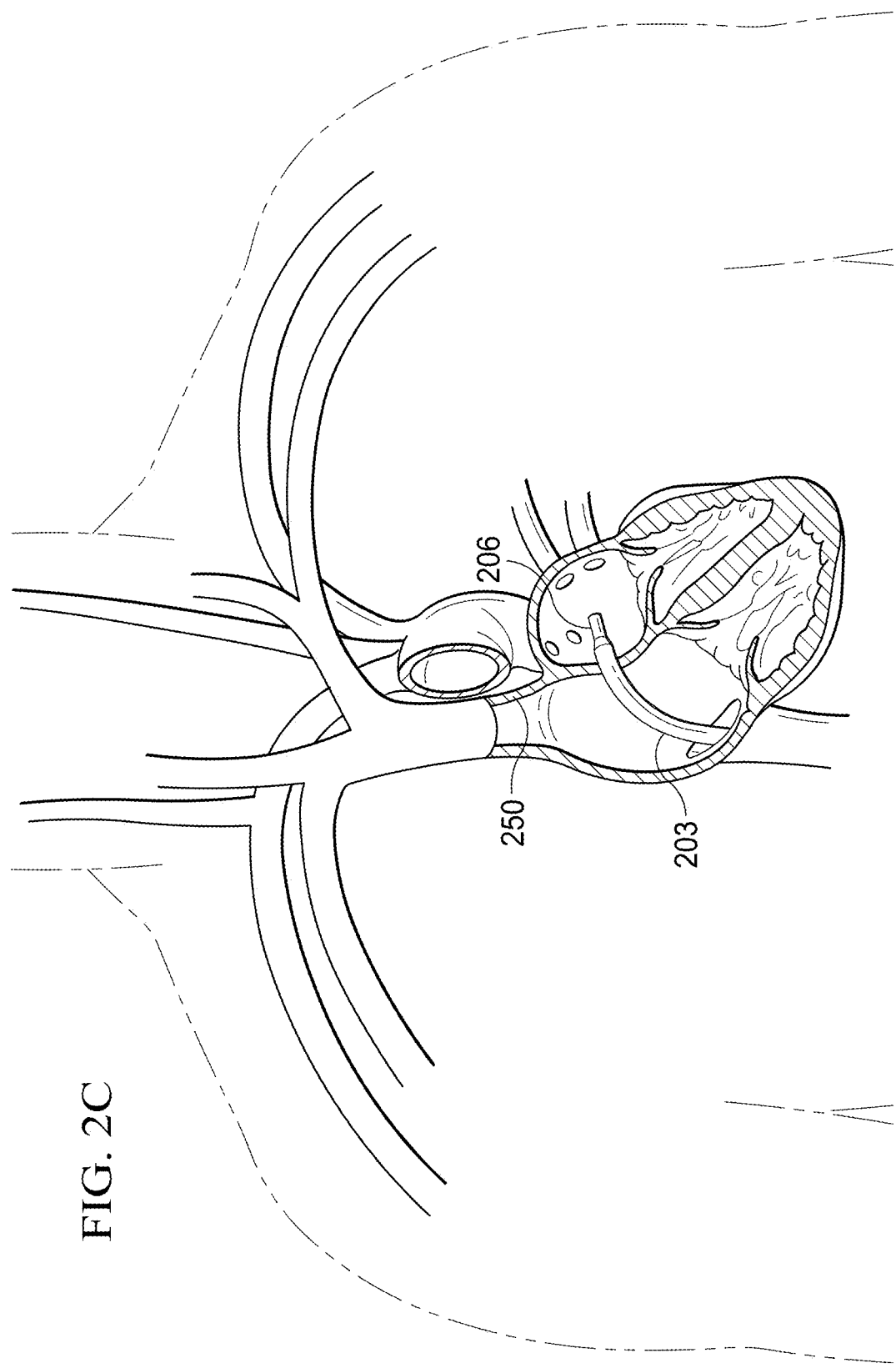
Figure 2D:
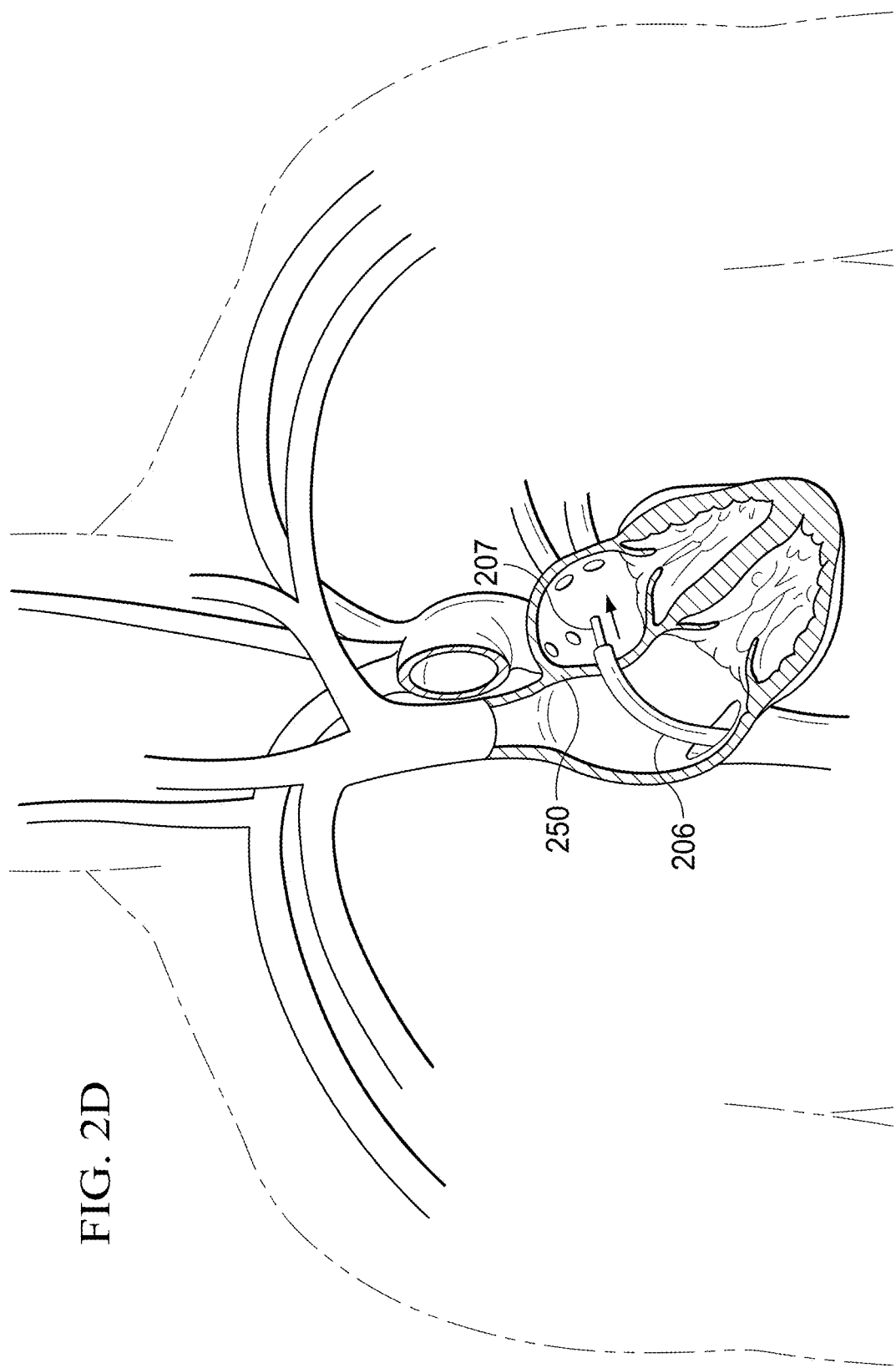
Figure 2E:
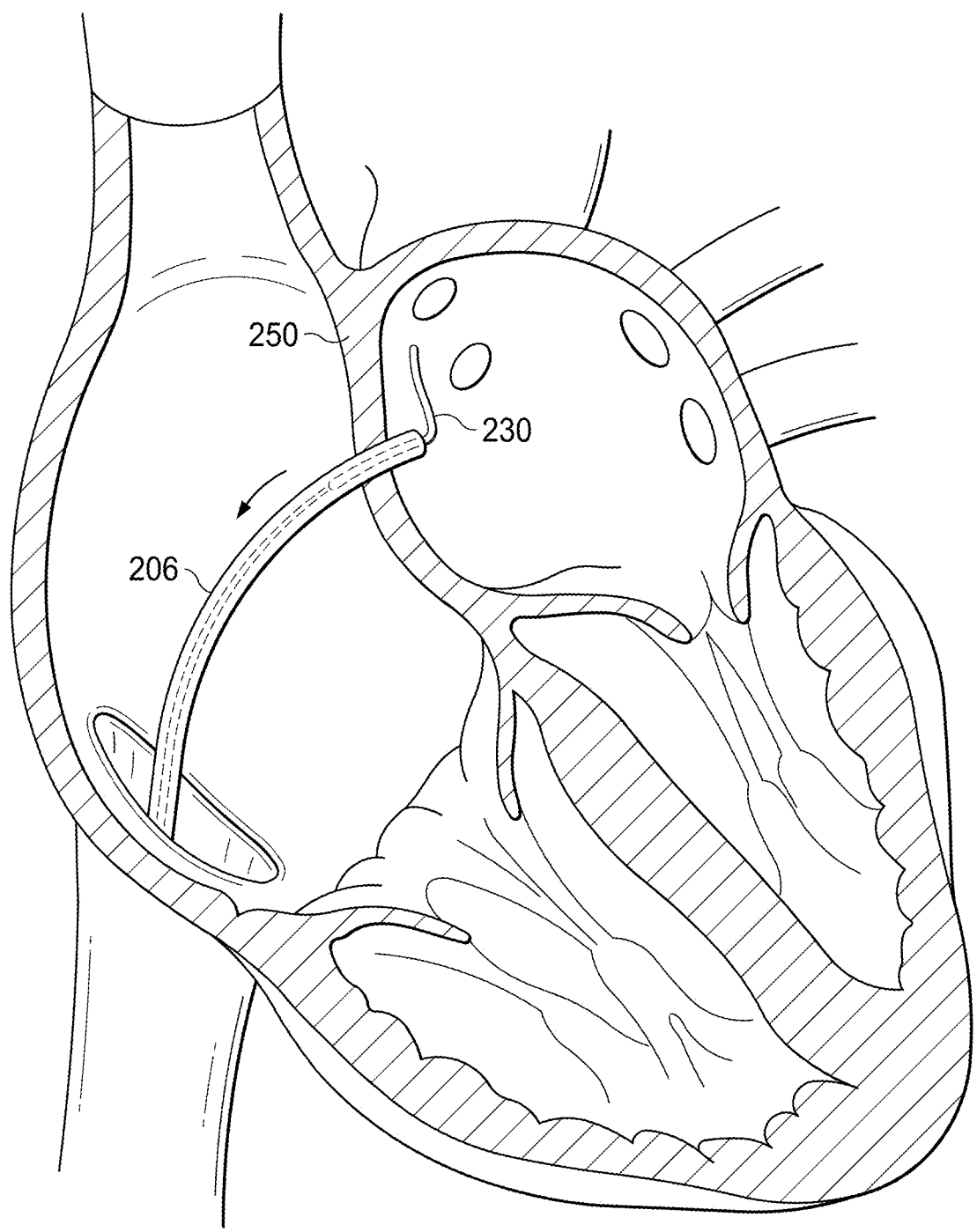

FIGS. 2A-2H illustrate a step-by-step procedure for attaching the leads to the heart. FIG. 2A depicts the initial transseptal puncture with a modified Seldinger technique. A guidewire 201 has been inserted via, for example, the groin and, through an obturator 202, into the left atrium. FIG. 2B depicts placing a transseptal sheath 203 through the transseptal puncture site 205 of the atrial septum 250. FIG. 2C depicts that the obturator 202 has been removed, and the transseptal sheath 203 remains in place with initial delivery of an anchor delivery sheath 206. The guidewire 201 has been removed. FIG. 2D depicts a septal electrode 230 (carrier or assembly) at the end of lead 103 exposed in the left atrium. The obturator 202 has been removed. FIG. 2E depicts the anchor delivery sheath 206 being retracted thereby exposing the septal electrode 230. The septal electrode 230 comprises a flexible elongate electrode. As can be seen, the distal region of the septal electrode 230 has a natural angled bend (approximately a right-angle bend) to it as shown.

Figure 2F:
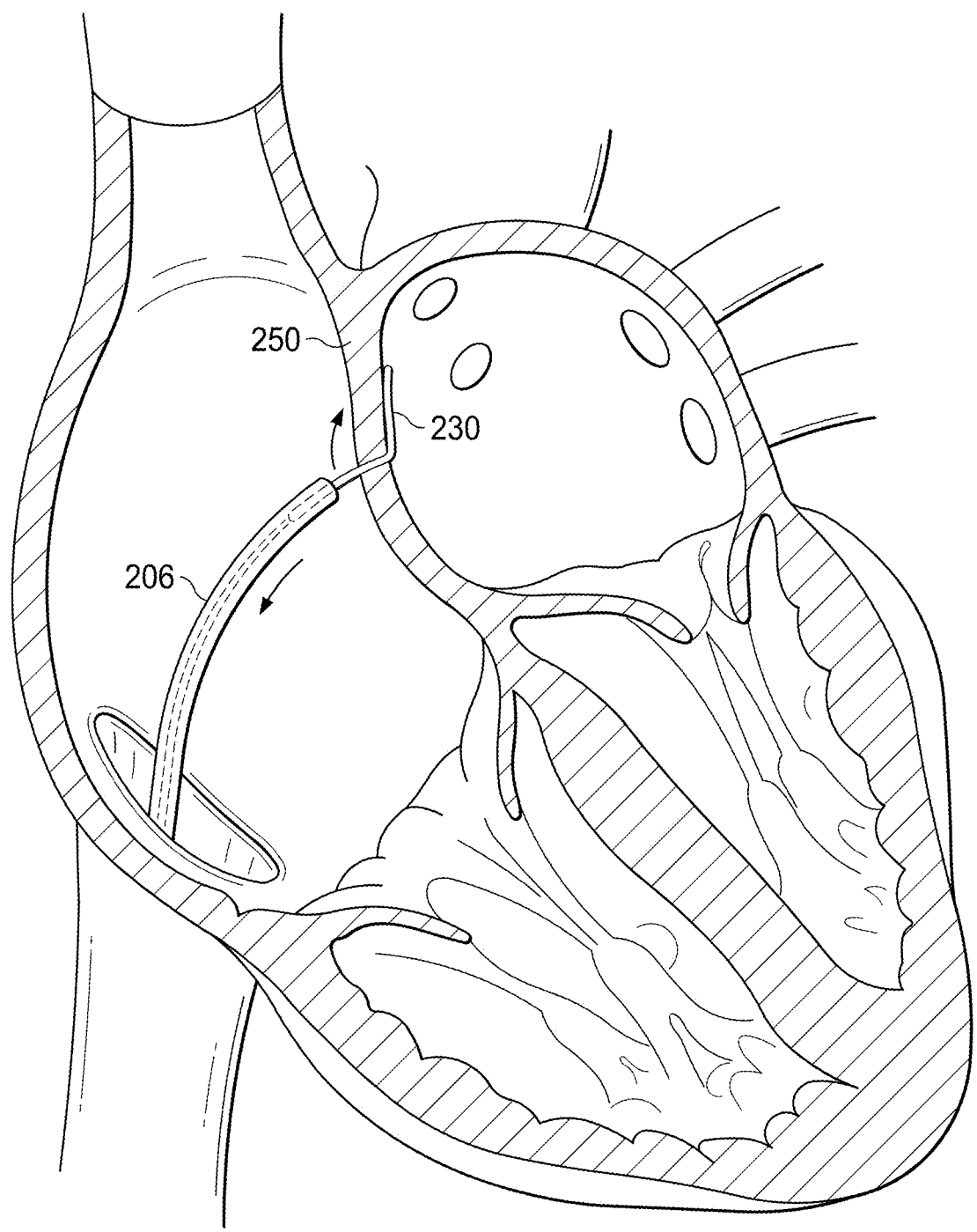

FIG. 2F depicts the further retraction of the anchor delivery sheath 206 and exposure of the septal electrode 230 against the atrial septum. The septal electrode 230 may comprise gold, nitinol or other suitable (e.g., inert and biocompatible) metal to transmit electricity to the heart. The septal electrode 230 maintains pressure against the atrial septum when deployed. The septal electrode 230 will maintain slight pressure on the septum to prevent movement of the device after it is deployed. As will be seen in the examples of FIG. 3A, the septal electrode 230 permits electrical current to flow to the septum 250 (and beyond) from an electronics enclosure.

Figure 2G:
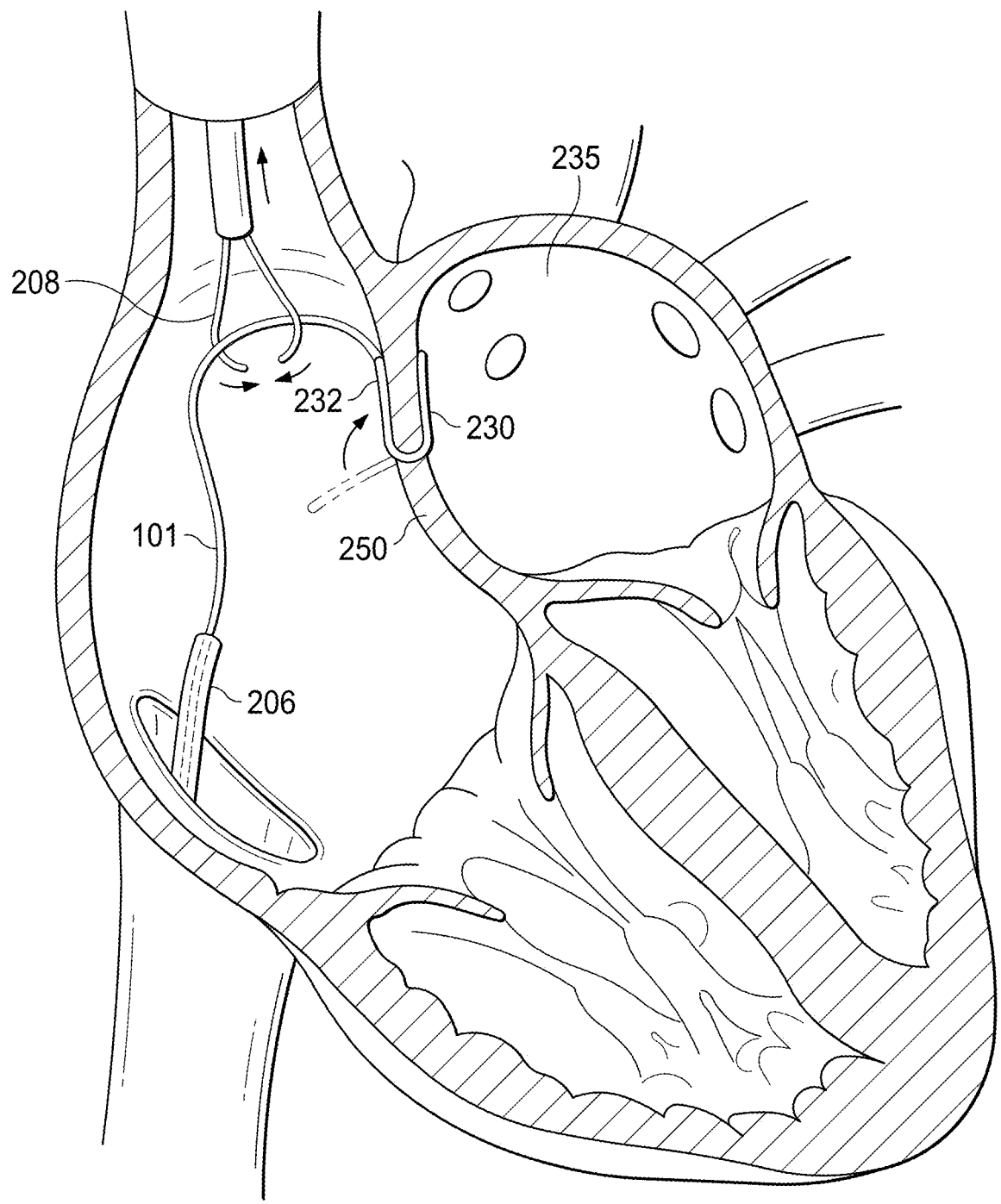

FIG. 2G depicts the septal electrode 230 fully deployed against the atrial septum 250. A snare device 208 is then depicted which allows the distal region of the lead to be moved from its insertion site (e.g., the groin) to the subclavian area or some other chest position at which the electronics enclosure is located. A portion 232 of the septal electrode 230 in the right atrium on the opposite side of the septum 250 from the portion of the septal electrode 230 in the left atrium is bent upward as shown using the snare device 208 thereby forming a U-shaped structure as shown. Because of the mechanical properties of the device (e.g., the memory shape structure), the wires will hug the endocardial surface. The septal electrode 230 may have configurations other than a U-shaped dip that perform the same or similar function as the U-shaped dip.

Figure 2H:
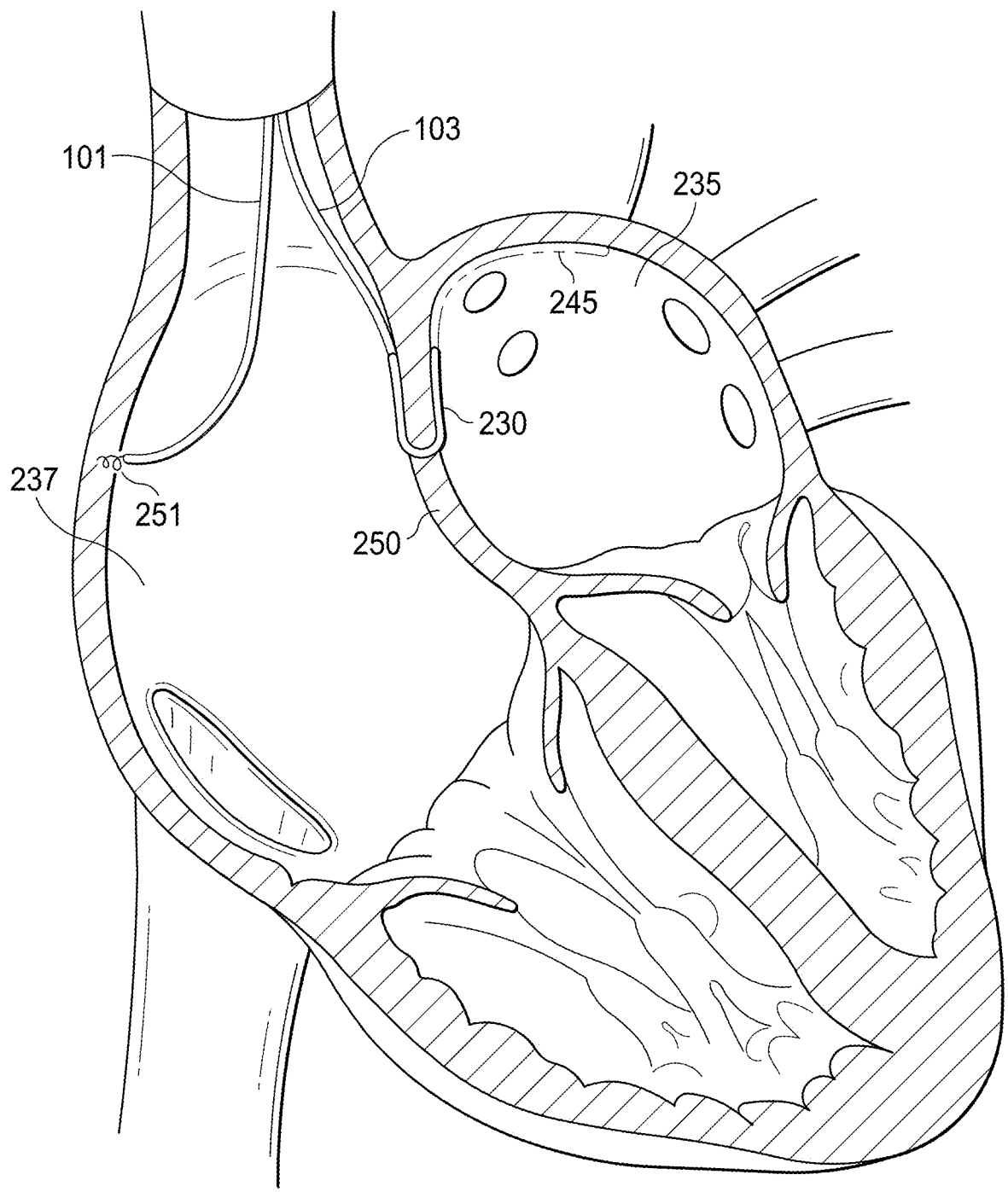

In other examples, the portion of the electrode pressed against the atrial septum in the left atrium may be longer than that shown in FIG. 2G or there be an additional array attached to the lead anchor 207 to increase the surface area along the atrial septum 250 and/or left atrium 235. For example, FIG. 2H depicts an extension 245L of the septal electrode 230 to increase the surface area for defibrillation of the left atria 235. Again, a shape memory metal (e.g., Nitinol) covering will hold the extensions tight against the atrial wall. Electrode 230 may be coated with a material such as gold to increase its conductivity. The curved wire can be made of nitinol or other shape memory material that can be straightened for implantation through a sheath into the patient—the curve shape can form inside the patient. The memory metal wire assembly can have the memory metal or similar material on the outside covering of the wire, as a part of the wire with insulation covering the wire or with any combination of a steroid, heparin coating or drug eluting coating. The device sits relatively flat against atrial wall (i.e., in continuous contact with the atrial wall such as the atrial septal wall) and eventually becomes strongly embedded in the cardiac tissue. This low profile discourages thrombus formation. The device has excellent electrical contact. The restraining device is held passively against the atrial septum. The restraining device easily attaching to the atrial septum with a low profile provides a safe route for deployment.

FIG. 2F also depicts both leads 101 and 103 exiting in the left subclavian area or other site on the chest. An electrode 251 is shown at the distal end of lead 101 and anchored into the right atrium 237.

FIGS. 2I-2M are illustrations of illustrative alternative embodiments of electrical contacts that may be used in conjunction with the septal electrode 230. FIG. 2I shows the septal electrode 230 with extension electrodes 245R and 245L (collectively 245) that extend from the septal electrode 230 in the respective right atrium 235 and left atrium 237, and are configured to maintain contact with the endocardium (i.e., inner walls) of the left and right atriums 235 and 237, respectively. The extension electrodes 245 may have reflectively identical shapes. Alternatively, the extensions electrodes 245 may have different shapes. However, in both cases, the extension electrodes 245 the exposed metal of the extension electrodes 245 may passively maintain contact with the walls of the left and right atria 235 and 237, respectively, by having a curved shape and formed of a shaped memory material that causes the extension electrodes 245 to press against the walls of the respective left and right atriums 235 and 237. As previously described, the extension electrodes 245 may be electrically connected to the septal electrode 230 or otherwise extend therefrom. The extension electrodes 245 may have the same or different lengths, and the lengths may be set based on an appropriate amount of resistance and electrical current transfer. Such lengths may be predetermined or may be established during installation if the septal electrode 230 is configured to enable length of the extension electrodes 245 to be adjustable prior to or during implantation. That is, the septal electrode 230 may allow for the extension electrodes 245 to be slidably connected to or detachable from/reattachable to the septal electrode 230, thereby allowing for an operator to alter length of the extension electrodes 245. In an alternative embodiment, devices including a septal electrode 230 with different length extension electrodes 245 may be available. Alternatively, an operator may cut the extension electrode(s) 245 depending on desired size and performance (e.g., smaller hearts may be suited with shorter extension electrodes 245). In an embodiment, the lead 103 may extend through and form an extension electrode 245 on a distal side of the lead and opposite side from where the lead 103 connects with the septal electrode 230, as additional shown and described herein.

With regard to FIG. 2I-A, in an embodiment, one or both of the extension electrodes 245 may include protrusions 246a-246n (collectively 246), such as in the shape of hooks, sawtooths, barbs, needles, or otherwise, that may be used to help maintain contact of the extension electrodes 245 with the walls of the left and right atria 235 and 237.

With regard to FIG. 2I-B, in an embodiment, rather than the extension electrodes (e.g., conductive metal), such as electrode 245L, being fully exposed, the electrodes may be partially exposed and partially insulated. For example, insulation 247 may extend on a side opposite the wall while an exposed electrode may be on the side of the wall, thereby the exposed electrode 245L may press against and extend along the endocardium of the wall. The insulation 247 may be impregnated polymer to inhibit thrombosis formation, for example. By maintaining insulation on the opposite side of the wall, reduced risk of a thrombus forming on the extension electrodes 245 may result. As previously described, a coating that reduces the risk of clotting may be applied to the insulation to avoid thrombus formation on the electrodes and wires. And, because an extended length of exposed electrode contacts the endocardium, it may be possible to provide lower energy and/or different signaling to the heart for pace or other treatments, thereby enabling a patient to perform treatments on themselves without risk of conventional treatments that typically requires a patient to be within a medical facility.

Figure 2J:
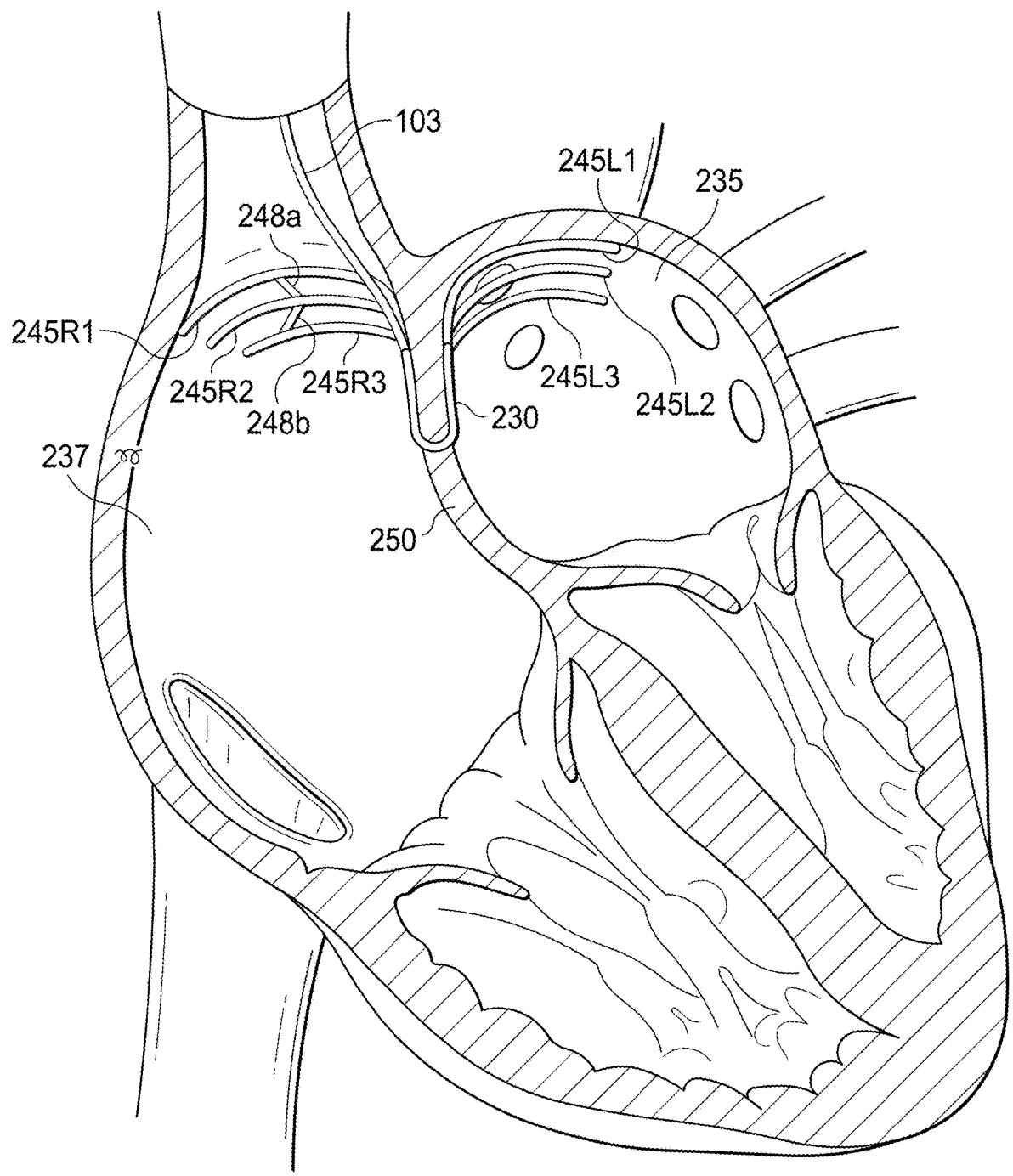

With regard to FIG. 2J, an illustration of an alternative configuration of extension electrodes is shown to include a plurality of extension electrodes 245L1-245L3 (collectively 245L) positioned in the left atrium 235 and extension electrodes 245R1-245R3 (collectively 245R) in the right atrium 237. In this embodiment, there are three extension electrodes 245L and three extension electrodes 245R in each of the left and right atria 235 and 237. It should be understood, however, that alternative numbers, such as two or more extension electrodes, may be positioned in each of the left and right atria 235 and 237. Moreover, it should be understood that a different number of extension electrodes may be positioned in each of the left and right atria 235 and 237. As with the extension electrodes 245 of FIG. 2I, the extension electrodes 245L and 245R may be electrically connected or otherwise extend from the septal electrode 230. The thicknesses and configuration of the extension electrodes 245L and 245R may be such that the collective electrodes 245L and 245R may be deployable via a transseptal sheath, as previously shown with regard to FIG. 2C, for example. The extension electrodes 245 may be part of a lead (e.g., lead 103) or independent of a lead. Lengths of the respective extension electrodes 245 may vary depending on patient, treatment, and use of the extension electrodes 245.

The extension electrodes 245L and 245R may have the same or similar physical characteristics as previously described with regard to the extension electrodes 245 of FIG. 2I, for example (e.g., gold, nitinol, inert and biocompatible metal, preformed shape, etc.). The extension electrodes 245L and 245R may further have optional connection features 248a and 248b (collectively 248) between adjacent electrodes (e.g., 245R1-245R2, 245R2-245R3) so that the adjacent electrodes have a maximum restrained spacing between one another. Although not shown, the extension electrodes 245L in the left atrium 235 may also have connection features that are the same or similar to the connection features 248. In an embodiment, the connection features 248 may be electrical conductors or non-electrical conductors and may also be formed of the same or similar material as the extension electrodes 245. Moreover, the connection features 248 may be shaped to assist with maintaining the extension electrodes 245L and 245R against the walls of the left and right atria 235 and 237. It should be understood that the configuration may be leadless, as further provided herein.

Figure 2K:
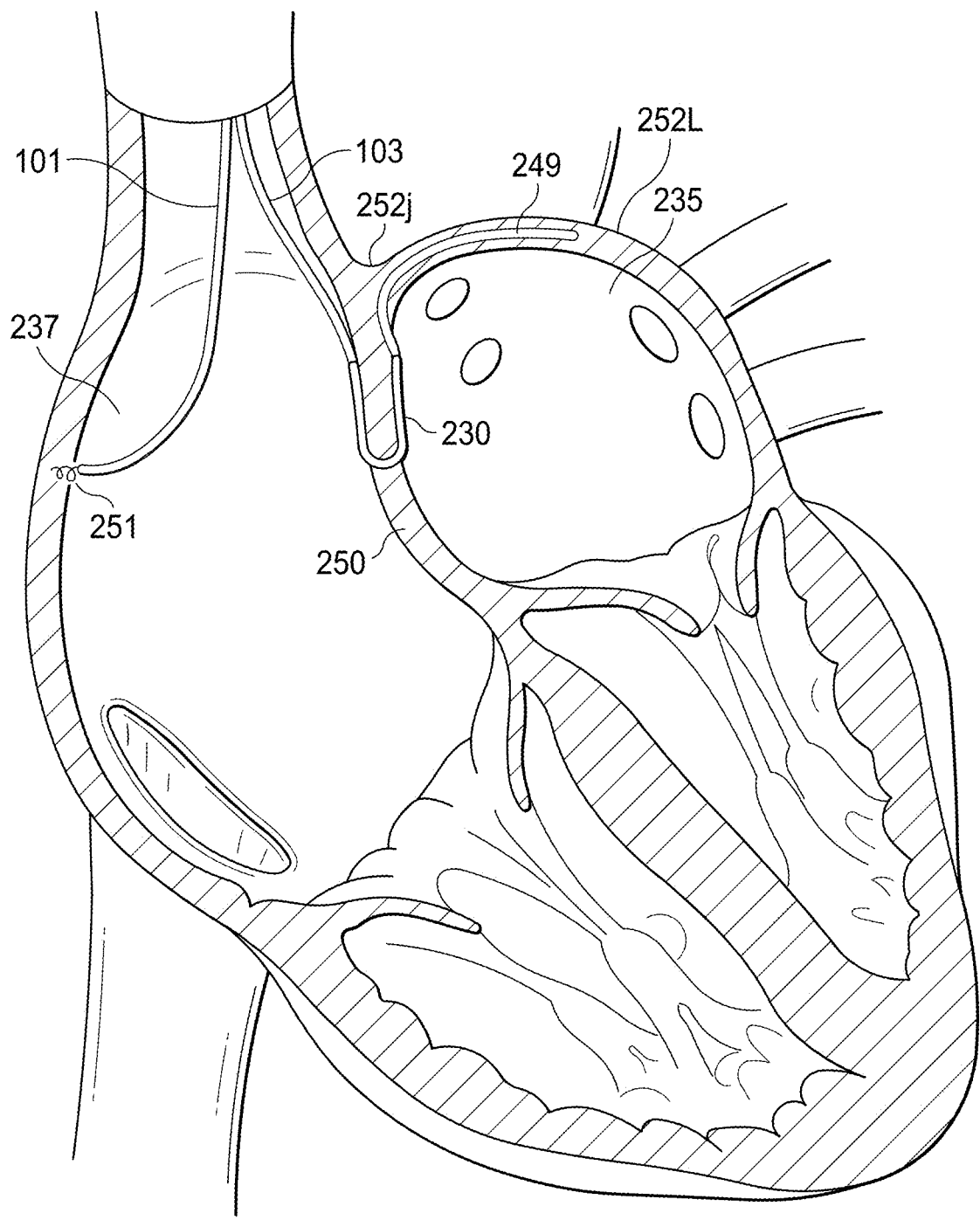

With regard to FIG. 2K, an illustration of an alternative illustrative embodiment of extension electrode(s) is shown, In this embodiment, an extension electrode 249 is shown to be intramural (i.e., be extended through and remain within a wall 252L). As with the extension electrode 245L of FIG. 2I, the extension electrode 249 may be electrically connected to or otherwise extend from the septal electrode 230 that is held to the atrial septum 250. Both leads 101 and 103 are shown to be exiting in the left subclavian area or other site on the chest. An electrode 251 is shown at the distal end of lead 101 and anchored into the right atrium 237. It should be understood that the lead 101 and electrode 251 may not be utilized if an extension electrode, such as extension electrode 245R, is disposed in the right atrium 237, as provided in FIG. 2I.

In an embodiment, the extension electrode 249 may be inserted into the wall 252L at a wall junction 252j between the left and right atria 235 and 237, as the wall junction 252j is slightly thicker than the wall 252L, thereby being slightly safer than entering directly into wall 252L. In one embodiment, the extension electrode 249 may extend through the epicardium of the wall 252L, but remain inside the pericardium of the wall, and the pericardium may hold the extension electrode 249 against the epicardium to apply electrical signals applied to the extension electrode 294 to the epicardium of the left atrium 235. In an embodiment, the extension electrode 249 may be fully non-insulated. Alternatively, an insulator may extend along the extension electrode 249 to an approximate distance of where the wall 252L extends from the wall junction 252j, thereby limiting electrical signals to the left atrium 235. Alternative configurations of the extension electrode 249 and insulation thereon are possible.

Figures 1, 2L:
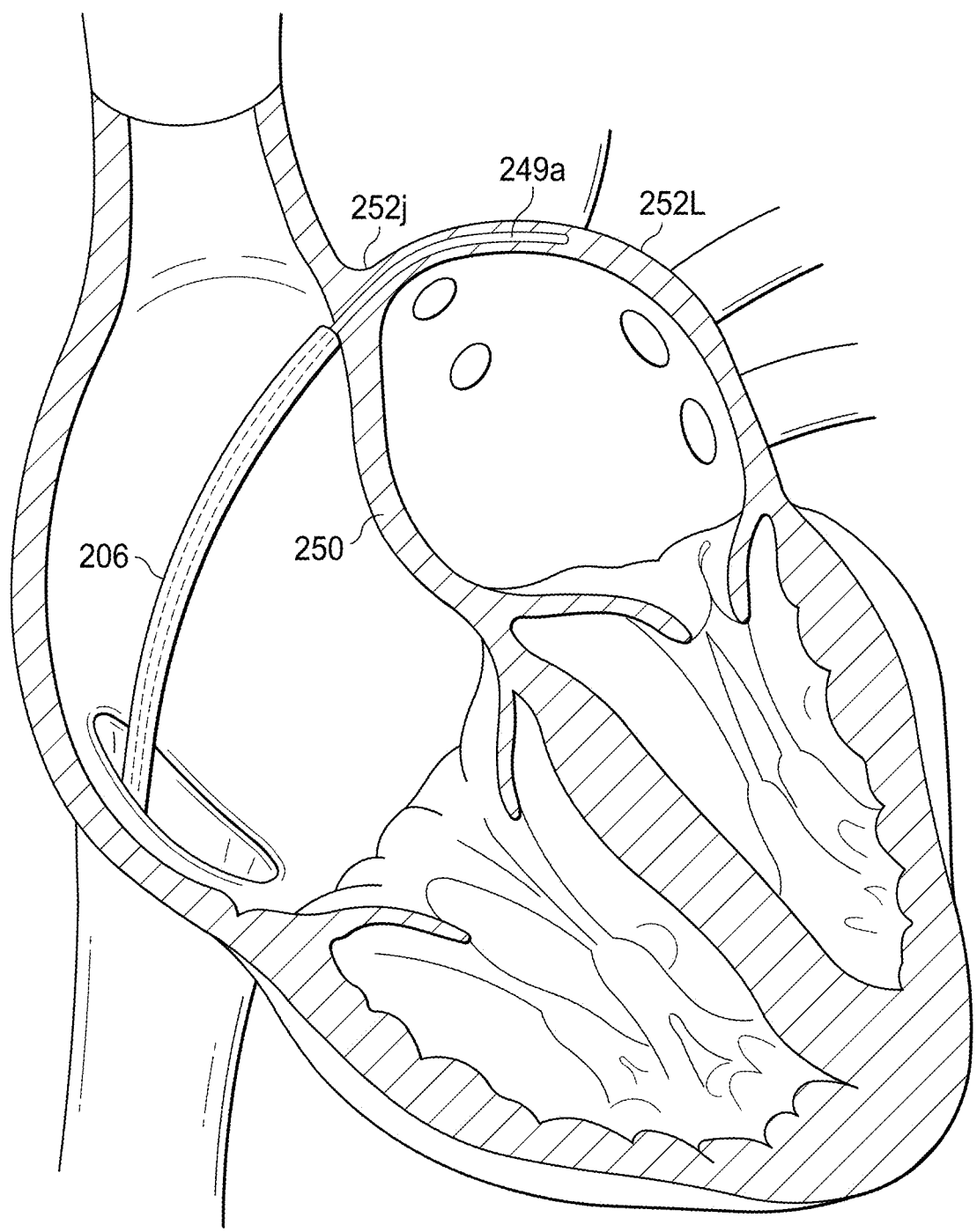
Figures 2, 2L:
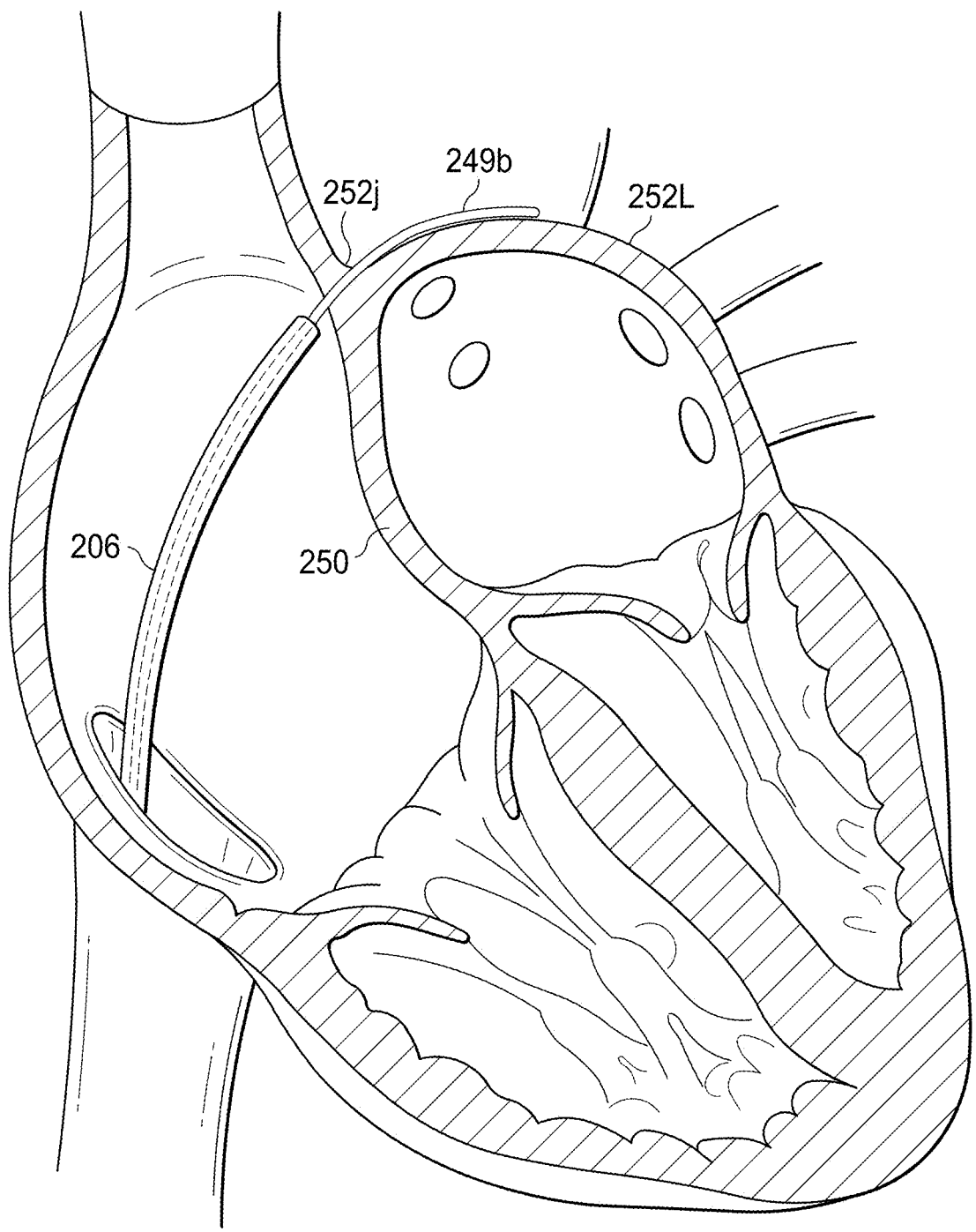
Figure 2M:
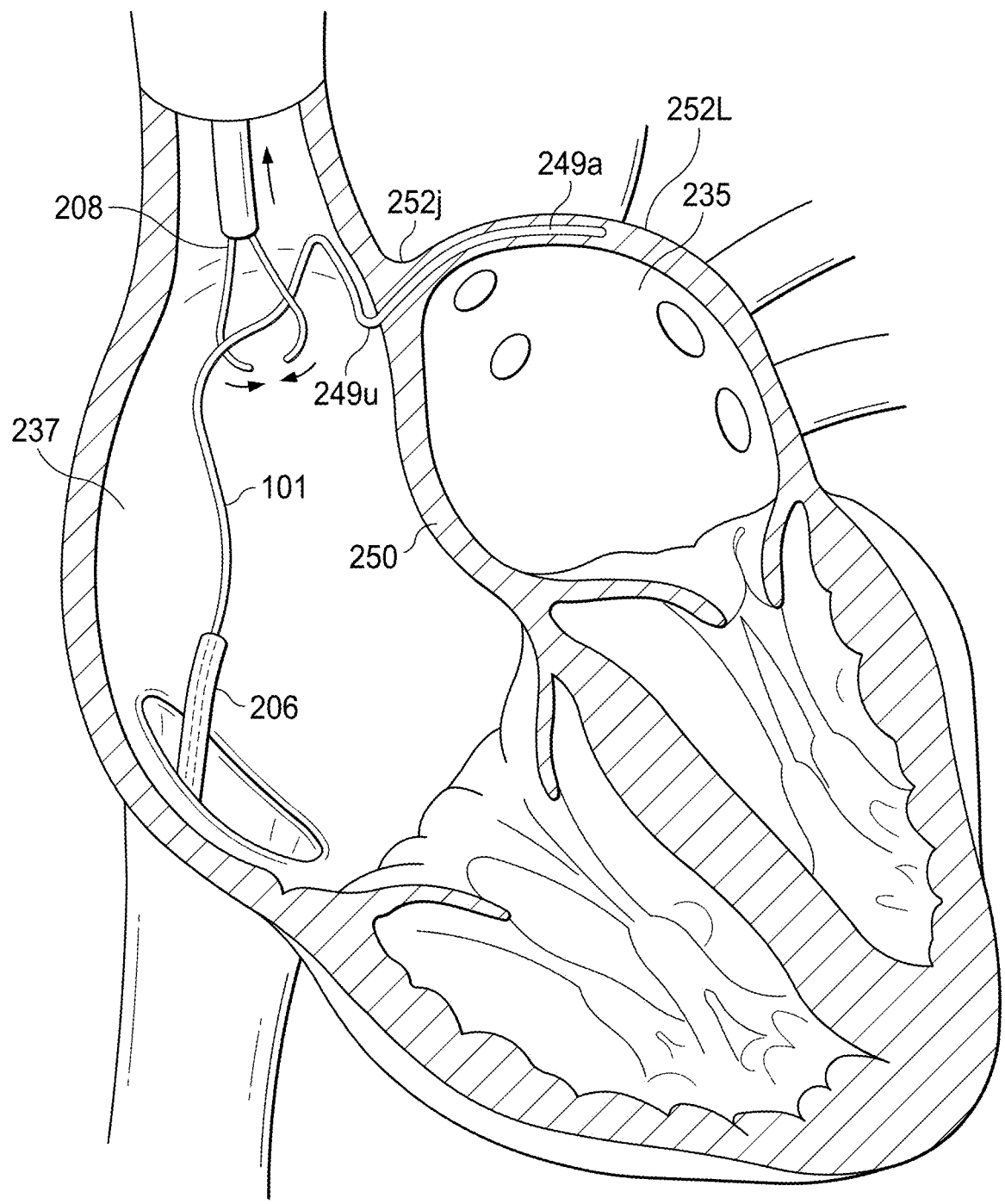

With regard to FIGS. 2L-1, 2L-2, and 2M, an illustrative sub-process for inserting an alternative configuration of an extension electrode 249a using the anchor delivery sheath 206 of FIG. 2E is shown. However, rather than entering through a center portion of the septum 250, the extension electrode 249a may enter through the wall junction 252j at the top of the septum 250 from the right atrium 237, thereby simplifying the insertion process into the wall 252L of the left atrium 235. As shown in FIG. 2M, the extension electrode 249a may have a u-curve 249u that forms a curved bend to cause the extension electrode 249a to extend along a wall of the right atrium 237. The u-curve 249*u* may be preset such that when the extension electrode 249*a* is released from the sheath, the u-curve 249*u* is automatically shaped. In an embodiment, to secure the extension electrode 249*a* in the wall of the left atrium 235, a number of different techniques may be utilized, including a septal electrode that may be curved or appear as a straight stud with a retention feature that secures to the septum 250, post, suture, or any other mechanism that may assist in maintaining the maintaining the position of the extension electrode 249*a*. In another embodiment, the extension electrode 249 may include a protrusion anywhere along the length or at the u-curve 249*u* that may prevent the extension electrode 249*a* from backing out of the wall 252L and wall junction 252*j*.

In the event that the lead 101 is to extend to a device, then other procedural processes as previously described may be utilized. In an embodiment, to support the u-curve 249*u* and curve of the extension electrode 249*a* that extends intramural through the wall 252L of the left atrium 235, those portions (i.e., u-curve 249*u* and extension electrode 249*a*) may be formed of material with shape memory, as previously described. Because the extension electrode 249*a* extends intramural, there is minimal or no ability for any clotting to occur in the left atrium 235 because the extension electrode 249*a* does not enter the left atrium 235. Moreover, if the extension electrode 249*a* is secured to the wall of the right atrium 237 without having to pierce the septum 250, other procedural and operational risks may be reduced.

With regard to FIG. 2L-2, another illustrative sub-process for inserting an alternative configuration of an extension electrode 249*b* using the anchor delivery sheath 206 of FIG. 2E is shown. In this process, rather than the extension electrode 249*b* extending into the myocardium and being intramural, the extension electrode 249*b* may extend through the wall junction 252*j* and along the epicardium of the wall 252L. Extending through the wall junction 252*j* that is thicker than the thinner walls or atrial septum 250, a reduced risk of tear or bleeding is possible. Although only one extension electrode 249*b* is shown, it should be understood that multiple extension electrodes 249*b* may be utilized and extend along the epicardium of the wall 252L. In an embodiment, to limit the ability for bleeding to occur through a hole formed by the extension electrode 249*b* from the right atrium to outside the wall 252L, a hemostatic agent or tissue adhesive may be used to seal the opening through which the extension electrode 249*b* extends. In an embodiment, the hemostatic agent may be disposed or pre-applied on the extension electrode 249*b* such that the hemostatic agent is automatically applied when inserted into the wall junction 252*j*, thereby limiting or preventing blood to flow through the wall junction 252*j* external the wall 252L. Other mechanical, chemical, and/or biological techniques may be utilized to limit or prevent blood flow from the opening created by the extension electrode 249*b*.

Figure 2N:
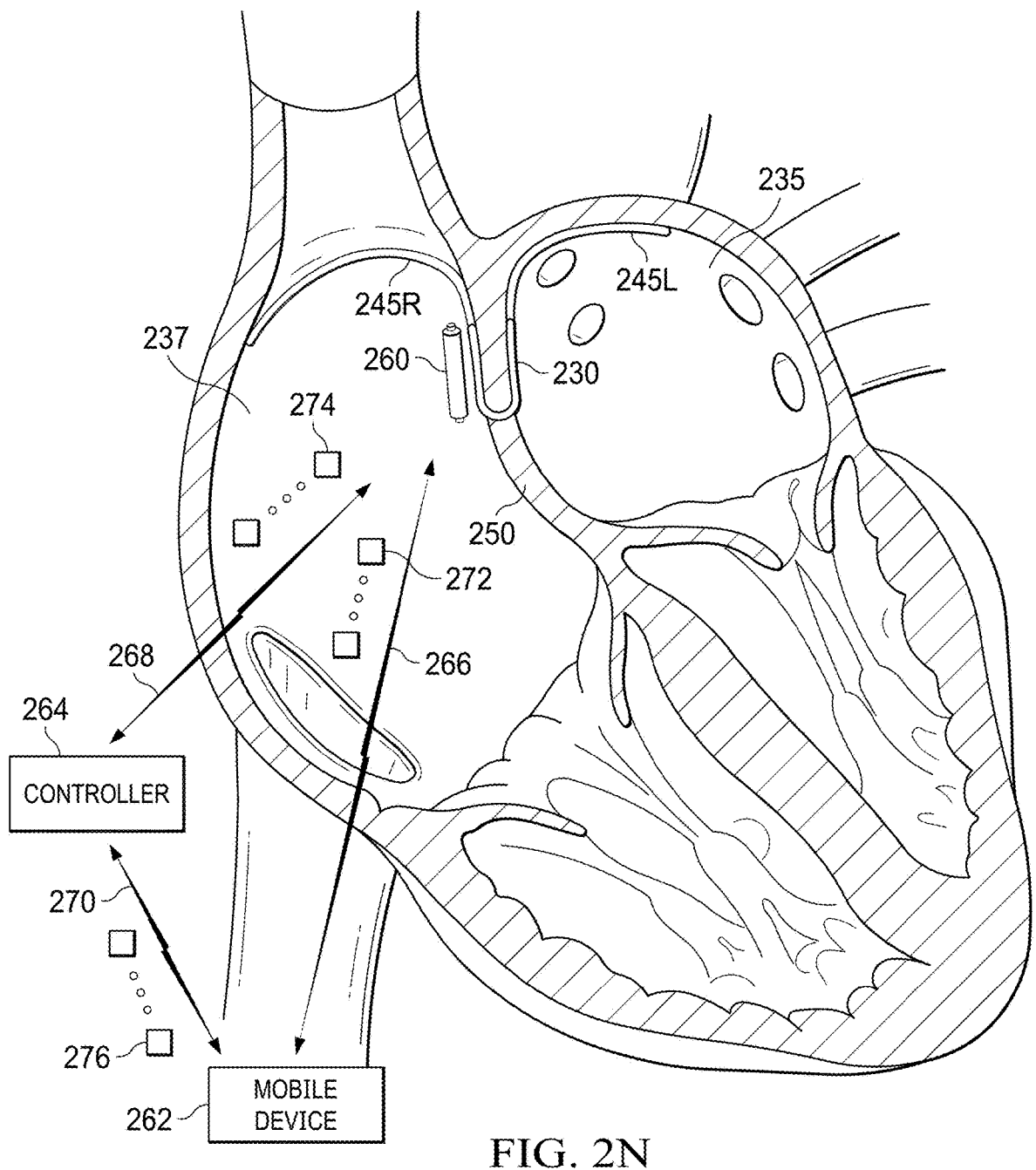
FIGS. 2N and 2O are embodiments of illustrative leadless pacemakers that are attached to illustrative septal electrodes having electrical contacts extending therefrom.

FIG. 2N is an illustration of an illustrative leadless pacemaker 260 that is attached to an illustrative septal electrode 230 having electrical electrodes 245R and 245L (collectively 245) extending therefrom. In this embodiment, the leadless pacemaker 260 may be elongated and extend along the septal electrode 230, and may be in electrical contact therewith such that any electrical signals produced by the leadless pacemaker 260, those signals may be transferred to the septal electrode 230, which causes the electrical signals to extend along the extension electrodes 245. It should be understood that if only the extension electrode 245L extends from the septal electrode 230, then the electrical signals may be extended into the left atrium 235 and along the endocardium of the wall of the left atrium 235. The septal electrode 230 and leadless pacemaker 260 may be connected to one another in a variety of different ways, but is to be physically connected in a manner that has no adverse interaction to a patient's heart or health. In an embodiment, a housing of the leadless pacemaker 260 may have the septal electrode 230 being integrated with one another (e.g., monolithic single piece of material) during production. Alternatively, the two elements 230 and 260 may be connected to one another using attachment elements, such as screws, bolts, clips, structural linking elements, etc. Moreover, because the leadless pacemaker 260 does not need to have electrodes extend from the heart to an implanted device (e.g., controller), then no leads are necessary to extend from the leadless pacemaker 260 or septal electrode 230.

As further shown, a mobile device 262, such as a smartphone or other portable electronic device, and controller 264, which may also be an electronic device that may be attached to or wirelessly in communication with the mobile device 262. Wireless communications channels 266, 268, and 270 may enable wireless communications between the leadless pacemaker 260 and mobile device 262, leadless pacemaker 260 and controller 264, and mobile device 262 and controller 264. Data 272, 274, and 276 may be communicated via the respective communications channels 266, 268, and 270 and between the respective devices configured to communicate via the communications channels 266, 268, and 270. The communications channels 266, 268, and 270 may be local communications channels using local wireless communications protocols (e.g., Bluetooth®, WiFi®, or otherwise). Each of the mobile device 262 and controller 264 may include a processor, memory, and wireless communications devices to support operations of the leadless pacemaker 260. The processors of the mobile device 262 and controller 264 may be configured to process and send data and/or control signals between one another and with the leadless pacemaker 260.

In operation, the leadless pacemaker 260 may sense signals and/or operations of the heart (e.g., heartbeat rate in either or both of the left atrium 235 and right atrium 237) via data signals 272 via the communications channel 266 to the mobile device 262. The mobile device 262 may be configured to receive and display data (e.g., graphics, text, text and graphics) for a user of the mobile device 262. In an embodiment, a mobile app (not shown) may be configured to receive and process the data signals communicated by the leadless pacemaker 260. The mobile app may further be configured to cause the mobile device 262 to communicate with the controller 264 via the communications path 270 by sending data signals 276 that may, in turn, cause the controller 264 executing software on a processor, to send control signals to the leadless pacemaker 260 for controlling pace, for example, of one or both the left and right atria 235 and 237, respectively. It should be understood that the same or similar configuration may be utilized in the left and right ventricles of the heart.

The leadless apparatus could wirelessly communicate with a phone or other device that may deliver specific electrical energy in specific configurations that could terminate the firing of an abnormal atrial focus or foci with or without a defibrillation. This leadless apparatus could also be configured in the leadless device itself. The recording and storing of information from the atrial walls or other areas of the heart may be stored and analyzed in the device itself or the information could be sent to other devices, which may analyze the information to guide further therapy.

Because the extension electrodes 245 are disposed within the respective left and right atria 235 and 237, the same or different pace or other signals may be applied as is conventionally applied. In other words, because the extension electrodes 245 are maintained against the endocardium, lower power signals (e.g., less than 1 joule) may be applied by the leadless pacemaker to cause the heart to be properly paced or otherwise treated. It should be understood that similar low amounts of energy may be applied to the extension electrodes extending from the septal electrode 230 if a lead is used to connect thereto (see, for example, FIG. 2I). It should be understood that the leadless pacemaker 260 may be configured with an energy source sufficient to operate for many years. Alternatively, sufficient wireless energy may be transferred to the leadless pacemaker 260 from the controller 264, for example, to enable the wireless pacemaker 260 to perform necessary functions (e.g., applying pacing signals).

Because of the low amount of power to be applied to the heart because of the configuration of the extension electrode(s) 245, a patient may self-administer treatment via the mobile device 262 and/or controller 264. Software executed by the mobile device 262 may enable the user to monitor his or her heart using a mobile app, which may notify the user of a rhythmic abnormality, for example. The patient may sit or lay down before self-administering treatment, thereby being safe. Because of the lower energy, the patient may feel no or minimal discomfort. If the software is configured to ramp up electrical signaling and receive feedback after each signaling is applied, for example, the process may perform treatments with minimal interaction by the patient or risk to the patient.

Figure 2O:
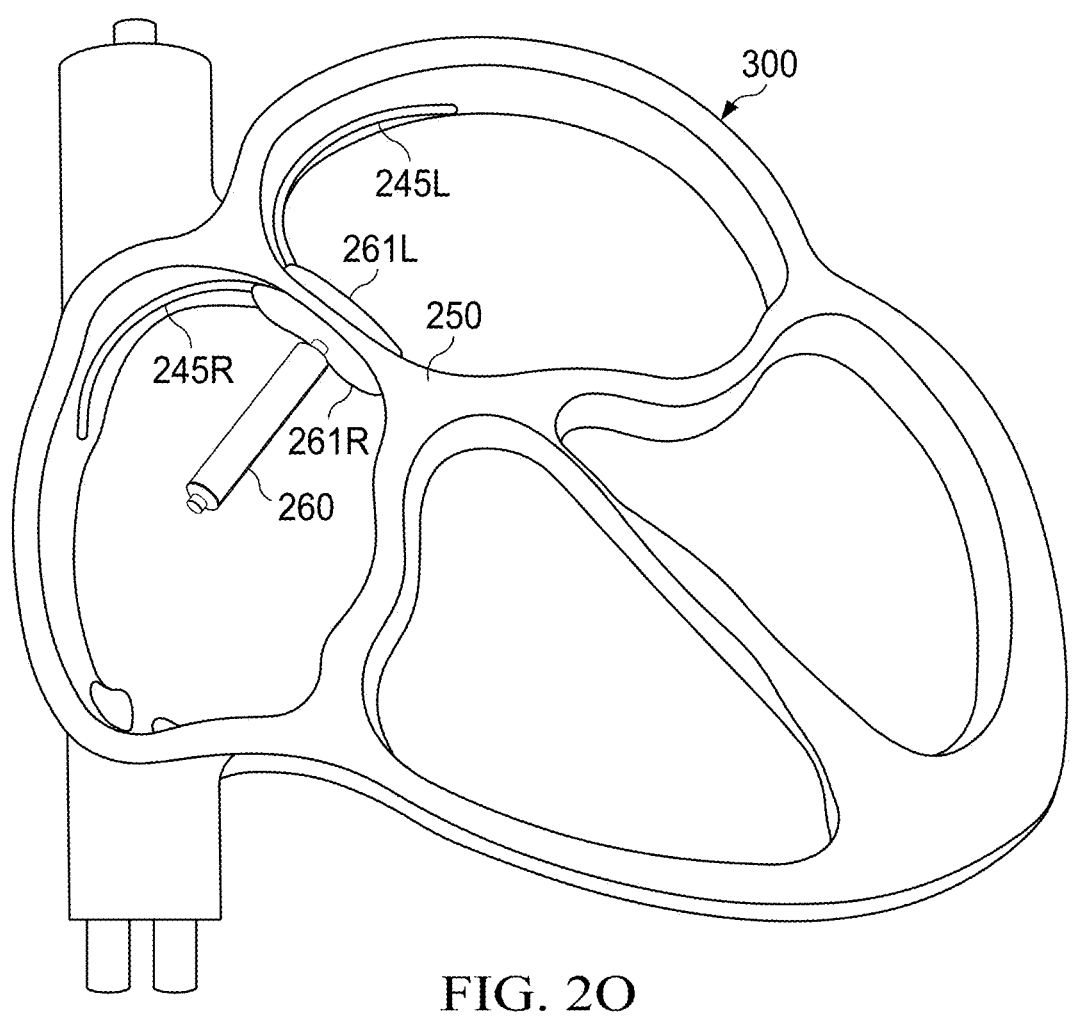

With regard to FIG. 2O, the leadless pacemaker 260 may be connected to the atrial septum 250 using an alternative septal electrode element 261R, which connects to a septal electrode element 261L to form a septal electrode 261. The septal electrode 261 may be the same or similar to the septal electrode 400 (FIG. 3C) and provide the same or similar electrical and mechanical functions as the septal electrode 400, as further described herein. In this embodiment, the leadless pacemaker 260 may extend perpendicularly from the septal electrode element 261R, but may also be configured to extend along a wall or be integrated with the septal electrode element 261R. Still yet, the leadless pacemaker 260 may be connected to or be integrated with the septal electrode element 261L. In either case, an electrical connection is made between the leadless pacemaker 260 and septal electrode element(s) 261R and 261L so as to provide the various electrical stimulation support to the heart of the patient. Rather than simply applying electrical connection from the septal electrode 261, extension electrodes 245R and 245L may extend along the endocardium of the left and right atria 235 and 237. It should be understood that alternative configurations of the extension electrodes 245 may be utilized, as further described herein. In an embodiment, the septal electrode elements 261 may be configured without the ability to make electrical connections with the endocardium at the atrial septum, but rather simply support the extension electrodes 245 and enable electrical communications between the leadless pacemaker 260 and extension electrodes 245.

Figure 3A:
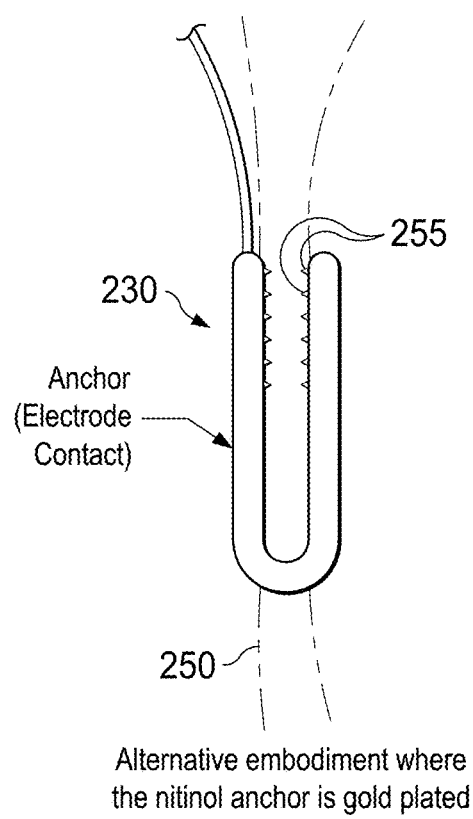
FIG. 3A shows a close-up view of one example of the septal electrode which includes protrusions to help hold the septal electrode in place against the septum.
Figure 3B:
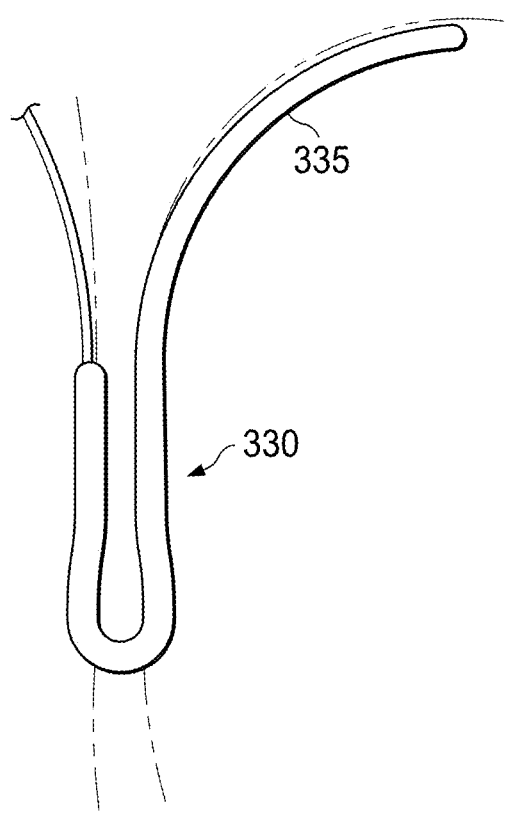
FIG. 3B shows another example of a septal electrode with extension further into the left atrium, again with the wires and electrode flush against the endocardium.
Figure 3C:
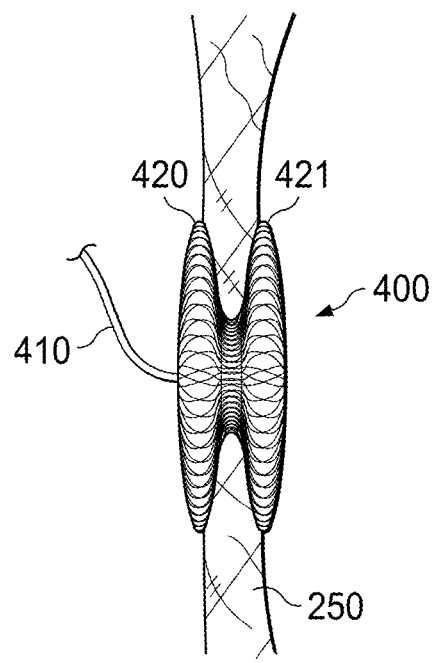
FIG. 3C shows yet another example of a septal electrode with deployable wings held in place by the device against the atrial wall.

FIGS. 3A-3C depict examples of devices that specifically allow for atrial defibrillation with two electrodes. One of the electrodes is placed in the right atrium (e.g., electrode 251 shown in FIG. 2H), but other locations are possible as well such as the right ventricle, left ventricle, or coronary sinus. The other electrode comprises the septal electrode 230 that sits along the atrial septum. FIG. 3A depicts a septal electrode 230 hugging both sides of the atrial septum 250. Protrusions 255 (e.g., teeth) extend towards and slightly into the septum 250 and allow secure positioning along the septal wall to help anchor the septal electrode 230 in place on opposite sides of the septum 250.

FIG. 3B is similar to FIG. 2H and depicts a septal electrode 330 hugging the atrial septum with a left atrial (could also be right) extension 335 for additional surface area (compared to septal electrode 230 in FIG. 3A) for defibrillation. Protrusions 255 may be included in this embodiment as well to help hold septal electrode 330 and its extension 335 in place.

FIG. 3C depicts an alternate septal electrode 400 which covers both sides of the atrial septum 250. Septal electrode 400 comprises a plug having an electrode array. The plug can have electrode properties, or the plug may incorporate electrode(s) with sufficient conductivity, such as gold plating. The extra electrode(s) can be weaved into the plug, or can be a circular electrode on one or both sides of the device, or can be more than one electrode in circles about the circumference or radius or in between the plug. The extra electrode is attached to a wire 410 which exits the heart in the same manner as the device in FIGS. 3A and 3B. Opposing wings 420 and 430 can be deployed (e.g., fan out) to anchor the device against the septum 250 as shown.

Figure 3D:
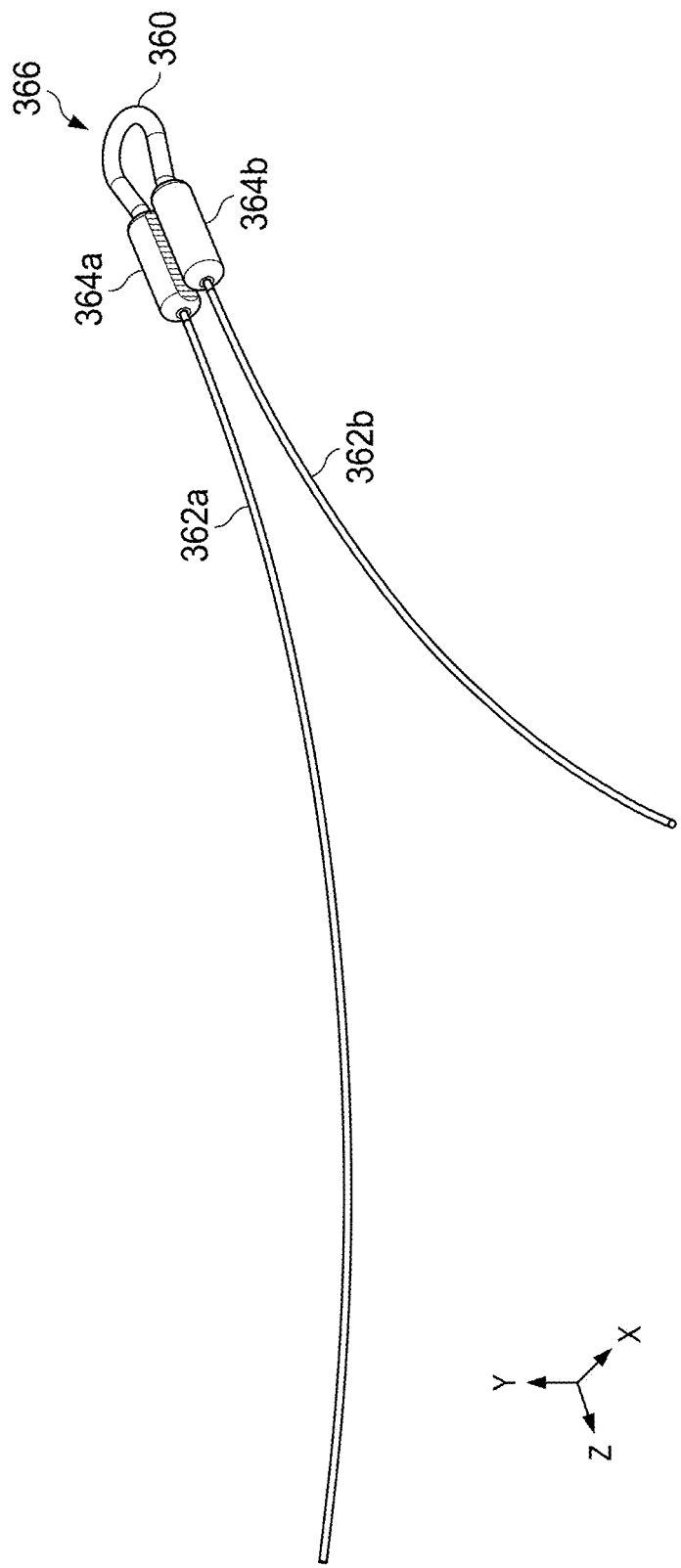
FIGS. 3D-3F are illustrations of an illustrative septal electrode to which extension electrodes extend and are supported by sleeves.
Figure 3E:
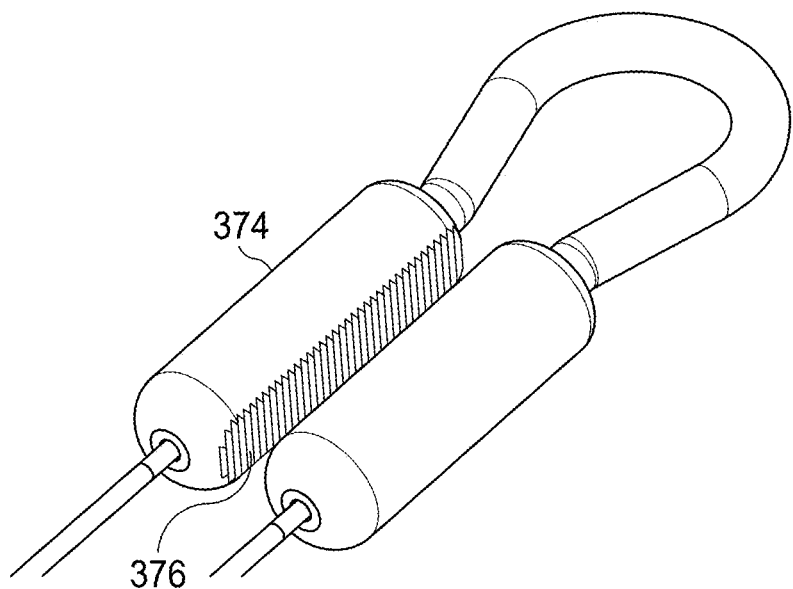
Figure 3F:
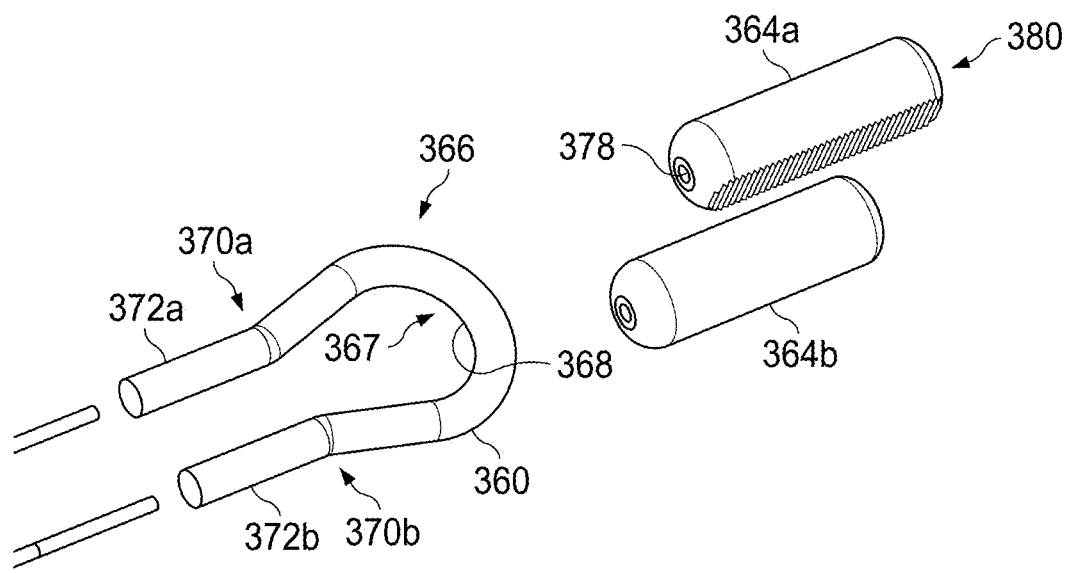

With regard to FIGS. 3D-3F, illustrations of an illustrative septal electrode 360 to which extension electrodes 362a and 362b (collectively 362) extend and are supported by sleeves 364a and 364b (collectively 364) are shown. In this embodiment, the septal electrode 360 is curved at an end region 366 to form a concave shape 367 along an inner radius surface 368 of the septal electrode 360 and opposing convex shapes 370a and 370b (collectively 370) at an intersection between the end region 366 and projection members 372a and 372b (collectively 372). The projection members 372 may extend parallel or substantially parallel (i.e., within a few degrees as limited by manufacturing processes) with one another.

The overall shape of the septal electrode 360 may provide for more inward pressure being applied to a septum 250 by the sleeves 364 that extend over the projection members 372 than the end region 366. The sleeves 364 may be tubular and be identical in size and shape with one another. In an embodiment, the sleeves 364 may include a rounded external surface radially along the sleeves 364 and have flat surfaces 376 with a textured surface, such as a triangular, saw tooth, protrusions, indentations, hooked, and/or any other textured or geometric-shaped surface that causes the flat surfaces 376 to secure against the septum 250, thereby reducing slippage of the septal electrode 360 relative to the septum 250. As shown, the sleeves 364 include openings 368 and 380, where the opening 378 may be sized to interference fit the extension electrodes 362 and the openings 380 may be configured to interference fit the projection members 372. The sleeves 374 may be non-conductive. The septal electrode 360 may be electrically conductive, and include a non-conductive coating or sleeve. Other configurations of the septal electrode 360 may be utilized. If conductive, electrical signals applied to one of the extension electrodes 362 (e.g., extension electrode 362a) by a pacemaker or other electrical power source (e.g., defibrillator) may flow through the septal electrode 360 to the other of the extension electrodes 362 (e.g., electrical conductors 362b), thereby applying electrical signals to the wall 252L of the left atria 235, where the extension electrode 362b may be in direct contact with one or more of the endocardium, myocardium, and/or epicardium of the wall 352L of the left atria 235.

Figure 4A:
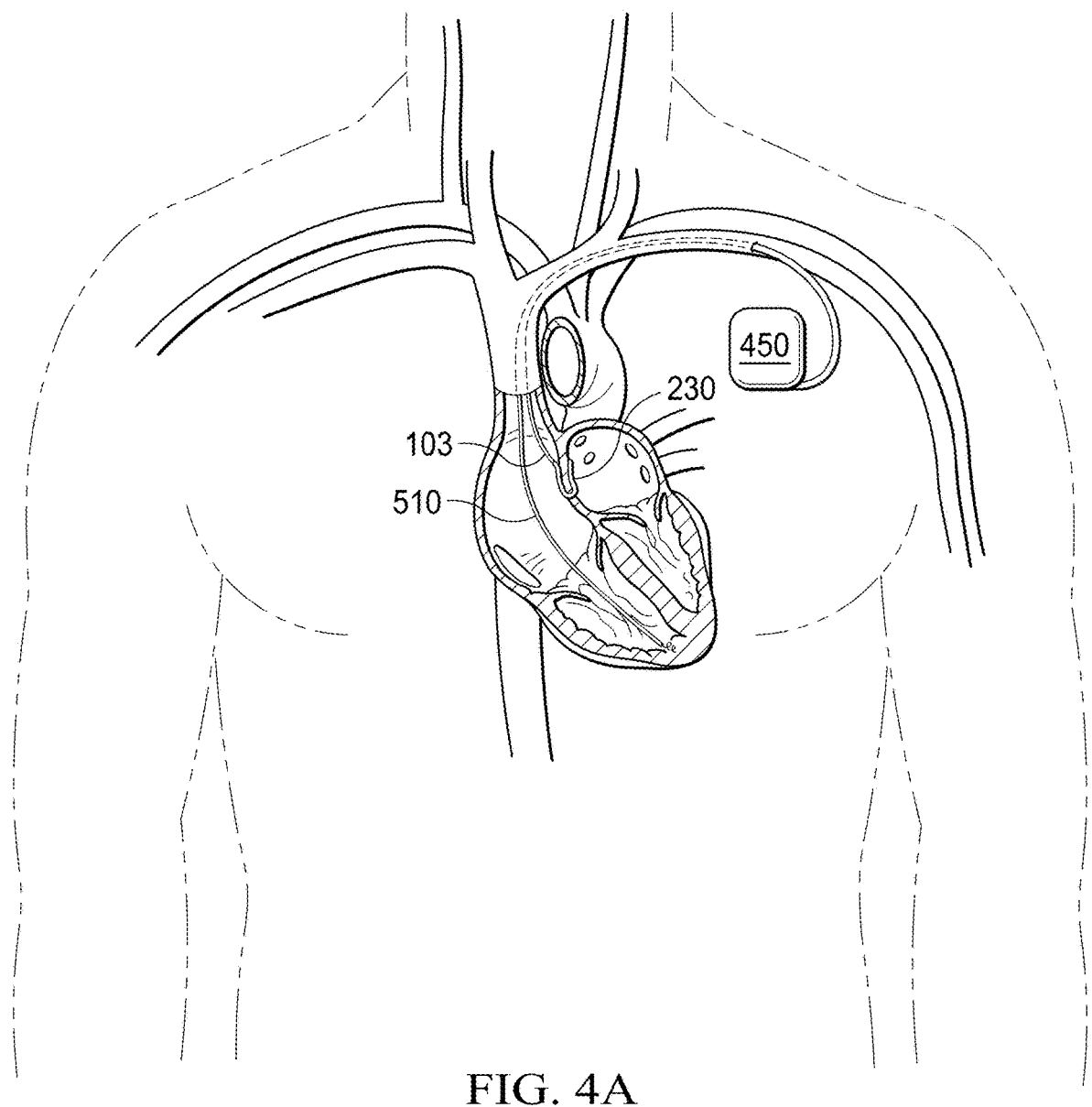
FIG. 4A shows an example of an implantable medical device with a septal electrode on one lead and another electrode on a second lead into the right ventricle.
Figure 4B:
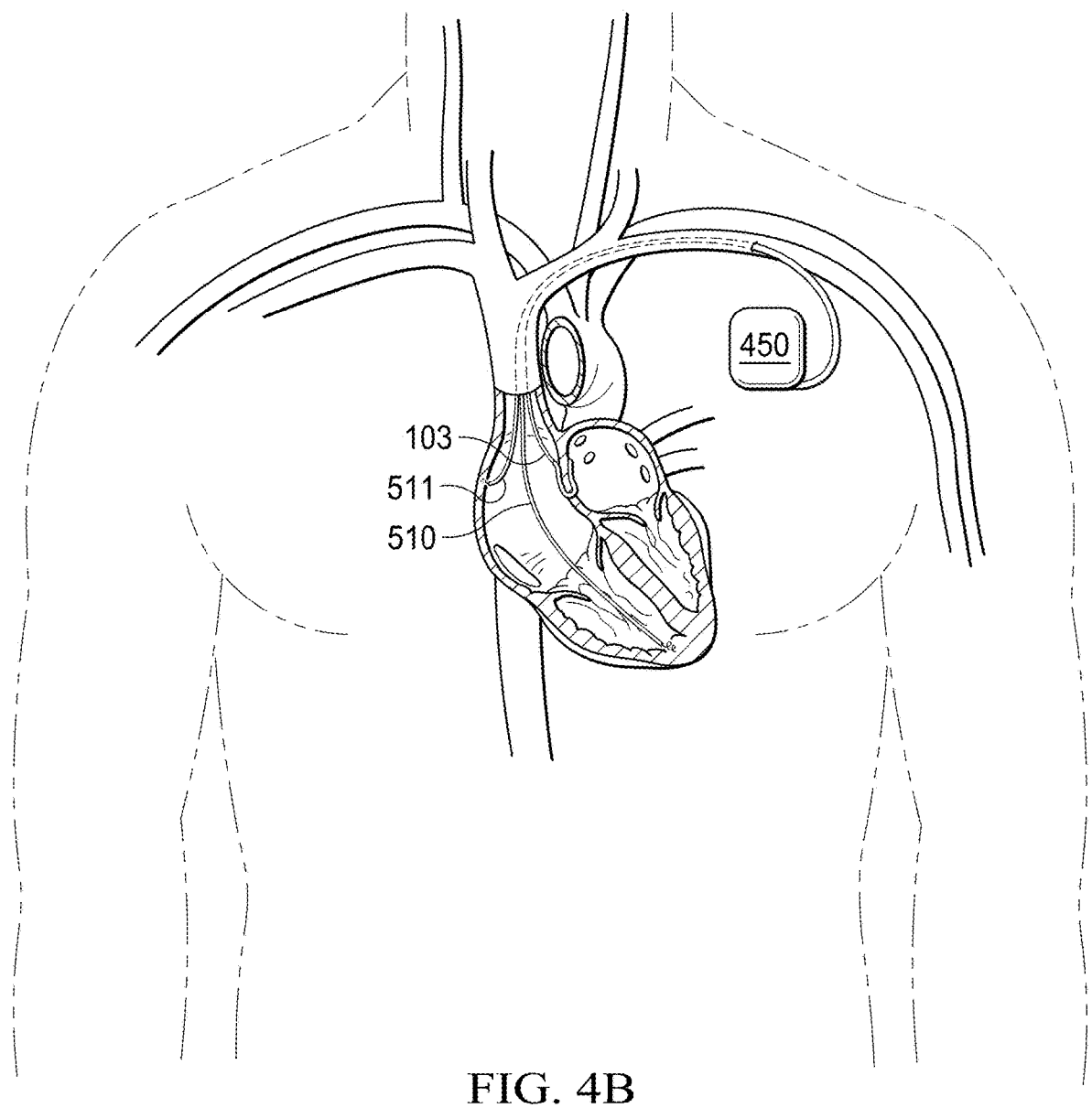
FIG. 4B shows an example of an implantable medical device with a septal electrode on one lead, and two additional leads anchored into the right atrium and right ventricle.

FIG. 4A shows an atrial defibrillator (or pacemaker, sensor, or recording device) implanted in a person with the septal electrode 230 of lead 103 connected to a battery-powered electronics enclosure 450 (similar to electronics enclosure 110 described above) and attached to the atrial septum and another lead 510 provided into and anchored to the right ventricle. The electronics enclosure comprises a sealed enclosure, a battery contained therein, and a circuit to generate electrical stimulation signals to be provided to the electrodes at the distal ends of the leads. FIG. 4B shows the atrial defibrillator implanted in a person with the septal electrode 230 of lead 103 attached to the atrial septum, a second lead 510 provided into and anchored to the right ventricle, and a third lead 511 anchored into the right atrium.

Figure 5:
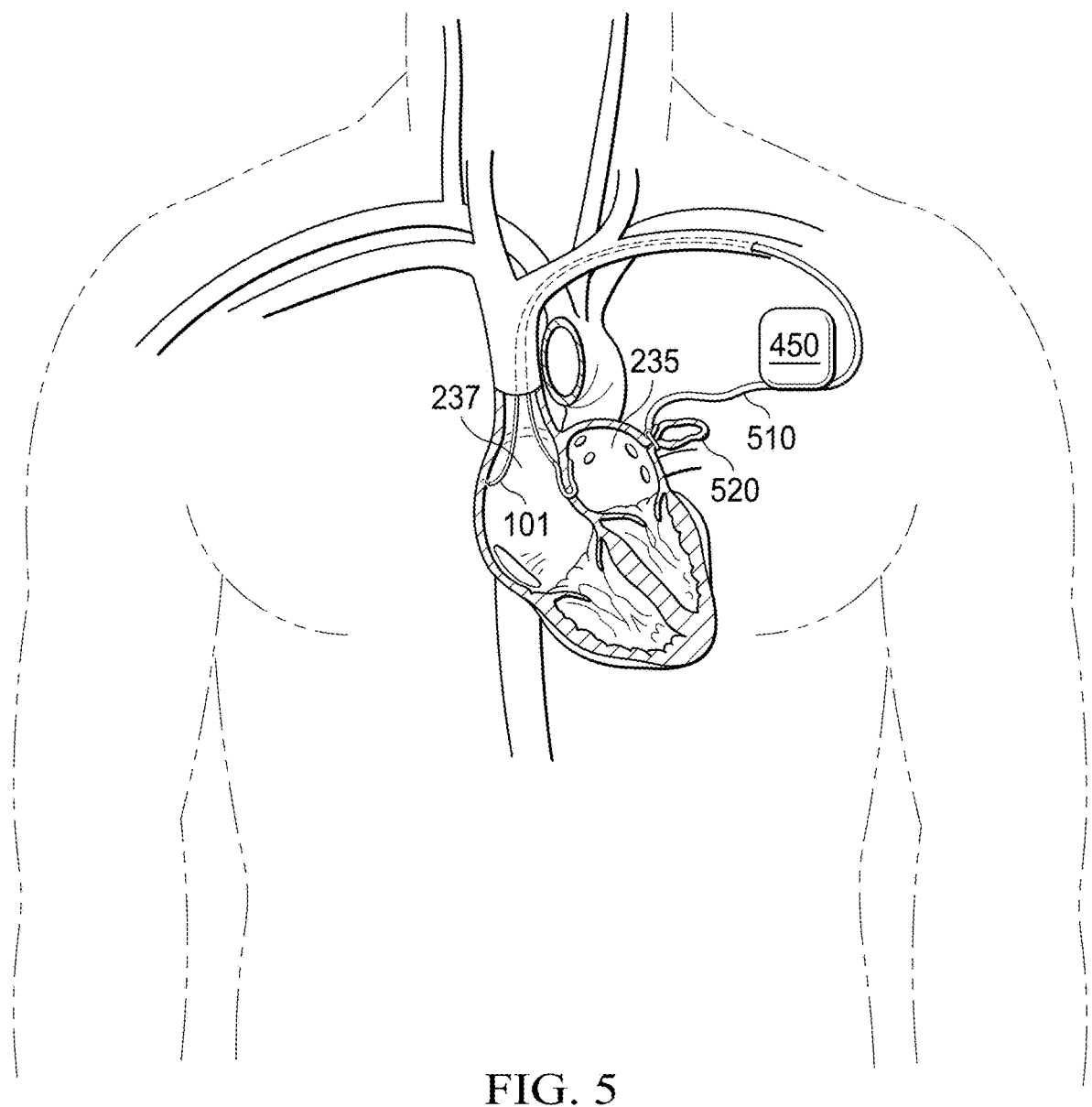
FIG. 5 illustrates another embodiment in which an electrode is part of an atrial appendage closure device in which the closure device is external to the atrial appendage, which keeps the wire of the device tight against the atrial wall.

FIGS. 5-7 illustrate an embodiment in which an atrial electrode is included in a device that occludes an orifice of the atrial appendage from outside the heart. FIG. 5 depicts an arrangement of the leads of a defibrillator with one atrial lead 101 placed in the right atrium 237. A second atrial lead 510 is placed in or about the atrial appendage 520 of the left atrium 235 and is attached to an atrial appendage closure device that is used to dose the orifice between the left atrium 235 and the atrial appendage 520. The leads 101 and 510 and their electrodes allow for specific atrial defibrillation of the atria, with a very small amount of energy (approximately 1-10 joules). The device extensions contain memory shaped metal or another composition, such as plastic, which holds the extensions tight against outside of the left atrium. FIG. 5 also shows the pulse generator 450 which comprises a sealed enclosure containing a battery and a circuit to generate the stimulation energy to electrodes at the distal end of the lead(s) 101 and 510.

FIG. 6A shows a portion of the procedure to implant an atrial appendage closure device around the atrial appendage 520. Installation of the atrial appendage closure device includes a magnet 525 positioned via a sheath 521 inside the atrial appendage 520. A second magnet 535 is brought near magnet 525 from outside the heart via a sheath 540 inserted through a small incision in the patient's chest. The orifice 521 is shown between the left atrium 235 and the atrial appendage 520. Once the magnet 535 is brought dose enough to magnet 525, the magnetic attraction causes the two magnets into contact with the wall of the atrial appendage 520 sandwiched therebetween. The magnets stabilize the atrial appendage 520. FIG. 6A also shows the distal end of a sheath 545 containing a lariat (discussed below).

FIG. 6B depicts the deployment of a lariat 550 around the base of the atrial appendage 520. The lariat 550 may be made of suture material or wire. FIG. 6C depicts a lead extension with electrodes 560 and 565 attached to the lariat 550. The electrodes can be placed on the lariat device before insertion into the body. The electrode array may vary depending on which configuration provides the optimal delivery of joules at the lowest resistance. There can be one or more electrodes fixed to the lariat. The electrodes may be longer and unfurl against the outside of the LA upon deployment. The covering or composition of the extensions contain memory shaped metal or other material that ensures the extensions remain in contact with the left atrium, or other epicardial surfaces. The specific length and number of electrodes and whether they unfurl depends on the energy needed to deliver the appropriate energy for defibrillation and the acceptable resistance generated. FIG. 6D shows the lariat 550 in place and cinched around the base of the of the atrial appendage 520 thereby closing off the orifice from the left atrium 525 into the atrial appendage. FIG. 6D also shows the electrode 560 positioned on the lariat 550 and thus just outside the left atrium.

FIG. 7 depicts the electrode 560 separate from the lariat 550. In this example, the electrode 550 is a coiled spring electrode. The electrode may unfurl and be present on the outside of the LAA base and or LA. There can be more than one electrode. The configuration can be a star or circle or other shape. However, the configuration of the electrode 560 may be other than that shown in FIG. 7 in other embodiments. In other examples, the portion of the electrode pressed against the left atrial tissue may be longer than that shown in FIG. 7 or there may be one or more additional electrodes on the lariat 550 to increase the surface area along the left atrium. The configuration of the electrode array may vary somewhat also to accommodate the size of the atrial appendage closure device.

FIGS. 8A-8D illustrate the closure of the orifice between the left atrium 235 and the atrial appendage 520 from inside the heart using a plug 810 (also referred to as a left atrial appendage occluder). The plug 810 is fitted with one or more electrodes connected to a pulse generator (e.g. pulse generator 450) and used for defibrillation. One or more other electrodes are positioned in the right atrium, right ventricle, left ventricle, coronary sinus, or intra-atrial septum. The plug 810 is deployed through a sheath 805.

Figure 8A:
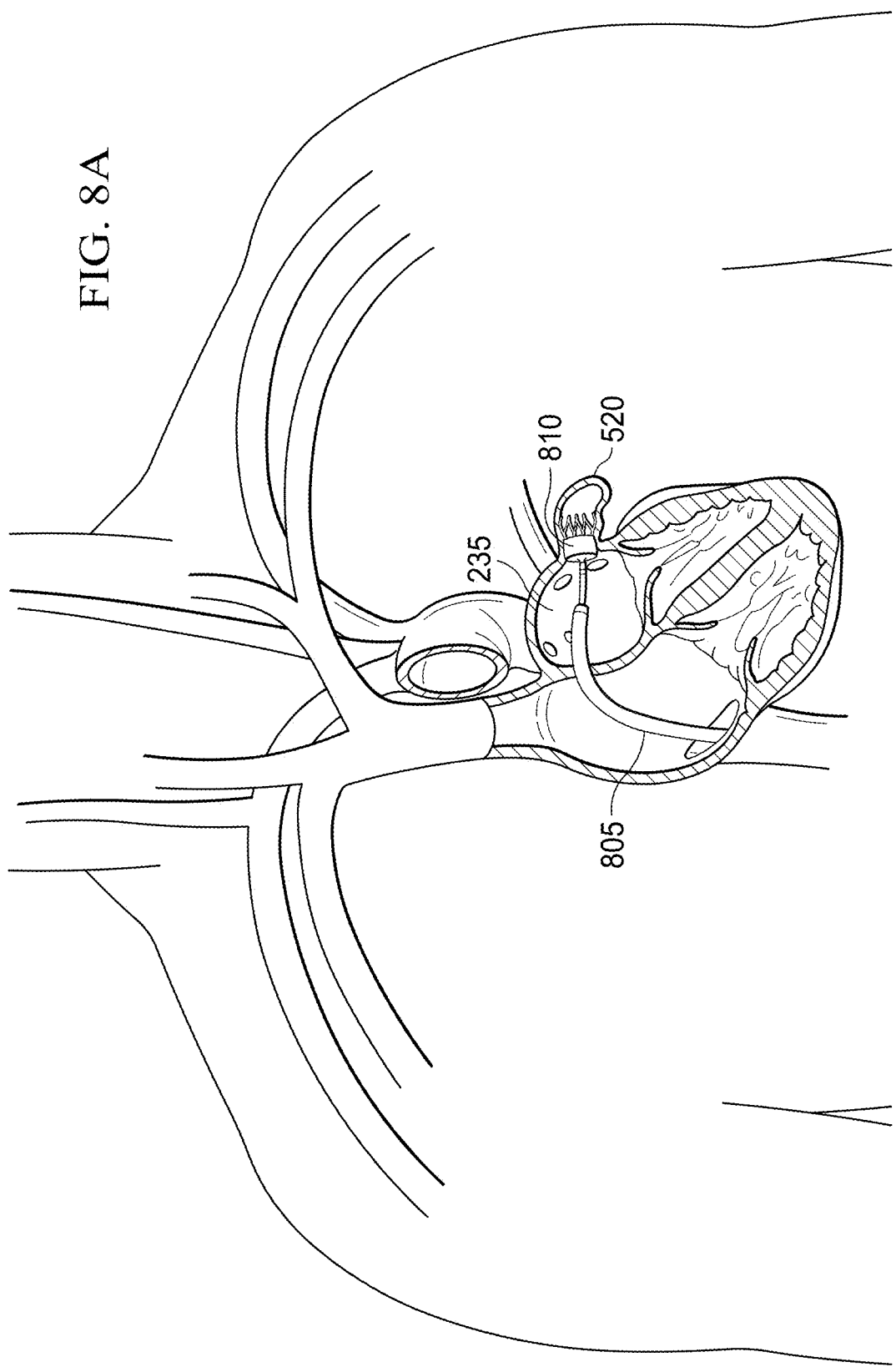
Figure 8B:
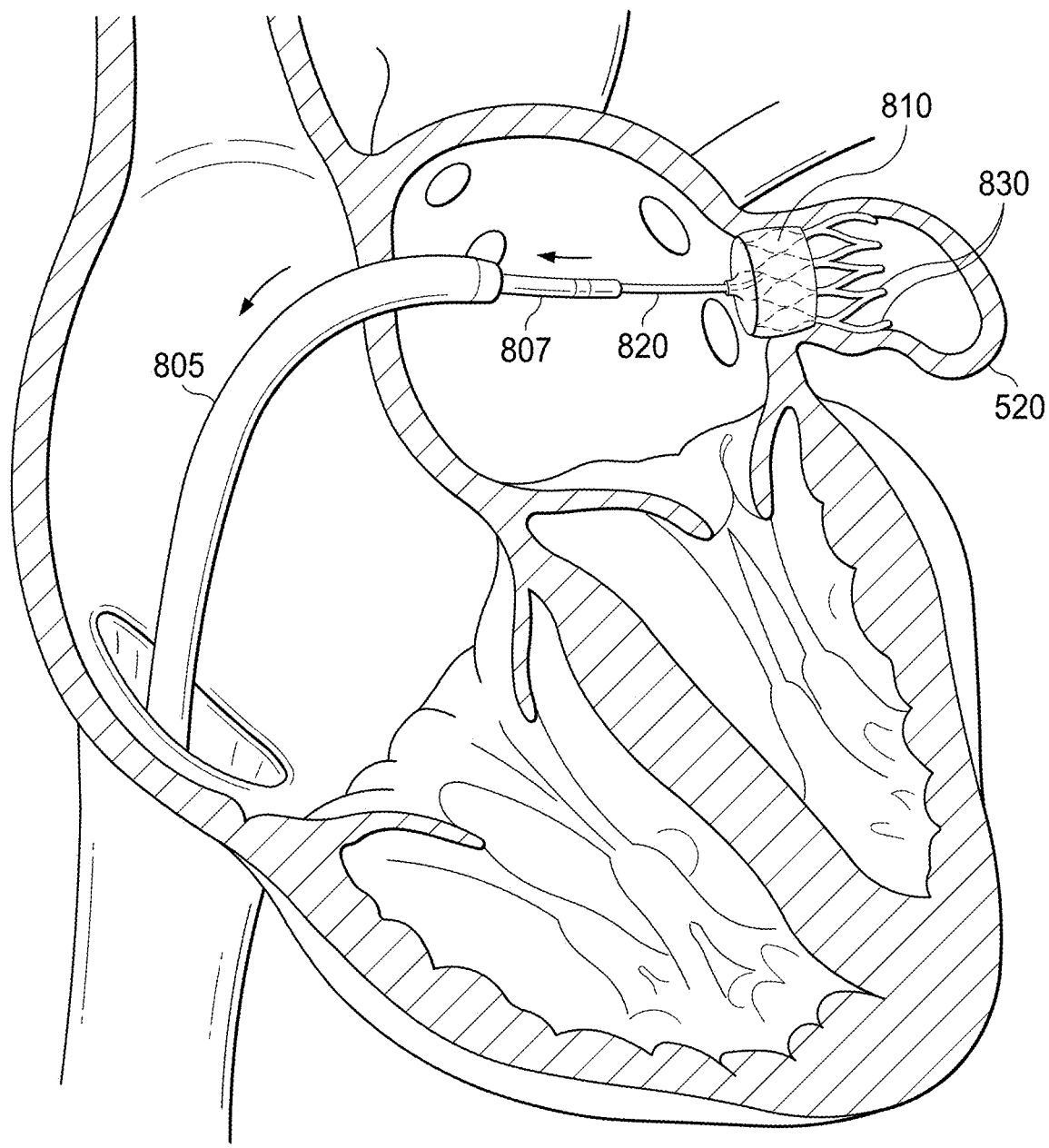

FIG. 8B shows the retraction of the sheath 805 and a plug deployment member 807. A lead 820 is shown inside the plug deployment member 807. The lead 820 is exposed when the sheath 805 and plug deployment member 807 are retracted. Electrodes 830 are shown on the lead 820 inside the atrial appendage 520. The device keeps the wires snugly against the inside heart walls, which keep the wires out of the flow of blood. In this position, the wires become embedded in the atrial wall.

Figure 8C:
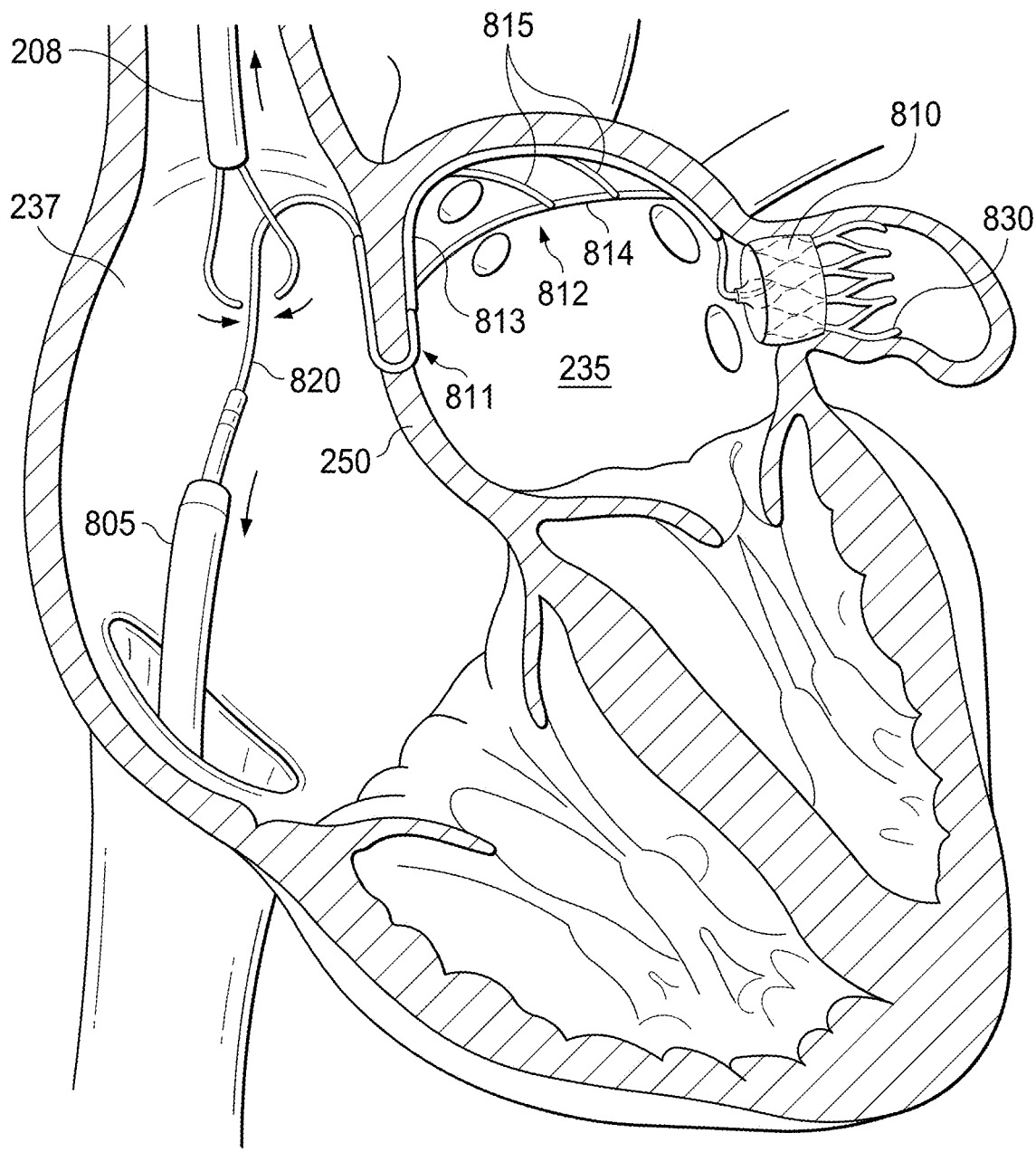

In FIG. 8C, the lead 820 from the left atrial closure device (plug 810) extends from the device and upon retraction of the sheath 805 and plug deployment member 807 brings the attached lead 820 into the right atrium 237. In the right atrium 237, the lead is then grasped or directed with a snare device 208 to be delivered into the left or right subclavian vein or other vein for connection to a pulse generator 450 that would be placed subcutaneously as described above. FIG. 8C also shows a lattice 812 coupled to a U-shaped dip 811 that is coupled to the septum 250. The lattice includes, for example, a first wire 812 and a second wire 813, both coupled to the U-shaped dip 811 and configured to be restrained against the endocardium of the left atrium 235. More than two wires can be included as desired. The wires 812 and 813 are interconnected and spaced apart by one or more interconnecting wires 815, also which are restrained against the wall of the left atrium. The U-shaped dip 811 and wires 813, 814, and 815 may be formed from any suitable type of shape memory metal, such as Nitinol.

FIG. 8D shows the final configuration of plug 810 dosing off the atrial appendage 520 with the left atrial lead 820 extending from the left atrial closure device (plug 810), extending along and hugging the interior wall of the left atrium 235. The wire then traverses the atrial septum to the right atrium. The lead 820 then extends through the superior vena cava (alternatively, the inferior vena cava) to a more peripheral vein that would allow access to the pulse generator 450 (which may be configured to perform defibrillation and/or pacing). A right atrial (as in FIG. 1, lead 101) may also be present and connected to the pulse generator 450. Such additional lead could also be a lead positioned in, for example, the right ventricle, left ventricle, or coronary sinus lead.

In the example of FIGS. 8C and 8D, the active electrode (providing stimulation or sensing capability) can be provided on the lattice 812 (e.g., wire 814), in or on the plug 810, or on both the lattice and the plug. In one embodiment, the electrode is on one of wires 813 or 814 of the lattice 812, and the other wire 813, 814 of the lattice with its shape memory helps to force the electrode-carrying wire into continuous contact with the atrial wall. In one embodiment, the lattice 812 is present but not the plug 810. Further, the U-shaped dip 811 may or may not have an electrode. In one example, the dip 811 functions as an anchor for another structure (e.g., the lattice 812, a pacing lead, etc.) and is not itself used for sensing or stimulation purposes.

Figure 8E:
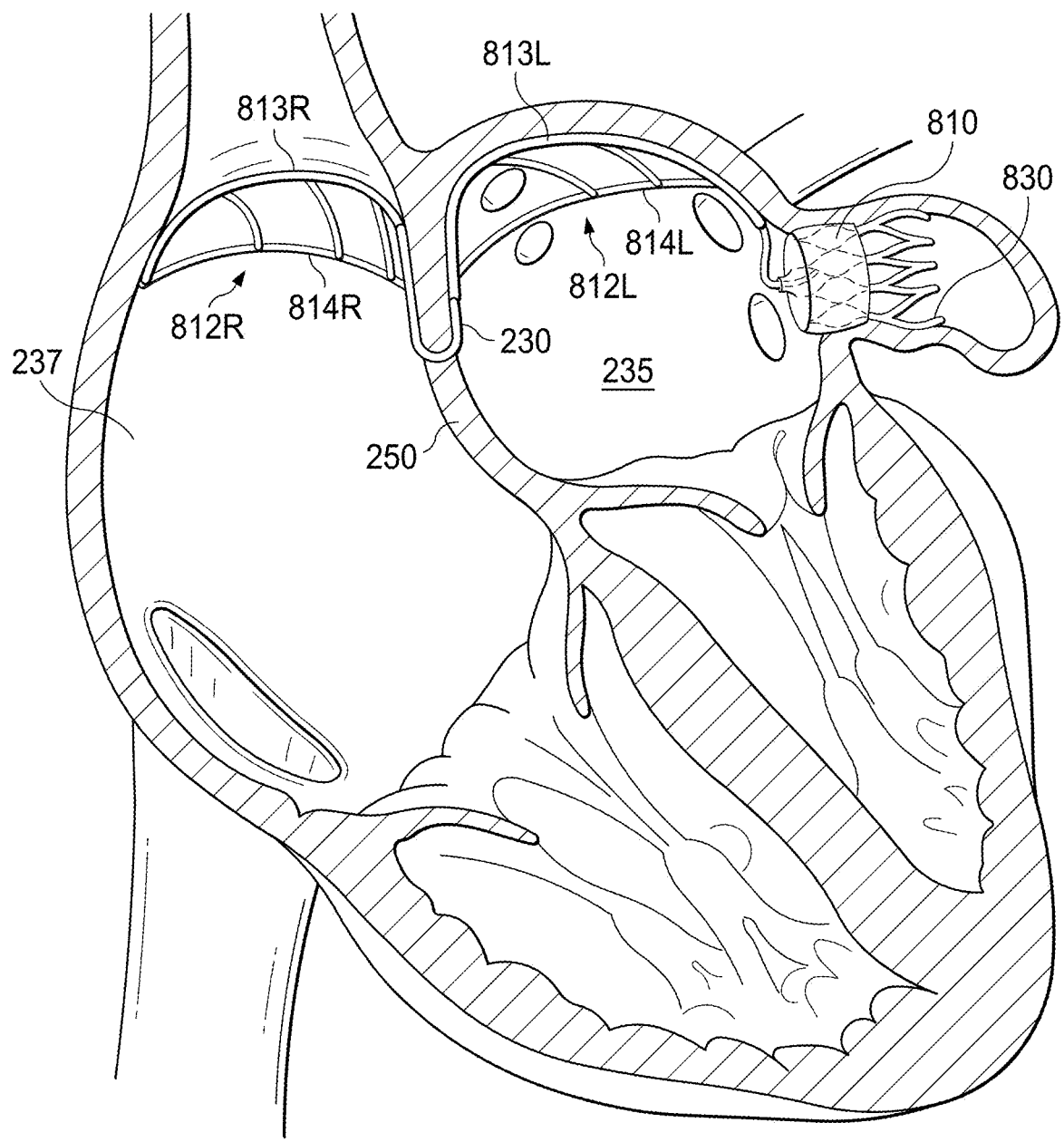
FIG. 8E is an illustration of an illustrative embodiment of another embodiment of extended electrodes that are integrated with respective lattices that are connected (electrically and physically) connected to the septal electrode.

With regard to FIG. 8E, an illustration of an illustrative embodiment of another embodiment of extended electrodes 813L and 813R (collectively 813) that are integrated with respective lattices 812L and 812R that are connected (electrically and physically) to the septal electrode 230 is shown. Wires 814L and 814R may also be configured with a shape preform (i.e., with a shape memory) to extend along and maintain contact with the endocardium of the respective left 235 and right 237 atria. In an embodiment, the wires may be non-insulated or partially insulated (e.g., insulation along a portion, along a side with the metal exposed on the other side for endocardium contact, or along a portion and along a side). Although not shown, the septal electrode 230 may be connected to a lead (e.g., lead 103 of FIG. 2J, for example) or to a leadless pacemaker (e.g., leadless pacemaker 260 of FIG. 2N) for providing electrical signals to the septal electrode 230 for delivering the electrical signals to the extended electrodes 813.

Figure 8F:
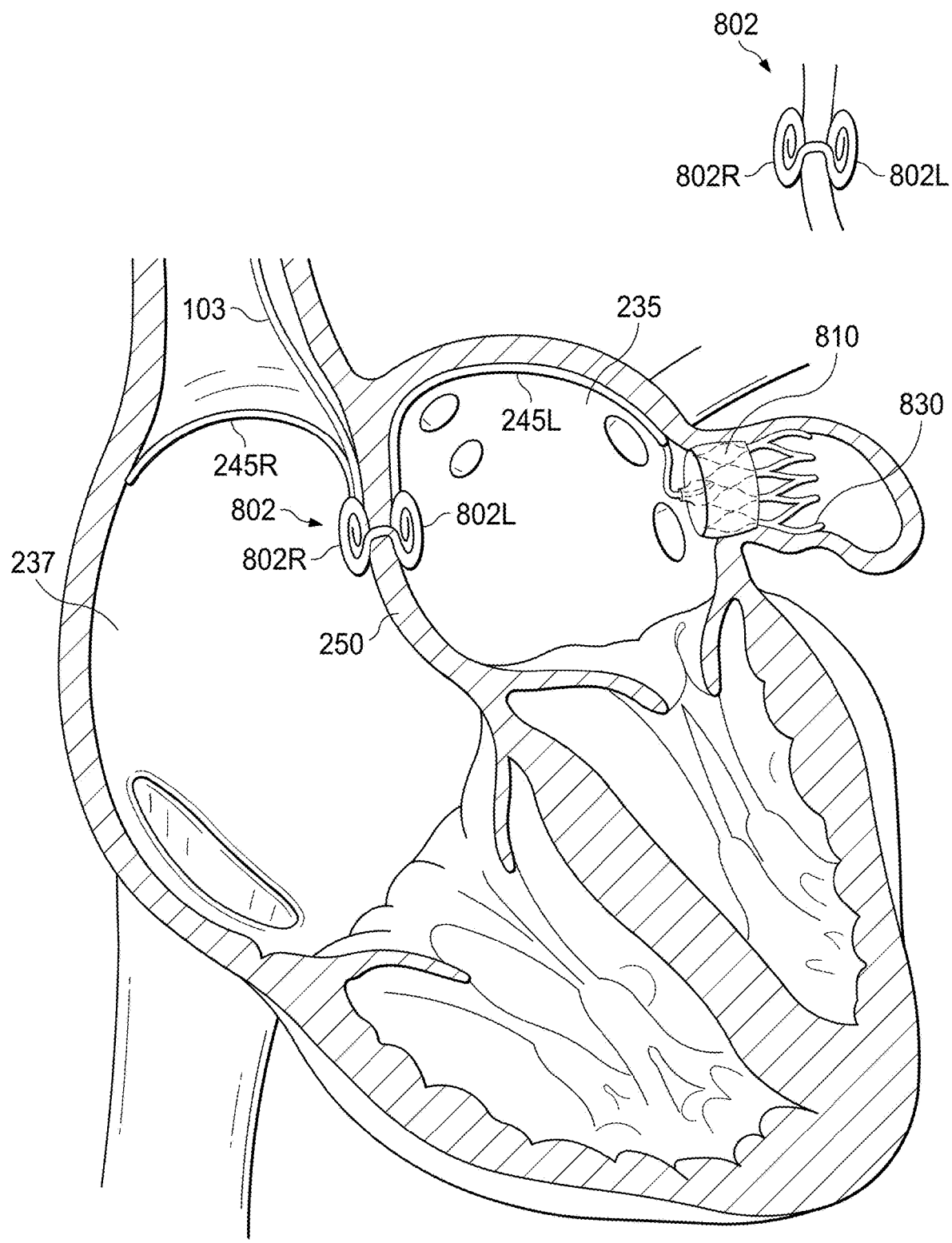
FIG. 8F is an illustration of alternative embodiment of a septal electrode configured as a pair of springs that form the septal electrode.

With regard to FIG. 8F, an illustration of an alternative embodiment of a septal electrode 802 configured as a pair of springs 802R and 802L that form the septal electrode 802 is shown. The springs 802R and 802L may function to hold the extension electrodes 245 along the atrial septum 250 and endocardium of the left and right atria 235 and 237. In this embodiment, a lead 103 may be electrically connected to the septal electrode 802. The springs 802R and 802L may be conductive or non-conductive. If non-conductive, a conductor may be integrated with the septal electrode 802 to provide for electrical connections with the lead 103 and extension electrodes 245. In an embodiment, opposing plates (not shown) may be disposed between the springs 802R and 802L that are used to hold the septal electrode 802 with the atrial septum 250. Protrusions (not show) may be positioned on the springs 802R and 802L (and/or plates) facing the atrial septum 250 to provide added support for maintaining the septal electrode 802 against the atrial septum 250. Although springs 802R and 802L are shown, it should be understood that only a single spring, such as spring 802L, may be utilized and the spring 802R may be a plate or other structural element. It should further be understood that a variety of configurations of the septal electrode 802 may be utilized to perform the same or similar functions in providing both electrical conductivity and support for the extension electrodes 245, as provided herein.

Figure 9:
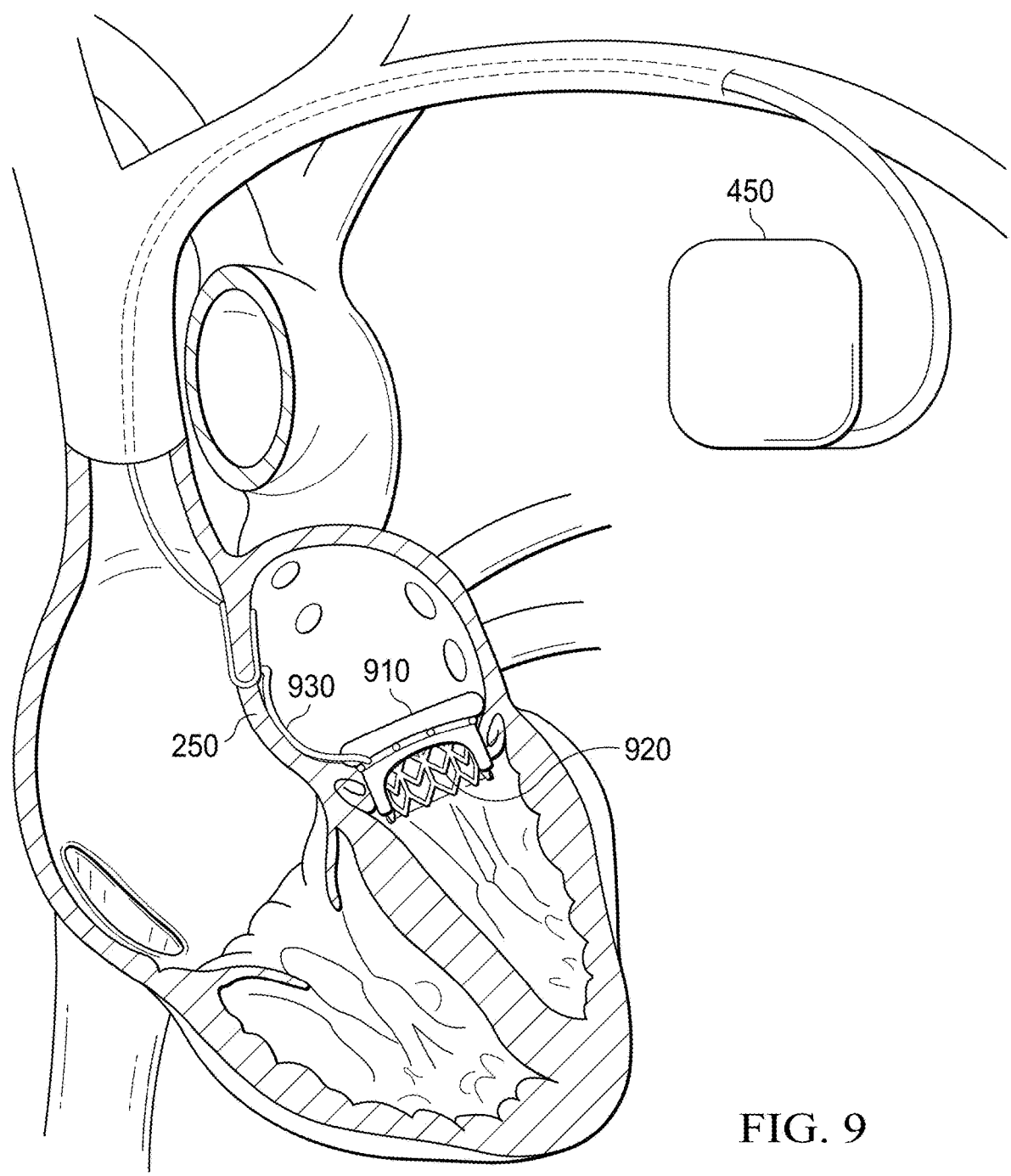
FIG. 9 shows an embodiment in which an electrode is part of a mitral valve device in which the wires are connected to the electrodes on the mitral annulus and hug the atrial septum, and connect to the electrode embedded in the septum.

In another embodiment, a left atrial lead can be incorporated a mitral valve replacement and/or mitral valve repair, either transseptal via a percutaneous approach or minimally invasive or open surgical approach. For example, an electrode array can be incorporated into mitral valve devices that touch or are near the left atrium. FIG. 9 shows a prosthetic mitral valve device 910 which is incorporated with one or more electrodes 920 forming an electrode array. The electrodes 920 are on the distal end of an atrial lead. The lead 930 would then be routed through the atrial septum 250 and connected to a pulse generator 450 as described above. The orifice of the mitral valve, where most mitral valve devices (such as mitral valve device 910) are positioned, is a suitable site for bi-atrial defibrillation with the device described herein. One configuration of the electrode array would be a conductive thin wire woven or otherwise attached to the valve device 910 as it sits around the mitral orifice. The mitral valve device 910 or devices may accommodate the electrode array and lead 930. Lead 930 can extend and overlap with the septal restraining device. The septal restraining device then connects to an insulated wire which connects to a pacemaker and/or defibrillator or transducer. The mechanical properties of the device hold the wires and extensions against the atrial wall, where tissue ingrowth will occur, as it does with the implanted mitral valve. The lead 930 can also allow attachment to another grasping device (e.g., snare device 208) to bring the wire to the appropriate site near the defibrillator/pacemaker pocket.

Referring further to FIGS. 3D-3F, one embodiment of installing the implantable device for treating atrial fibrillation (AFIB) may include clamping the septal electrode 360 on the septum 250 with extension electrodes 362 extending along the wall(s) 352R and 352L (e.g., along the endocardium, myocardium, and/or epicardium of the wall(s) 352R and 352L) is shown. Once clamped, measurements of heart electrical signals via the may be performed, wherein the heart electrical signals may include the R-wave, P-wave, S-wave, and/or any other segments of a heart electrical signal. Because the septal electrode 360 is configured to clamp to the septum 250, if the heart electrical signals have poor or lower than anticipated measurements (e.g., low amplitudes), then the projection members 372 may be separated such that the flat surfaces 376 of the sleeves 364 may be separated from the septum 250 and rotated to cause the extension electrodes 362 to be re-aligned and engage with different regions of the endocardium, for example. If the extension electrode 362b extends into the wall junction 352j, then the extension electrode 362b may be withdrawn and re-inserted into a different area to try and form a better contact location.

Figure 3G:
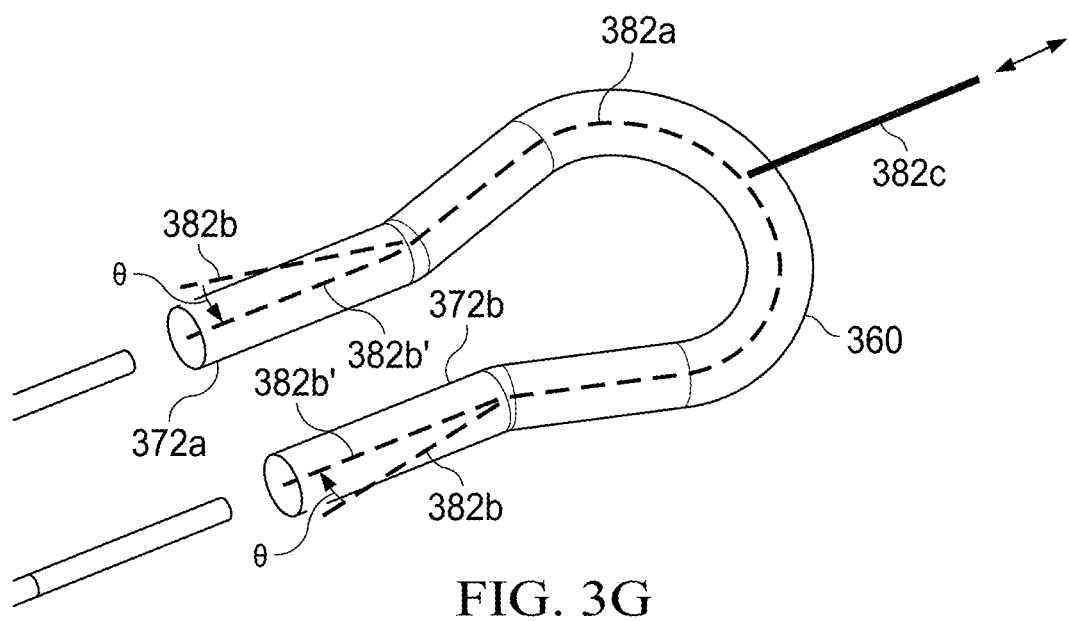
FIG. 3G is an illustration of an embodiment of the septal electrode that includes a center post with portions that extend therethrough.

With regard to FIG. 3G, an illustration of an embodiment of the septal electrode 360 that includes a center post 382 with portions 382a, 382b, 382c (collectively 382) that extends therethrough is shown. The center post 382 may be slid into and out of the septal electrode 360. The portions 382b may be biased outwards at an angle theta (θ) such that when the portion 382c of the center post 382 is pulled out of the septal electrode 360, the projection members 372 rotate by the angle theta so as to be parallel with one another, thereby clamping to the septum 250. In the event that the extension electrodes 362 are not adequately conducting the heart electrical signals, then the operator may slide the center post 382 back into the septal electrode 360, thereby causing the portions 382b to spread the projection members 372 for rotating and re-clamping the septal electrode 360.

Figure 10:
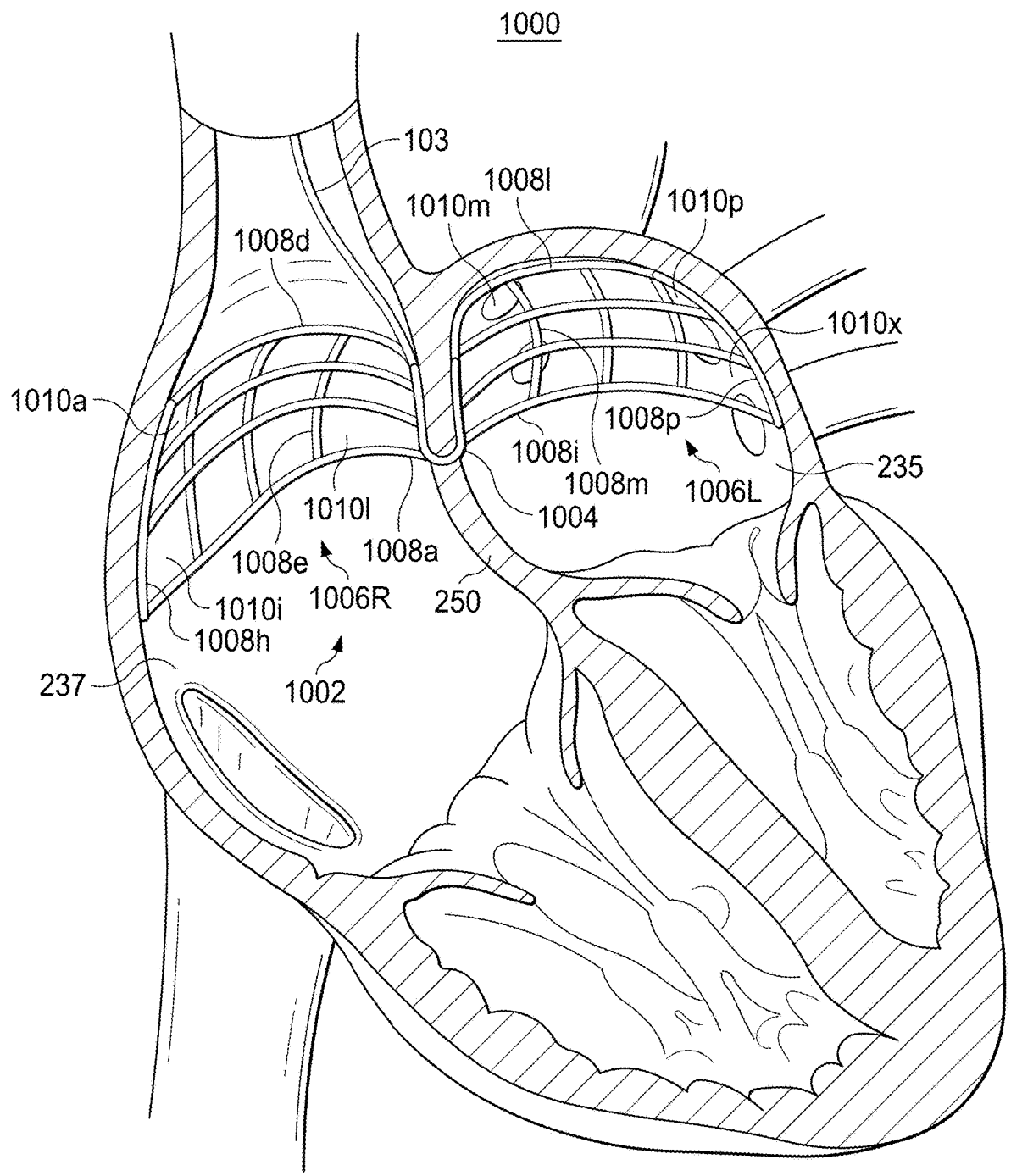
FIG. 10 is an illustration of a heart in which an illustrative implantable heart sensing structure has been biatrially implanted, where the implantable heart sensing structure may be used (i) to pace and defibrillate one or both of the upper chambers of the heart, and (ii) to sense problematic heart tissue that may trigger an atrial fibrillation event.

With regard to FIG. 10, an illustration of a heart 1000 in which an illustrative implantable heart sensing structure 1002 has been biatrially implanted, where the implantable heart sensing structure may be used (i) to pace and defibrillate one or both of the upper chambers of the heart, and (ii) to sense problematic heart tissue that may trigger an atrial fibrillation event is shown. In an alternative embodiment, rather than being biatrially implanted, the implantable heart sensing structure 1002 may be implanted in only one of the atriums, such as the left atrium. The implantable heart sensing structure 1002 may include a septal electrode 1004 from which one or two extension electrode matrices 1006R and 1006L are electrically coupled. The extension electrode matrix 1006R is shown to include rows of extension electrodes 1008a-1008d and columns of extension electrodes 1008e-1008h (collectively 1008), thereby forming a 12×12 matrix of cells 1010a-1010l (collectively 1010R). The extension electrode matrix 1006L is shown to include rows of extension electrodes 1008i-1008l and columns of extension electrodes 1008m-1008p, thereby forming a 12×12 matrix of cells 1010m-1010x (collectively 1010L). In an embodiment, rather than the columns of extension electrodes 1008e-1008h and 1008m-1008p being conductive, those structural elements may be non-conductive, thereby creating an arrangement of rows of conductive extension electrodes 1008a-1008d and 1008i-1008l. It should be understood that the orientation of the extension electrodes 1008 are illustrative, and that the orientation and configuration of the extension electrodes may be rotated or otherwise. For example, the extension electrodes may be equidistant or non-equidistant from one another, lengths may be different, etc.

It should be understood that the extension electrode matrices 1006R and 1006L are illustrative and that matrices with more or fewer rows and columns of extension electrodes may be utilized. It should further be understood that the shape and configuration of the extension electrode matrixes are illustrative, and that different sizes, shapes, and configurations that cover more or less of one or both of the left and right atria may be utilized. For example, a mesh that covers a larger surface area may be utilized to cover a larger surface area may be utilized. The septal electrode 1004 is shown to be a single electrode, but other embodiments where multiple septal electrodes are utilized may be utilized. For example, each extension electrode or pair of extension electrodes may have a common septal electrode. The extension electrodes and matrices formed thereby should be configured to remain in contact with the endocardium of the respective left and right atriums, but be sufficiently flexible to avoid restricting natural movement of the walls of the heart chambers.

With regard to FIG. 11, an electrocardiogram (ECG) graph 1100 showing electrical signal 1102 of a typical, healthy heartbeat captured by an electrocardiogram measurement of a heart is shown. The ECG graph 1100 shows typical changes in electrical signal 1102, in this case voltage, produced by the heart as measured by electrodes positioned on skin of a patient. The electrical signal 1102 includes several waves, including a Q-wave, R-wave, and S-wave, where the Q-wave and S-wave are the downward deflection (each wave starting and ending at the horizontal line) and the R-wave is the upward deflection (starting and ending at the horizontal line). The P and T features are indicators of respective depolarization and repolarization of the ventricles of the heart. A combination of the Q-wave, R-wave, and S-wave is known as the QRS complex and occurs during ventricle contraction. Each heartbeat produces the electrical signal 1102 on the ECG graph 1100, and successive sequence of the P-T interval over time is a person's heart rate (e.g., 60 beats per minute (bpm)). In other words, for successive heartbeats, the electrical signal 1102 with each signal of the P-T interval is repeated such that the T feature completes before another P feature initiates, as commonly understood in the art. It should be understood that the ECG graph is illustrative of typical shapes of ECG graphs. It should further be understood that the electrical signals captured by extension electrodes, such as those shown in FIG. 10, may be different in scale or otherwise as a result of being in direct contact with the epicardium of the heart wall.

With regard to FIGS. 12A-12C, ECG graphs 1200a-1200c (collectively 1200) of a sequence of illustrative electrical signals $1202a_1$-$1202a_4$ (collectively 1202a), $1202b_1$-$1202b_4$ (collectively 1202b), and $1202c_1$-$1202c_4$ (collectively 1202c) (collectively 1202) are shown. With regard to FIG. 12A, the electrical signals 1202a are shown to be overlapping because the signals $1202a_1$-$1202a_4$ are sensed by four extension electrodes, such as extension electrodes 1008i-1008l, positioned within the left atrium 235 and extend along the endocardium therein. The electrical signals 1202a are each identical to the electrical signal 1102 of FIG. 11, have approximately equal amplitudes $A_1$, and have approximately equal time delays $\Delta T_1$ between one another. The time delays $\Delta T_1$ are shown to be substantially the same because the extension electrodes 1008i, 1008j, 1008k, and 1008l have substantially the same spacing relative to one another and the heart wall tissue between each of the extension electrodes 1008i-1008l has consistent electrical characteristics (e.g., the heart wall tissue does not have problematic tissue (e.g., scar tissue, dead tissue, etc.) that is affecting electrical signals emanating from the sinoatrial (SA) node, which is an oval shaped region of special cardiac muscle in the upper back wall of the right atrium made up of calls known as pacemaker cells.

With regard to FIG. 12B, the electrical signals 1202b each have a common amplitude $A_1$ at the peak of the R-wave, but a time delay of $\Delta T_2$ between electrical signals $1202b_2$ and $1202b_3$ exists, whereas a common time delay of $\Delta T_1$ exists between electrical signals $1202b_1$ and $1202b_2$ and between electrical signals $1202b_3$ and $1202b_4$. The reason for the longer time delay of $\Delta T_2$ (as compared to $\Delta T_1$) between electrical signals $1202b2$ and $1202b3$ is because problematic heart wall tissue produces a time delay of $\Delta T_2$, which may indicate an increase in electrical impedance through the heart wall tissue compared to healthy heart wall tissue, whereas healthy heart wall tissue results in the time delay $\Delta T_1$. Although not shown, it should be understood that time delays that are shorter than $\Delta T_1$ may be sensed, which would indicate a short-circuit or drop in electrical impedance through the heart wall tissue.

It should be understood that the electrical signals and timing thereof is illustrative in showing how problematic heart wall tissue may result in disorganized electrical signals, such as the time-shifted electrical signals $1202b_3$ and $1202b_4$, thereby resulting in uncoordinated contraction of the chambers of the heart. It should be understood that the extension electrodes that sense the electrical signals 1202b are equally spaced and it is assumed that the only variable is a time-shifted electrical signal as a function of the heart wall tissue. It should further be understood that if the extension electrodes have unequal spacing (e.g., spacing between 1008j and 1008k is larger than spacing between sequential electrodes 1008i and 1008j and sequential electrodes 1008k and 1008l), then the time delay $\Delta T_2$ may be consistently measured. And, if such a time delay $\Delta T_2$ is consistently measured, then an change (e.g., increase) of that time delay $\Delta T_2$ would be an indication that heart wall tissue is beginning to have problems. As a result, initial measurements at the time of installation of the extension electrode matrices 1006L and 1006R should be made, and if such a time delay $\Delta T_2$ is determined to be normal (i.e., no apparent problematic heart wall tissue exists between extension electrodes 1008j and 1008k, then a measurement system, such as a pacemaker, should use those measurements as a baseline from which future comparisons of electrical signals from the extension electrode $1008k$ are made to determine whether heart wall tissue is beginning to have or has a problem.

With regard to FIG. 12C, the electrical signals $1202c_1$ has an amplitude $A_1$ at the peak of the R-wave, while electrical signals $1202c_2$-$1202c_4$ have amplitudes $A_2$ at the peak of the R-wave. The reason for the attenuation of the amplitude from $A_1$ to $A_2$ between electrical signals $1202c_1$ and $1202c_2$-$1202c_4$ may be due to problematic heart wall tissue between extension electrodes that sense the electrical signals $1202c_1$ and $1202c_2$-$1202c_4$. Once the amplitude of an electrical signal is attenuated in the heart wall, the electrical signal remains attenuated such that each of the extension electrodes 1008. It should be understood that additional attenuation may occur either naturally or as a result of heart wall tissue becoming problematic over time. The electrical signals $1202c$ are illustrative and are illustrative of only a single variable changing as a result of heart wall tissue between two extension electrodes becoming problematic. As described with regard to FIG. 12B, if the initial measurements are made with an installed extension electrode matrix, such as extension electrode matrix 1006L, that show the attenuation between amplitude $A_1$ and $A_2$ of electrical signals $1202c_1$ and $1202c_2$-$1202c_4$, then future electrical signal measurements for determining if heart wall tissue becomes problematic should be based on the initial electrical signals $1202c$, for example.

Although not shown, it should be understood that both decreased time delays (or accelerated time shifts) and attenuation of amplitudes may also result from problematic tissue forming (as well as angular, distance, or other physical differences between the extension electrodes being used to sample the electrical signals). There are many other examples of electrical signals that may be measured as a result of the heart wall tissue, connection of the extension electrodes, and many other factors, but that changes in the electrical signals measured over time may be indicative of heart wall tissue becoming problematic. Moreover, such changes between the measured electrical signals may be used for identifying location of problematic tissue and be used to prevent an occurrence of a future AFIB event (or the onset of other heart conditions) by performing an ablation to remove or correct the heart wall tissue.

Although only four electrical signals $1202a_1$-$1202a_4$ are shown, it should be understood that there may be many more depending on the number of extension electrodes in a mesh with nodes along the rows and columns. From those electrical signals $1202a_1$-$1202a_4$, a determination of location at the extension electrode matrix 1006L or 1006R may be made based on timing, phase, etc., as provided with regard to FIG. 14B.

The examples shown is FIGS. 12A-12B are illustrative of actual measurements. However, time shifts, either faster or slower, of the electrical signals, may not occur instantaneously, but rather may occur gradually over time. Meaning, where time delay $\Delta T_2$ is shown to have a longer time period than time delay $\Delta T_1$, that time delay from $\Delta T_1$ to $\Delta T_2$ (assuming an initial measurement of $\Delta T_1$) may occur over a fairly long time period (e.g., over the course of months or years). As such, the principles described herein may use various algorithms to monitor that shift in the time delay of electrical signal $1202b_3$. As will be described below with regard to FIG. 14, an electronic device, such as a pacemaker, may establish initial timing of the electrical signals $1202a_1$-$1202a_4$ (using the ECG graph as a baseline) and establishing timing threshold values that may be used to trigger notifications and/or alarms for a patient and/or physician. The measurements may be individual readings, average readings, or any other mathematical computation for readings so as to minimize false positives and/or false negatives. For example, derivatives (rate), second derivatives (acceleration), and integrations (averages, volume under curve) may be performed to determine changes of the measurements over time. The same principles of establishing a baseline and monitoring the electrical signals with regard to amplitude of the peak R-wave (or any other portion of the electrical signals) in order to determine whether problematic heart tissue is developing. Again, notification and/or alarms of a threshold, either high or low threshold, being crossed may be used to notify a patient and/or physician that the amplitude of the electrical signals have changed over time from baseline measurements.

In addition to or alternative to using electrical signals for identifying problematic heart issue, electrical characteristics, such as impedance, of heart wall tissue may be measured using the extension electrodes, such as extension electrodes 1008 of FIG. 10. Using the extension electrodes for sensing electrical characteristics enables the extension electrodes to be used for both sensing the electrical characteristics of the heart wall tissue and electrical signals that are produced by the heart, as previously described. However, circuitry within an electronic device used to sense the two different signals may be different. The extension electrodes may be connected to a septal electrode, such as septal electrode 1004, formed of a single conductor or multiple conductors that are electrically isolated from one another.

Figure 12D:
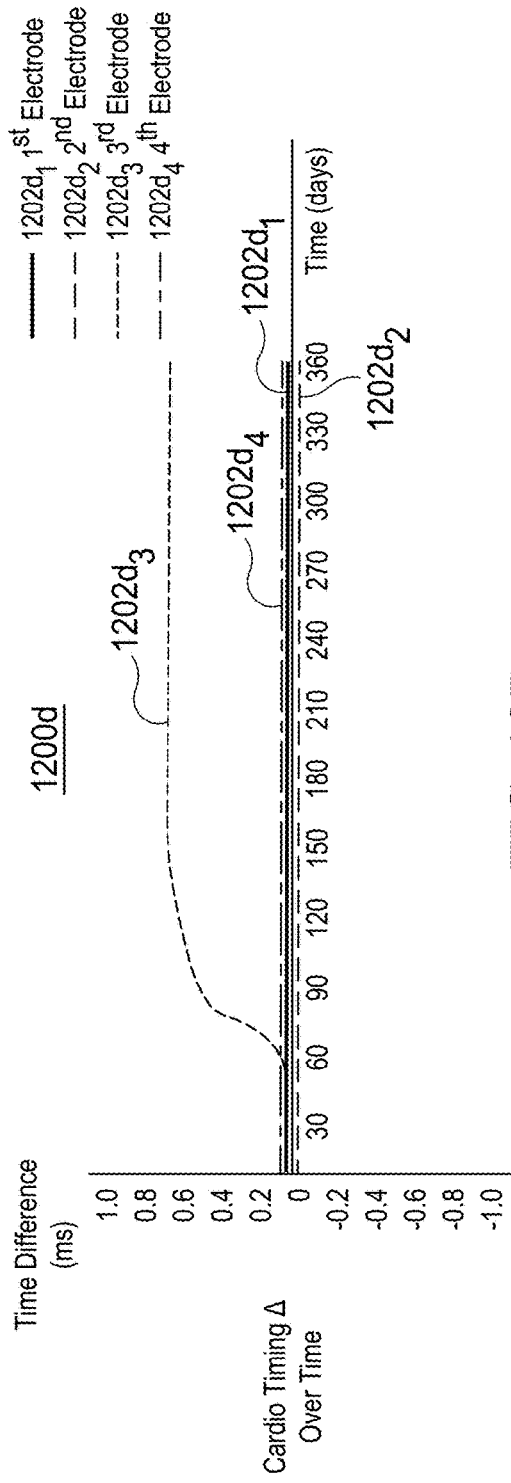
FIG. 12D is a graph of illustrative signals representing cardio timing difference over time sensed by each of the electrodes of FIG. 10.

With regard to FIG. 12D, a graph $1200d$ of illustrative signals $1202d_1$-$1202d_4$ representing cardio timing difference over time sensed by each of the electrodes of FIG. 10 is shown. The x-axis is time over days and the y-axis is time difference in milliseconds (showing a change of timing of electrical signals between each of the sequential electrodes). As shown, timing difference of the $3^{rd}$ extension electrode (e.g., extension electrode $1008j$) from the $2^{nd}$ extension electrode $1008k$ begins increasing at around 60 days and accelerates until about 75 days. Thereafter, the time difference continues to grow and levels off at around 150 days. The increase of the timing difference starting at around 60 days of the signal $1202d_3$ may be indicative that the heart wall tissue is becoming problematic between the $2^{nd}$ and $3^{rd}$ extension electrodes $1008k$ and $1008j$. Each of the timing differences of the other electrodes remains at about 0ms, which means that the heart wall tissue is likely still healthy.

Figure 12E:
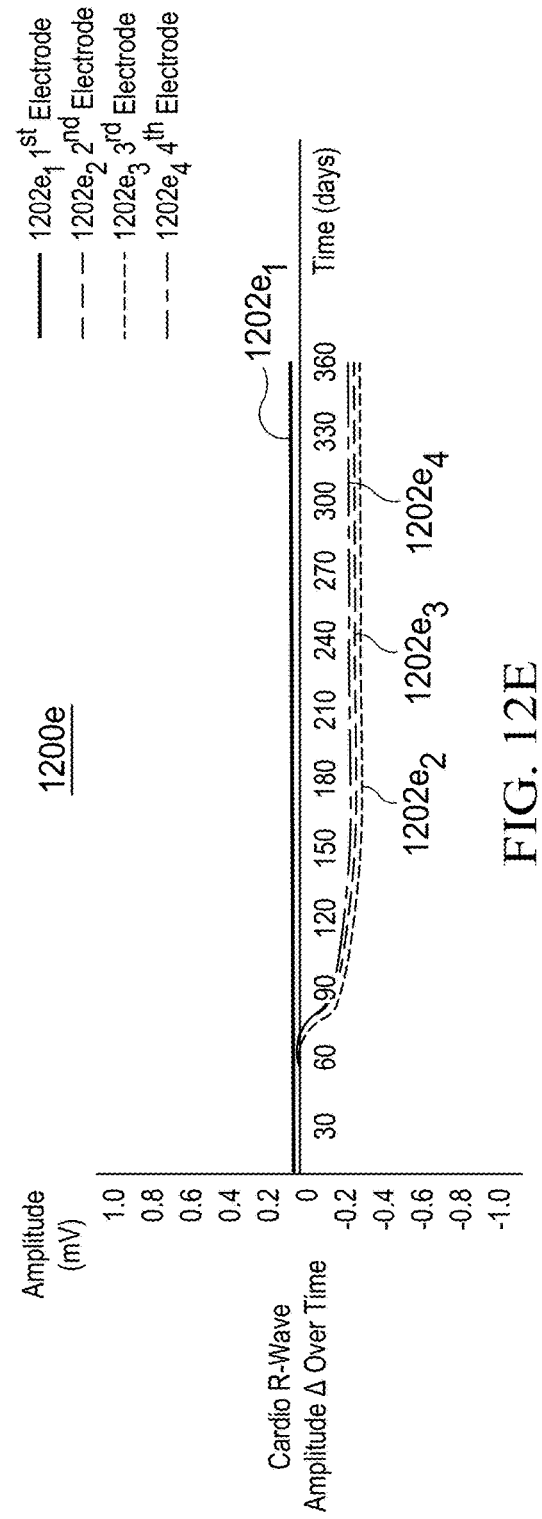
FIG. 12E is a graph of illustrative signals representing cardio R-wave amplitude difference over time sensed by each of the electrodes of FIG. 10.

With regard to FIG. 12E, a graph $1200e$ of illustrative signals $1202e_1$-$1202e_4$ representing cardio R-wave amplitude difference over time sensed by each of the electrodes of FIG. 10 is shown. The x-axis is time over days and the y-axis is amplitude in millivolts as sensed by each of the extension electrodes. As shown, amplitude of the electrical signals over time of the $1^{st}$ extension electrode $1008l$ relative to the sinoatrial node remains constant over time (i.e., the amplitude of the electrical signals does not drop because the heart tissue prior to receiving the electrical signals is healthy). However, as shown, the $2^{nd}$-$4^{th}$ extension electrodes $1008k$, $1008j$, and $1008i$ sense lower amplitude signals of the R-wave starting at around 60 days, which indicates that the heart wall tissue is attenuating the electrical signal after the $1^{st}$ extension electrode $1008l$ and prior to the $2^{nd}$ extension electrode $1008k$ (and each of the $3^{rd}$ and 4th extension electrodes $1008j$ and $1008i$) relative to the sinoatrial node. It should be understood that the R-wave amplitude may be one of several amplitude measurements (i.e., other electrical signal features may additionally or alternatively be measured and used for determining whether or not a region of the heart wall tissue is becoming problematic over time). It should be understood that because the data points that are being monitored for the signal measurements of FIG. 12 are limited (e.g., peak R-wave data point sensed by each extension electrode, timing difference between each of the electrical signals sensed by each extension electrode, a time difference between successive extension electrodes receiving an electrical signal, and so on), an amount of memory used to store the collected data may be small.

Myocardial or heart wall tissue electrical impedance (Z) is defined as the voltage (V) measured across the tissue divided by the sinusoidal current (I) applied through the tissue (Z=V/I). Because the cell membranes have capacitive properties, the heart wall tissue is not purely resistive, and, therefore, there will be a time delay between the voltage and current waves that can be determined from a phase angle of tissue impedance. In these circumstances, the impedance (Z) is defined as a complex number (Z=R+jX), where R is the resistance (in phase component of V with respect to I), j is the imaginary unit (j), and X is the reactance (in quadrature component of V with respect to I). Therefore, heart wall tissue impedance can be precisely defined by two components: tissue resistance (R) and phase angle ($\theta$=arctan(X/R)).

Figure 13:
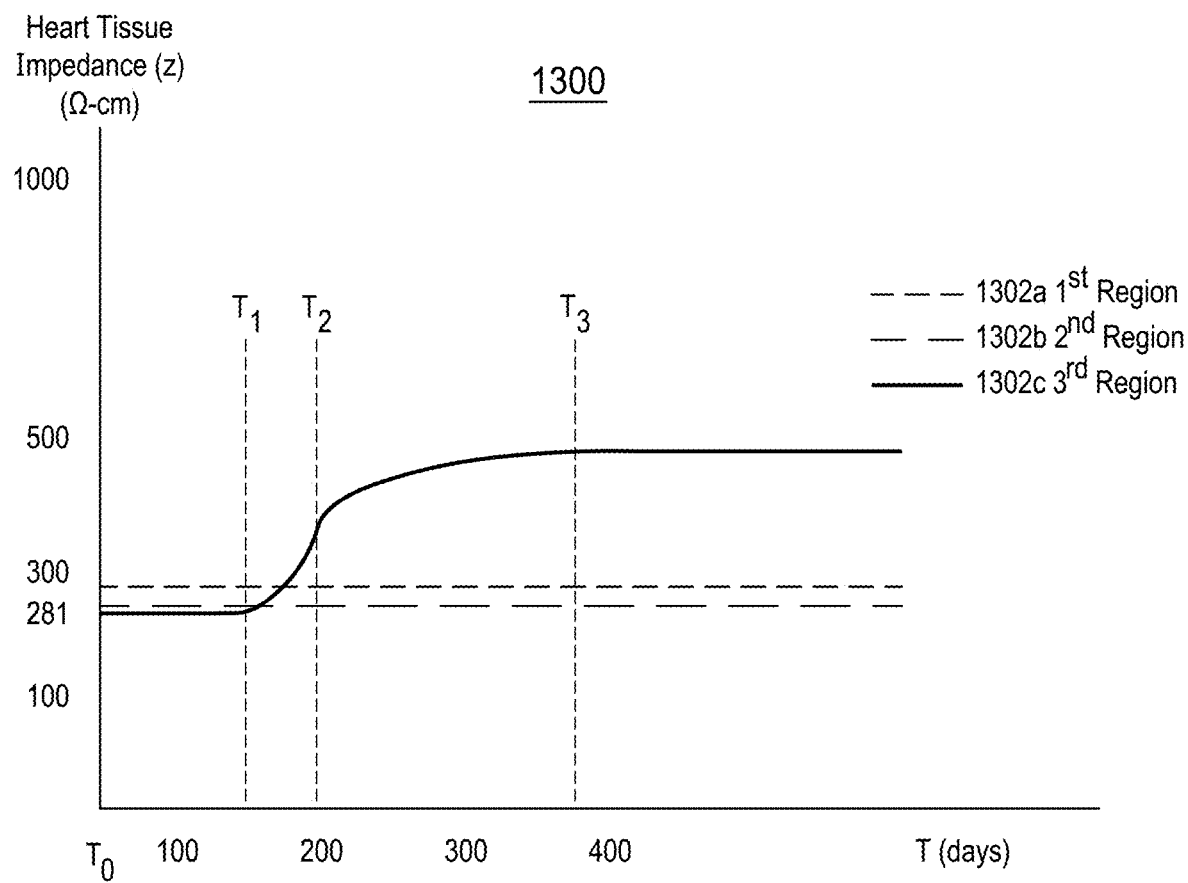
FIG. 13 is a chart of illustrative impedance measurements of heart wall tissue.

With regard to FIG. 13, a chart 1300 of illustrative impedance measurements 1302a-1302c (collectively 1302) of heart wall tissue is shown. The three impedance measurements 1302 are performed between successive extension electrodes, such as 1008i-1008l in the left atrium 235 of FIG. 10. The three impedance measurements 1302 are performed over time. Heart wall tissue typically has impedances below 300 Ohms-cm (e.g., 278-283Ω-cm). As shown, impedance measurements in each of Regions A, B, and C (e.g., cells 1010u, 1010q, and 1010m between respective extension electrodes 1008i-1008j, 1008j-1008k, and 1008k-1008l) from time $T_0$ and $T_1$ (about 160 days) are stable, where impedance measurement 1302c in Region C is at about 281 Ohms-cm. At time $T_1$, however, impedance measurement 1302c in Region C begins to quickly climb from about 281 Ohms-cm to about 350 Ohms-cm at time $T_1$ (about 200 days). From there, the impedance measurement 1302c begins to slow, but continues increasing to about 480 Ohms-cm at time $T_2$ (about 375 days).

Because the extension electrodes are maintained along the heart wall(s), the change in impedance is able to be monitored and a location (e.g., cell or area located between extension electrodes on the heart wall) at which the heart wall tissue is becoming problematic (e.g., tissue region changing electrical characteristics that results in disruption of electrical signals) may be identified, thereby reducing or eliminating the patient having to be admitted to a laboratory for determining the location of the problematic heart wall tissue. Impedance measurements may account for both real and imaginary values, where Z=square root $(R^2+(X_L-X_C)2)$; where Z is impedance, R is resistance, XL is inductive reactance, and XC is capacitive reactance. Electronics capable of performing such impedance measurements may be incorporated in an electronic device, such as a pacemaker, to which the extension electrode matrix (or rows of extension electrodes) connect.

In performing the impedance measurements, the measurements may be made either passively or actively. If active, low level electrical signals may be applied to sequential pair of extension electrodes and current or voltage drops may be measured to determine resistance or impedance between the two electrodes. The low level electrical signals may be performed over one or more frequencies (e.g., sweep frequency test), thereby providing additional information in case certain tissue problems are able to be sensed at different frequencies. Other impedance sensing techniques may be utilized in accordance with the principles described herein.

Whether using electrical signal measurements or electrical characteristics of heart tissue, in identifying location of the problematic tissue, a mapping of the extension electrodes relative to one or more features of the heart or a location through which the septal electrode 1004 extends through the septum 250 (FIG. 10). The mapping may be performed by (i) knowing the measurements of the extension electrode matrices 1006R and 1006L relative to the septal electrode 1004, (ii) imaging (e.g., X-ray, CT scan, etc.), or (iii) otherwise. The mapping may be performed using Cartesian coordinates, polar coordinates, or otherwise. In an embodiment, the mapping may simply be made by providing a location of the problematic heart wall tissue relative to the cells 1010R and 1010L formed by the extension electrode matrices 1006R and 1006L, for example, thereby providing a relative location for a doctor to locate the problematic tissue for an ablation to be performed, as further described herein. As previously described, upper and lower thresholds may be set after a baseline for each of the impedance values are established. The upper and lower thresholds may be set as 10% above and below initial impedance values, and if the upper or the lower threshold is reached, a notification may be generated and communicated to a physician and/or patient. Moreover, a maximum and a minimum threshold may be set that, if reached, may cause an alarm to be generated and communicated to the physician and/or patient. Such thresholds may be set in an electronic device or other device to which the electronic device communicates to perform the monitoring, charting, notifying, and alerting functions, among other functions.

Figure 14A:
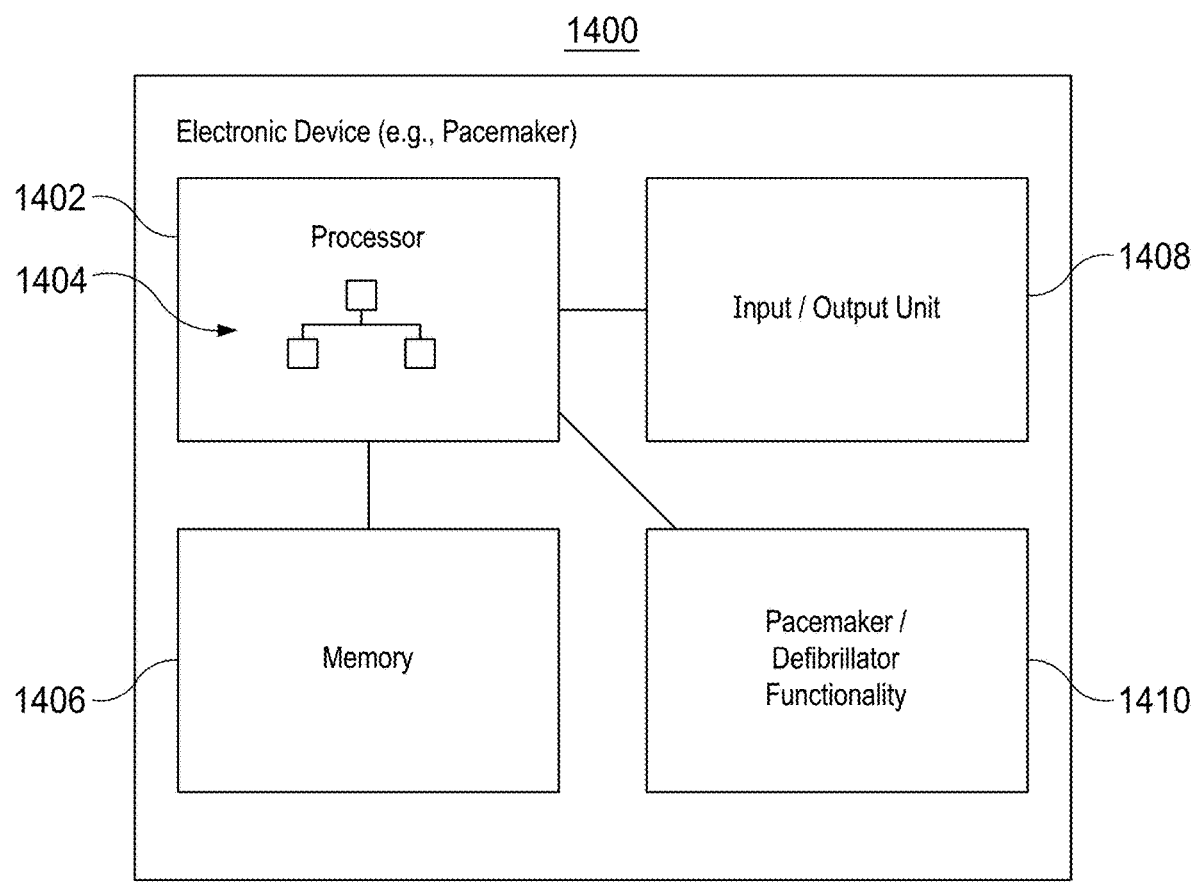
FIGS. 14A and 14B are an illustration of an electronic device, such as an implanted pacemaker and/or defibrillator inclusive of various hardware and software for performing the functions described herein.
Figure 14B:
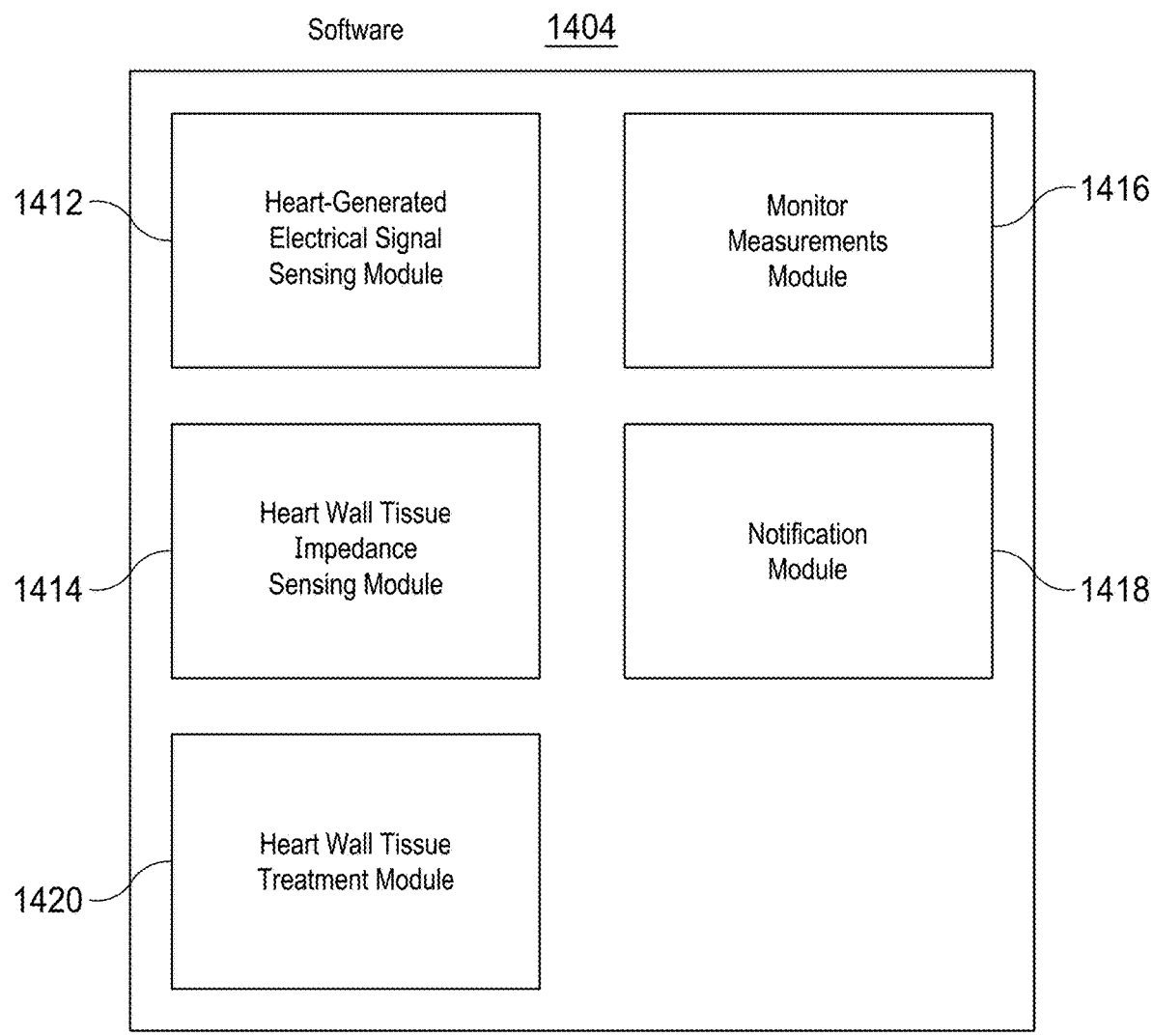

With regard to FIGS. 14A and 14B, illustrations of an electronic device 1400, such as an implanted pacemaker and/or defibrillator inclusive of various hardware and software for performing the functions described herein, is shown. The electronic device may include a processor 1402 that executes software 1404 for performing sensing and measurement functions of heart-generated electrical signals and heart wall tissue impedance measurements, as described herein. The processor 1402 may be in communication with a memory 1406, input/output (I/O) unit 1408, and pacemaker/defibrillator functionality 1410. The memory 1406 may be separate from the processor 1402, but may also be embedded memory. The I/O unit 1408 may include electronics configured to (i) communicate electrical signals to and from other implantable devices, such as the septal electrode 360 and extension electrodes 1008 and (ii) communicate data signals to a remote device, such as a mobile device (e.g., smartphone, server, etc.), using any communications protocol (e.g., BlueTooth®, Wi-Fi®, etc.) to communicate real-time and/or non-real-time information to the remote device. The pacemaker/defibrillator functionality 1410 may be electronics and power sources (e.g., capacitor(s)) configured to perform pacemaking and defibrillating functions of a pacemaker, as understood in the art.

For the sensing functionality in monitoring and identifying heart wall tissue that is becoming problematic using implanted extension electrodes, as previously described, the software 1404 may be configured to monitor and collect electrical signals collected by the extension electrodes positioned against the heart walls inside the left and/or right atriums. Because a limited number of data points may be needed to perform the proper analysis as to whether heart wall tissue is becoming problematic (e.g., forming an area that may lead to AFIB or other heart abnormality or event), maximum data points, minimum data point, or other data points measured against time, independent of time, or otherwise may be measured and recorded. Because heart wall tissue typically takes relatively long periods of time to become problematic, the software 1404 may be configured to store the desired data point (e.g., on a per extension electrode or consecutive extension electrodes basis) and then monitor the values to detect changes over time (e.g., days, week, months, years). Because it is difficult to know whether a sensed signal is accurate, typical processes for performing the monitoring may be performed on a relative basis. For example, timing between sensing an electrical signal between consecutive extension electrodes changing over time may be performed as opposed to an actual timing of sensing the electrical signal.

In an embodiment, two primary measurement functions and two management functions may be performed in monitoring the heart wall tissue. As shown in FIG. 14B, the two measurement functions may include and be implemented using software modules of the software 1404, including (i) measuring heart-generated electrical signals sensing module 1412 and (ii) heart wall tissue impedance sensing module 1414. It should be understood that it is possible to perform one of the two measurement functions and be able to deduce that the heart wall tissue is transitioning to becoming problematic, but being able to perform both functions may provide additional information for a physician. The two management functions may include and be implemented using software modules of the software 1404, including (i) monitor measurements module 1416 to monitor the measured signals over time or if an AFIB event is detected, which may include performing mathematical computations in determining the value(s) to store (e.g., averaging, median, peak sensing, etc.), and (ii) notification module 1418 for reporting whether any of the measured and stored signals cross a threshold to a physician and/or patient in response to detecting that one or more of the measurements has crossed a threshold.

The electronic device 1400 may also include a clock, such as a real-time clock, that may produce a timestamp that may be stored with data that is being generated from the monitoring, thereby associating the collected and generated data with the timestamp. The monitor measurements module 1416 and/or notification module 1418 may be configured to collect and report periodic or aperiodic measurements from the electronic device 1400 to a remote electronic device either locally or on the cloud. Such remote device may be configured to perform the same or additional statistical monitoring of the heart wall tissue. In an embodiment, one such function may include generating a mapping of the measurements onto a graphical heart to make identification of a location of the heart wall tissue that is becoming problematic easier for a physician and/or patient to locate.

A heart wall tissue treatment module 1420 may be configured to enable the electronic device 1400 to perform a treatment by applying energy to the location at which either or both the module 1412 or 1414 determine problematic heart tissue exists. If an AFIB event is determined to be occurring, then the heart wall tissue treatment module 1420 may detect the AFIB event, determine an amount and type of energy signal to apply (e.g., amplitude and frequency), and cause the pacemaker/defibrillator functionality 1410 to activate the treatment, in an embodiment. Command signals generated by the processor 1402 may be communicated to the pacemaker/defibrillator functionality 1410 to cause the energy to be applied by communicating the energy signals to the determined location using one or both of the extension electrode matrices 1006R and 1006L of FIG. 10. The electronic device 1400 may be configured to communicate the energy signals to specific locations on the extension electrode matrices 1006R and 1006L via specific extension electrodes 1008 and possibly to specific nodes along the extension electrodes 1008. The energy treatment may be temporary or permanent treatments that are able to immediately correct an AF event, slow or stall progression of the problematic tissue, or possibly event fully treat the problem. An ablation may also be performed by an operator thereafter, if needed.

The heart wall tissue treatment module 1420 may be configured to identify the type of problem that is occurring and automatically or semi-automatically select and apply a treatment. If semi-automatically, the module may provide a suggestion to an electro-cardiologist and receive a confirmation to proceed with a suggested treatment. The module 1420 may be configured to generate the treatment signals for the pacemaker/defibrillator functionality 1410 to perform or notify the functionality 1410 of the problem and allow the functionality 1410 to determine a proper treatment. It should be understood that the number and types of modules of the software 1404 are illustrative and that additional and/or alternative modules may be configured to sense, identify and locate problematic tissue, notify, and/or treat the cardiac tissue. Moreover, the modules may be configured to cause the processor 1402 to communicate with the I/O unit 1408 to communicate to a remote device to enable a physician using the remote device to obtain information and cause certain features to be performed manually, semi-automatically, or automatically, thereby providing additional information and capabilities in treating a patient. Depending on the configuration of the electronic device and extension electrodes 1008, the electronic device may include a multiplexer to connect specific extension electrodes to the power source that is generating the electrical signals being used to treat the identified regions of the heart wall.

Figure 15:
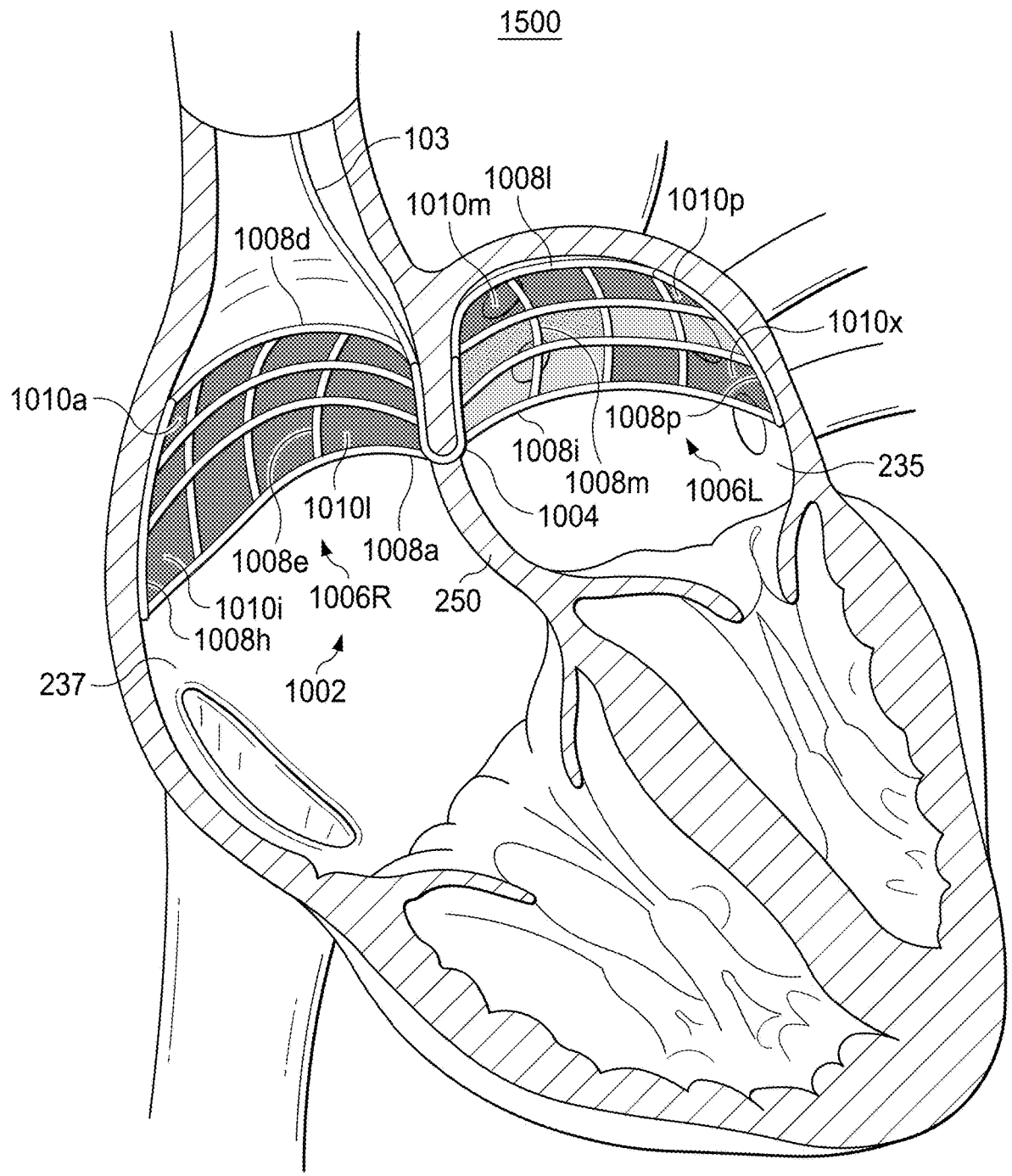
FIG. 15 is an illustration of an illustrative graphical heart that includes the two extension electrode matrices of FIG. 10.

With regard to FIG. 15, an illustration of an illustrative graphical heart that includes the two extension electrode matrices 1006R and 1006L of FIG. 10 is shown. In this case, based on the sensing that is performed as described with regard to FIGS. 12A-13 using the system and functionality described with regard to FIGS. 14A and 14B, a graphical representation of a heart 1500 showing quality of heart wall tissue may be represented in the various cells 1010R and 1010L defined by the respective extension electrode matrices 1006R and 1006L in the respective right and left atriums 237 and 235. In the example shown in FIG. 15, in the right atrium 237, the entirety of the heart wall tissue within the extension electrode matrix 1006R may be represented as "healthy" tissue using a color (e.g., green) or other graphical representation. In the left atrium 235, however, based on the sensed heart-generated electrical signals and/or the measured heart wall tissue impedance signals measured using the extension electrode matrix 1006L, some heart wall tissue may be classified as healthy, other heart wall tissue may be classified as somewhat healthy, and other heart wall tissue may be classified as poor using a color coding or other graphical representation.

It should be understood that while it is possible to monitor the heart wall tissue for changes that may be occurring over time, the system may be configured to detect an actual AFIB event that causes electrical signals and/or electrical signal characteristics of heart wall tissue to be detected that are identified as significant changes to the electrical signals or electrical signal characteristics of heart wall tissue. If such an AF event is sensed and detected, an immediate alert signal may be generated and communicated to a physician and/or patient. As part of the alert, a graphical representation or other representation (e.g., coordinates of the location of the heart wall tissue that likely triggered the AFIB event) may be generated and communicated with the event. The location may be based on being relative to a feature of the heart or relative to the location of the septum through which the septal electrode entered. The affected area may then be modified by delivering energy in several different ways in order to terminate the activity from the focus or foci.

As shown, the top row of cells 1010*m*-1010*p* and 1010*w*-1010*x* are represented as healthy (e.g., colored green), 1010*q* and 1010*r* are classified as poor (e.g., colored red), and 1010*s*-1010*v* are classified as somewhat healthy (e.g., colored yellow). It should be understood that the measurements are dynamically generated such that the colors may dynamically change over time based on the measurements. The cells 1010 are based on the configuration of the extension electrode matrices 1006R and 1006L and the ability for the electronic device to be able to measure and detect electrical signals and/or electrical parameters in the cells. In some configurations, only rows are measured, while in other configurations, only columns are measured. If both rows and columns are to be measured, then the electrical conductivity and measurement capability is to provide for those measurements. In embodiment, timing of measurement signals may be used to determine where along the different extension electrodes and/or nodes that the measurements represent.

Some embodiments are directed to a support structure for a pacemaker lead. The support structure is coupled to the pacemaker lead and is configured to restrain a portion of the pacemaker lead against a person's atrial wall. Examples of the support structure are described herein and include, for example, a U-shaped dip, a lattice, etc. the support structure may comprise a shape memory material (e.g., Nitinol).

One embodiment of a process of manufacturing an implantable heart device may include forming a structure configured to be retained to an atrial septum. An extension electrode may be attached to a portion of the structure to cause the extension electrode to be positioned against the endocardium of the atrial septum, where the extension electrode may be configured to have an elongated portion thereof to maintain contact with the endocardium of the left atrium away from the atrial septum.

Attaching an extension electrode may include attaching an extension electrode formed of shape memory material. The process may further include connecting a lead to the structure to conduct electrical signals to the structure and extension electrode. Alternatively, a leadless pacemaker may be to the structure to apply electrical signals to the structure and extension electrode.

One embodiment of a process for implanting a heart device may include introducing an extension electrode into a blood vessel. The extension electrode may be traversed through the blood vessel and into the right atrium of a patient's heart. The extension electrode may be inserted through a right-side wall junction and into a wall of the left atrium so that the extension electrode is intramural with the left atrium.

The extension electrode may be secured to remain within the wall of the left atrium. Securing the extension electrode may include applying a structure to the atrial septum. Securing the extension electrode may include inserting a securing device into the right-side wall junction that prevents the extension electrode from exiting from the wall.

The process may further include extending a lead from the extension electrode, and connecting the lead to a pacemaker. Securing the extension electrode may include securing the extension electrode without causing the endocardium of the left atrium to be breached.

Using the structures described herein, a method for implanting a lead in the left side of a heart can comprise introducing the lead into a blood vessel, advancing the lead into a left atrium, fixing a distal region of the lead in position flush against the atrial septum with anchor elements on both sides of the atrial septum, and affixing an electrode on the lead in contact with the endocardium of the heart. Further, advancing the lead into the left atrium may include advancing the electrode beyond the septum and into continuous contact with the atrial wall. A lattice may be positioned in the left atrium to maintain the distal region of the lead in contact with the atrial wall.

AFIB Monitoring and Future AFIB Event Prevention

One embodiment of a method for sensing heart tissue that causes atrial fibrillation (AFIB) may include measuring, via a plurality of electrical conductors disposed on endocardium of a heart wall within respective at least one chamber of a heart, an electrical signal characteristic. A determination may be made that the electrical signal characteristic is indicative of an AFIB event. Responsive to determining that the electrical signal characteristic is indicative of an AFIB event, a location of the heart wall within the heart chamber(s) relative to positions of the electrical conductors that caused the AFIB event may be identified.

Measuring via the electrical conductors may include measuring via multiple electrical conductors that extend along a surface of the wall of the heart chamber(s). Measuring via the electrical conductors that extend along the endocardium of the wall of the heart chamber(s) may include measuring via multiple electrical conductors having a mesh configuration. Identifying a location of the heart wall that caused the AFIB event may include identifying a location bounded by a mesh region. Measuring may include measuring electrical signal values at nodes of the mesh of the electrical conductors. Measuring an electrical characteristic may include measuring an impedance of the heart wall between consecutive electrical conductors that extend along a common wall.

Measuring the electrical signal characteristic may include measuring an electrical current or voltage produced by the sinus node of the heart by each of the electrical conductors. Data indicative of the electrical current sensed by each of the electrical conductors in response to determining that the electrical signal characteristic is indicative of an AFIB event may be stored.

The process may further include storing, within a non-transitory memory of an electronic device, the identified location of the heart wall, recording, by the electronic device, a time associated with the AFIB event in association with the identified location, and communicating the identified location of the heart wall to cause an electronic display to present the location for a user. The information gathered may be used to deliver energy in one of many configurations to terminate the abnormal signal, thereby eliminating the focus or foci of the initiating AF event.

Coordinates of the electrical conductors within a patient's heart relative to features of the heart chamber(s) in which the electrical conductors reside may be stored, thereby enabling a mapping of the wall of the at least one chamber of the heart. Storing, within a non-transitory memory of an electronic device, may include storing, within a non-transitory device of a pacemaker or defibrillator. Measuring an electrical signal characteristic may include measuring an impedance between successive electrical conductors. The process may further include comparing the measured impedance between successive conductors over time to identify changes over time between the successive electrical conductors.

One embodiment of an electronic device, such as a pacemaker, may include a non-transitory memory, an input channel configured to receive a plurality of electrical signals received from multiple extension electrodes that extend along a heart wall within at least one chamber of a heart, and a processor in electrical communication with the non-transitory memory and input channel. The processor may be configured to measure each of the electrical signals. Respective measured electrical signals may be stored in the non-transitory memory. A determination as to whether any of the measured electrical signals are indicative of heart tissue that causes heart-generated electrical signals to be delayed, accelerated, or attenuated in ways that are different from healthy heart tissue. Responsive to determining that the electrical signals are indicative of a heart tissue that causes heart-generated electrical signals to be delayed, accelerated, or attenuated in ways that are different from healthy heart tissue, a notification signal indicative of the location may be generated.

The electrical signals may be electrical signals sensed generated by the sinoatrial node of the heart sensed by each of the extension electrodes. The extension electrodes may extend along endocardium of at least one of the atriums of the heart. The electronic device may be a pacemaker.

The input channel may include receiver electronics configured to sense the heart-generated electrical signals. The input channel may include electronics configured to sense impedance of heart wall tissue between successive extension electrodes. The extension electrodes may be at least partially parallel with one another (e.g., a portion of the extension electrodes are parallel with one another, but not be completely parallel due to the configuration of the heart chamber(s)). The extension electrodes may define a matrix of rows and columns.

The illustrations included herewith are not meant to be actual views of any particular systems, memory device, architecture, or process, but are merely idealized representations that are employed to describe embodiments herein. Elements and features common between figures may retain the same numerical designation except that, for ease of following the description, for the most part, reference numerals begin with the number of the drawing on which the elements are introduced or most fully described. In addition, the elements illustrated in the figures are schematic in nature, and many details regarding the physical layout and construction of a memory array and/or all steps necessary to access data may not be described as they would be understood by those of ordinary skill in the art.

As used herein, the singular forms "a," "an," and "the" are intended to include the plural forms as well, unless the context clearly indicates otherwise.

As used herein, "or" includes any and all combinations of one or more of the associated listed items in both, the conjunctive and disjunctive senses. Any intended descriptions of the "exclusive-or" relationship will be specifically called out.

As used herein, the term "configured" refers to a structural arrangement such as size, shape, material composition, physical construction, logical construction (e.g., programming, operational parameter setting) or other operative arrangement of at least one structure and at least one apparatus facilitating the operation thereof in a defined way (e.g., to carry out a specific function or set of functions).

As used herein, the phrases "coupled to" or "coupled with" refer to structures operably connected with each other, such as connected through a direct connection or through an indirect connection (e.g., via another structure or component).

The foregoing method descriptions and/or any process flow diagrams are provided merely as illustrative examples and are not intended to require or imply that the steps of the various embodiments must be performed in the order presented. As will be appreciated by one of skill in the art, the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations may be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to and/or in communication with another code segment or a hardware circuit by passing and/or receiving information, data, arguments, parameters, or memory contents. Information, arguments, parameters, data, etc. may be communicated (e.g., passed, forwarded, and/or transmitted) via any suitable means including memory sharing, message passing, token passing, network transmission, etc.

The actual software code or specialized control hardware used to implement these systems and methods is not limiting of the disclosure. Thus, the operation and behavior of the systems and methods were described without reference to the specific software code being understood that software and control hardware can be designed to implement the systems and methods based on the description here.

When implemented in software, the functions may be stored as one or more instructions or code on a non-transitory computer-readable or processor-readable storage medium. The steps of a method or algorithm disclosed here may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The previous description is of various preferred embodiments for implementing the disclosure, and the scope of the invention should not necessarily be limited by this description. The scope of the present invention is instead defined by the claims.

What is claimed is:

1. A method for sensing heart tissue that causes atrial fibrillation (AFIB), comprising:
    measuring an electrical signal characteristic via at least one electrical conductor that is permanently implanted and secured to the inter atrial septum, the at least one electrical conductor having at least one extension electrode that extends therefrom and along endocardium beyond the atrial septum of a heart wall within at least one chamber of a heart;
    determining that the electrical signal characteristic is indicative of an AFIB event; and
    responsive to determining that the electrical signal characteristic is indicative of an AFIB event, identifying a location of the heart wall within the at least one heart chamber relative to positions of the at least one respective extension electrode that caused the AFIB event.

2. The method according to claim 1, wherein measuring via the at least one electrical conductor includes measuring via respective side surfaces of the at least one extension electrode that respectively extends along the endocardium of the heart wall of the at least one heart chamber.

3. The method according to claim 2, wherein measuring via the at least one electrical conductor having the at least one extension electrode extending therefrom and extending along the endocardium of the wall of the at least one heart chamber includes measuring via a plurality of the at least one extension electrode having a mesh configuration.

4. The method according to claim 3, wherein identifying the location of the heart wall that caused the AFIB event includes identifying a location bounded by a mesh region.

5. The method according to claim 4, wherein measuring includes measuring electrical signal values at nodes of the mesh of the extension electrodes.

6. The method according to claim 1, wherein measuring the electrical characteristic includes measuring an impedance of the heart wall between consecutive extension electrodes that extend along a common wall.

7. The method according to claim 1, wherein measuring the electrical signal characteristic includes measuring an electrical current produced by the sinus node of the heart by each of the at least one extension electrode.

8. The method according to claim 7, further comprising storing data indicative of the electrical current sensed by each of the at least one extension electrode in response to determining that the electrical signal characteristic is indicative of the AFIB event.

9. The method according to claim 7, wherein measuring an electrical signal characteristic includes measuring an electrical signal characteristic of the electrical current produced by the sinus node along the endocardium of the left atrium within which the at least one extension electrode is positioned.

10. The method according to claim 1, further comprising:
    storing, within a non-transitory memory of an electronic device, the identified location of the heart wall;
    recording, by the electronic device, a time associated with the AFIB event in association with the identified location; and
    communicating the identified location of the heart wall to cause an electronic display to present the location for a user.

11. The method according to claim 10, further comprising storing coordinates of the at least one extension electrode within a patient's heart relative to features of the at least one chamber in which the at least one extension electrode resides, thereby enabling a mapping of the wall of the at least one chamber of the heart.

12. The method according to claim 10, wherein storing, within a non-transitory memory of an electronic device, includes storing, within the non-transitory device of a pacemaker or defibrillator.

13. The method according to claim 1, wherein measuring the electrical signal characteristic includes measuring an impedance between successive extension electrodes.

14. The method according to claim 13, further comprising comparing a measured impedance between successive extension electrodes over time to identify changes of the measured impedance over time between the successive extension electrodes.

15. The method according to claim 1, further comprising:
    generating an energy signal; and
    causing the energy signal to be applied to the identified location of the heart wall.

16. The method according to claim 1, wherein measuring via the plurality of electrical conductors further includes measuring via the plurality of electrical conductors having the at least one extension electrode that further extends along at least a portion of the inter atrial septum.

17. The method according to claim 1, wherein measuring an electrical signal characteristic via at least one extension electrode includes measuring an electrical characteristic via at least one extension electrode that is an extension portion of the permanently implanted at least one electrical conductor.

18. The method according to claim 1, wherein measuring an electrical signal characteristic via at least one extension electrode includes measuring an electrical characteristic via at least one extension electrode beyond the atrial septum of a heart wall within the left atrium of a heart.

* * * * *